United States Patent [19]

Sih

[11] 4,228,104
[45] Oct. 14, 1980

[54] 2-DECARBOXY-2-HYDROXYMETHYL-19-HYDROXY-PG$_1$ ANALOGS

[75] Inventor: John C. Sih, Kalamazoo, Mich.

[73] Assignee: The Upjohn Company, Kalamazoo, Mich.

[21] Appl. No.: 25,899

[22] Filed: Apr. 2, 1979

[51] Int. Cl.$^3$ .................... C07C 35/06; C07C 49/395
[52] U.S. Cl. .................................. 568/379; 568/838; 424/331; 424/343
[58] Field of Search .......................... 260/586; 568/838

[56] References Cited

U.S. PATENT DOCUMENTS 4,127,612  11/1978  Kluenden ............................ 260/586

Primary Examiner—Robert Gerstl
Attorney, Agent, or Firm—Robert A. Armitage; Morris L. Nielsen

[57] ABSTRACT

Prostaglandin derivatives having a 19,20-didehydro, a 19-hydroxy, or a 19-keto feature are disclosed, including processes for preparing them and the appropriate intermediates.

A typical 19-hydroxy compound of this invention is 19-hydroxy-19-methyl-PGF$_{2\alpha}$, methyl ester, represented by the formula

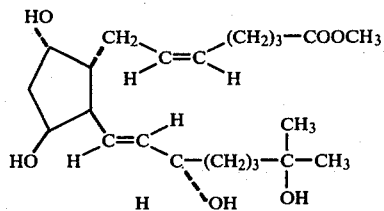

54 Claims, No Drawings

2-DECARBOXY-2-HYDROXYMETHYL-19-HYDROXY-PG₁ ANALOGS

DESCRIPTION

BACKGROUND OF THE INVENTION

This invention relates to prostaglandin derivatives and to processes for preparing them.

The prostaglandins are a well-known group of organic compounds, including for example Prostaglandin $F_{2\alpha}$ ($PGF_{2\alpha}$) represented by formula I.

The prostaglandins are related to prostanoic acid which has the structure and atom numbering of formula II.

For background on prostaglandins, see for example Bergstrom et al., Pharmacol. Rev. 20, 1 (1968). For nomenclature of the prostaglandins, see N. A. Nelson, J. Medic. Chem. 17, 911 (1974). In the literature, $PGF_{2\alpha}$ may be variously indexed, for example as a derivative of "prosta-5,13-dien-1-oic acid" or "5-heptenoic acid". With respect to "R" and "S" usage, as for the stereochemistry of substituent groups at C-15 herein, see R. S. Cahn, J. Chem. Ed. 41, 116 (1964).

As drawn herein the formulas represent a particular optically active isomer having the same absolute configuration as $PGE_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

Included in the background of chemical literature and patents are the following: K. Green et al., J. Lipid Res. 5, 117 (1969), $PGE_3$ and $PGF_{3\alpha}$, methyl esters; B. Samuelsson, U.S. Pat. No. 3,657,316, 19-hydroxy-$PGE_1$; P. L. Taylor et al., Nature 250, 665 (1974) and FEBS Letters 57, 22 (1975), 19-hydroxy-PGE's and -PGF's; W. Marscheck et al., U.S. Pat. No. 3,878,046, 11-deoxy-19-hydroxy-$PGE_2$; C. J. Sih et al., J. Am. Chem. Soc. 91, 3685 (1969), 19-oxo-$PGE_2$ and -13,14-dihydro-$PGE_1$; J. C. Sih, Prostaglandins 13, 831 (1977), (19R)-19-hydroxy-$PGE_1$, -$PGE_2$, -$PGF_{1\alpha}$, and -$PGF_{2\alpha}$; Brit. Pat. Spec. No. 1,388,443, Derwent Farmdoc Abstract No. 00520U, reduction of 9,19-diketoprostanoic acids; A. F. Marx et al., U.S. Pat. No. 4,054,595, 18- and 19-hydroxy-prostaglandins; J. E. Pike, U.S. Pat. No. 3,922,297, 19-methyl-prostaglandins; R. K. Beerthuis et al., Rec. Trav. Chim. Pays. Bas 90, 943 (1971), cis-$\Delta^{18}$-$PGE_1$; K. G. Untch et al., J. Am. Chem. Soc. 100, 6211 (1978), dl-19-hydroxy-$PGE_1$ and dl-13-cis-15-epi-19-hydroxy-$PGE_1$; German Offenleg. 2,505,519 (Derwent Farmdoc Abstract No. 56027W) or Chem. Abs. 84, 43441w, 20-hydroxy-$PGE_2$ or -$PGF_{2\alpha}$.

Subsequent to this invention there appeared U.S. Pat. No. 4,127,612 to H. C. Kluender et al. for 2-decarboxy-2-hydroxymethyl-19-hydroxy-$PGE_1$ and 19-hydroxy $PGE_1$ carbinol analogues.

SUMMARY OF THE INVENTION

It is the purpose of this invention to provide novel products having pharmacological activity. It is a further purpose to provide a process for preparing these products and their intermediates. More specifically, there are provided certain prostaglandin derivatives having a 19,20-didehydro, a 19-hydroxy, or a 19-keto feature.

Accordingly there are provided 19,20-didehydro compounds of formula III, wherein the terms D, Q, $R_1$, and the like are defined in the TABLE of Definition of Terms for Formulas herein, together with other terms used hereinafter.

TABLE
Definition of Terms for Formulas

A is
alkyl of one to 4 carbon atoms, inclusive, phenyl, phenyl substituted with one to 2 fluoro, chloro, or alkyl of one to 4 carbon atoms, inclusive, or aralkyl of 7 to 12 carbon atoms, inclusive, the A groups being the same or different.

D is
(1) cis-CH=CH—CH₂—(CH₂)$_g$—CH₂—
(2) cis-CH=CH—CH₂—(CH₂)$_g$—CF₂—
(3) cis-CH₂—CH=CH—CH₂—CH₂—
(4) trans-(CH₂)₃—CH=CH—
(5) —(CH₂)₃—(CH₂)$_g$—CH₂—
(6) —(CH₂)₃—CH₂—CF₂—
(7) —(CH₂)₃—O—CH₂—
(8) —(CH₂)₂—O—(CH₂)₂—
(9) —CH₂—O—(CH₂)₃—

(10) 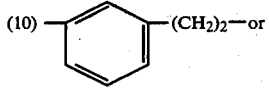—(CH₂)₂— or

(11) 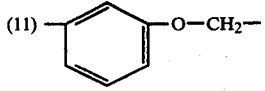—O—CH₂— wherein g is zero, one, two, or three.
Hal is chloro, bromo, or iodo.
Q is

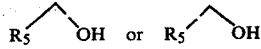

wherein $R_5$ is hydrogen or alkyl of one to 4 carbon atoms, inclusive.
$Q_1$ is

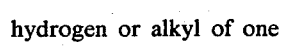

wherein $R_5$ is hydrogen or alkyl of one to 4 carbon atoms, inclusive, and $R_{15}$ is a blocking group as defined below.
$Q_2$ is

wherein $R_9$ is alkyl of one to 4 carbon atoms, inclusive.
$R_1$ is
(1) —COOR₆
(2) —CH₂OH
(3) —CH₂N(R₇)(R₈)

$$-\overset{O}{\underset{\|}{C}}-N(R_7)(R_8) \quad (4)$$

$$-\overset{O}{\underset{\|}{C}}-NH-SO_2-R_{29} \text{ or} \quad (5)$$

-continued

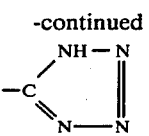
(6)

wherein R₆ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl groups of one to 3 carbon atoms, inclusive;

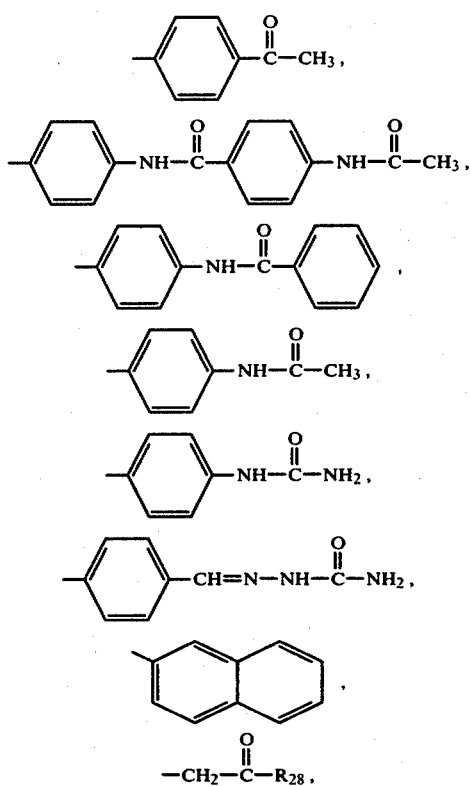

wherein R₂₈ is phenyl, p-bromophenyl, p-biphenylyl, p-nitrophenyl, p-benzamidophenyl, or 2-naphthyl, or (o) a pharmacologically acceptable cation; wherein R₇ and R₈ are hydrogen, alkyl of one to 12 carbon atoms, inclusive, benzyl, or phenyl, being the same or different, and wherein R₂₉ is hydrogen, alkyl of one to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive.

R₂ is hydrogen, hydroxyl, or hydroxymethyl.

R₃ and R₄ are hydrogen, alkyl of one to 4 carbon atoms, inclusive, or fluoro, being the same or different, with the proviso that one of R₃ and R₄ is fluoro only when the other is hydrogen or fluoro.

R₅ is hydrogen or alkyl of one to 4 carbon atoms, inclusive.

R₆ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl groups of one to 3 carbon atoms, inclusive;

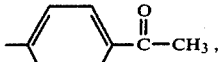
(g)

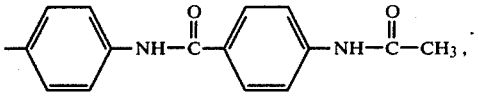
(h)

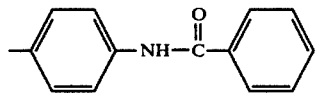
(i)

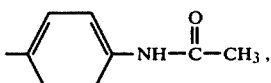
(j)

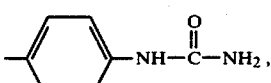
(k)

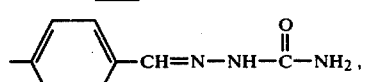
(l)

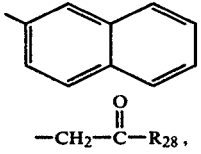
(m)

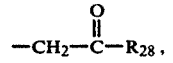
(n)

wherein R₂₈ is phenyl, p-bromophenyl, p-biphenylyl, p-nitrophenyl, p-benzamidophenyl, or 2-naphthyl, or (o) a pharmacologically acceptable cation.

R₇ and R₈ are hydrogen, alkyl of one to 12 carbon atoms, inclusive, benzyl, or phenyl, being the same or different.

R₉ is alkyl of one to 4 carbon atoms, inclusive.

R₁₀ and R₁₁ are hydrogen or fluoro.

R₁₂ is alkyl of one to 12 carbon atoms, inclusive.

R₁₃ is hydrogen, —OR₁₅, or —CH₂OR₁₅, wherein R₁₅ is a blocking group defined below.

R₁₄ is hydrogen, —OR₁₈, or —CH₂OR₁₈, wherein R₁₈ is a carboxyacyl blocking group defined below.

R₁₅ is a blocking group including tetrahydropyranyl, tetrahydrofuranyl, or a group of the formula

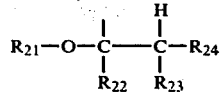

wherein R₂₁ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein R₂₂ and R₂₃ are the same or different, being hydrogen, alkyl of one to 4 carbon atoms, inclusive, phenyl or phenyl substituted with one, 2, or 3 alkyl of one to 4 carbon atoms, inclusive, or, when R₂₂ and R₂₃ are taken together, —(CH₂)ₐ— or —(CH₂)_b—O—(CH₂)_c— wherein a is 3, 4, or 5, b is one, 2, or 3, and c is one, 2, or 3 with the proviso that b plus c is 2, 3, or 4, and wherein R₂₄ is hydrogen or phenyl.

$R_{16}$ is hydrogen or methyl.
$R_{17}$ is hydrocarbyl of one to 18 carbon atoms, inclusive.
$R_{18}$ is carboxyacyl including

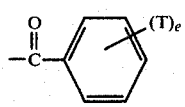 (a)

wherein "T" is alkyl of one to 4 carbon atoms, inclusive, bromo, phenylalkyl of 7 to 10 carbon atoms, inclusive, or nitro, and "e" is zero to 5, inclusive, provided that not more than two T's are other than alkyl, and that the total number of carbon atoms in the T's does not exceed 10 carbon atoms.

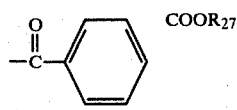 (b)

wherein $R_{27}$ is alkyl of one to 4 carbon atoms, inclusive,

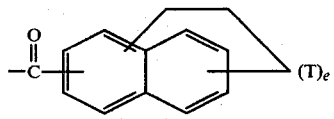 (c)

wherein "T" and "e" are as defined above, or

 (d)

wherein $R_{25}$ is hydrogen, alkyl of one to 19 carbon atoms, inclusive, or alkyl of 7 to 12 carbon atoms, inclusive, wherein alkyl or aralkyl are substituted with zero to 3 halo atoms.

$R_{19}$ is the same as $R_1$ but with the proviso that $R_{19}$ is not —COOH or —COOR$_{12}$ wherein $R_{12}$ is alkyl of one to 12 carbon atoms, inclusive, when (A) $R_2$ is hydroxy, $R_3$ and $R_4$ are hydrogen, Q is

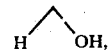

W is

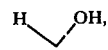 or 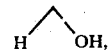, and either (1) D is cis—CH=CH—CH$_2$—(CH$_2$)$_g$—CH$_2$— and X is trans—CH=CH—, or (2) D is —(CH$_2$)$_3$—(CH$_2$)$_g$—CH$_2$— and X is trans—CH=CH— or —CH$_2$CH$_2$—, (B) $R_2$, $R_3$, and $R_4$ are hydrogen, W is

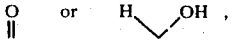

D is —(CH$_2$)$_3$—(CH$_2$)$_g$—CH$_2$—, and X is trans—CH=CH—, or (C) $R_2$, $R_3$, and $R_4$ are hydrogen, Q is

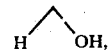,

W is

D is cis—CH=CH—CH$_2$—(CH$_2$)$_g$—CH$_2$— and X is trans—CH=CH—.

$R_{20}$ is the same as $R_1$ but with the proviso that $R_{20}$ is not —COOH or —COOR$_{12}$ wherein $R_{12}$ is alkyl of one to 12 carbon atoms, inclusive, when Q is

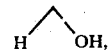, $R_2$ is hydroxy, $R_3$ and $R_4$ are hydrogen, W is

and either (1) D is cis—CH=CH—CH$_2$—(CH$_2$)$_g$—CH$_2$— and X is trans—CH=CH—, or (2) D is —(CH$_2$)$_3$—(CH$_2$)$_g$—CH$_2$— and X is —CH$_2$CH$_2$—.

$R_{21}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive.

$R_{22}$ and $R_{23}$ are hydrogen, alkyl of one to 4 carbon atoms, inclusive, phenyl or phenyl substituted with one, 2, or 3 alkyl of one to 4 carbon atoms, inclusive, being the same or different, or, when $R_{22}$ and $R_{23}$ are taken together, —(CH$_2$)$_a$— or —(CH$_2$)$_b$—O—(CH$_2$)$_c$— wherein a is 3, 4, or 5, b is one, 2, or 3, and c is one, 2, or 3 with the proviso that b plus c is 2, 3, or 4.

$R_{24}$ is hydrogen or phenyl.

$R_{25}$ is hydrogen, alkyl of one to 19 carbon atoms, inclusive, or aralkyl of 7 to 12 carbon atoms, inclusive, wherein alkyl or aralkyl are substituted with zero to 3 halo atoms.

$R_{26}$ is alkyl of one to 3 carbon atoms, inclusive.

$R_{27}$ is alkyl of one to 4 carbon atoms, inclusive.

$R_{28}$ is phenyl, p-bromophenyl, p-biphenylyl, p-nitrophenyl, p-benzamidophenyl, or 2-naphthyl.

$R_{29}$ is hydrogen, alkyl of one to 12 carbon atoms, inclusive, aralkyl of 7 to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl in which the alkoxy group consists of one to 4 carbon atoms, inclusive.

$R_{30}$ is alkyl of one to 10 carbon atoms, inclusive, aralkyl of 7 to 12 carbon atoms, inclusive, phenyl, or phenyl substituted with one or 2 chloro or alkyl groups of one to 3 carbon atoms, inclusive.

(T)$_e$ is alkyl of one to 4 carbon atoms, inclusive, phenylalkyl of 7 to 10 carbon atoms, inclusive, or nitro, and e is zero to 5, inclusive, provided that not more than two T's are other than alkyl, and that the total number of carbon atoms in the T's does not exceed 10 carbon atoms.

THP is tetrahydropyran-2-yl.
W is

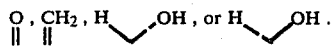

W' is

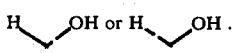

W" is

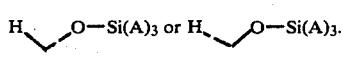

wherein A is as defined above.
W'" is

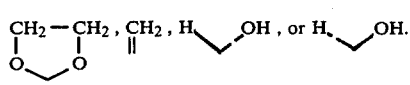

X is cis- or trans-CH=CH—, —C≡C—, or —CH$_2$CH$_2$—.

a is 3, 4, or 5.

b is one, 2, or 3.

c is one, 2, or 3 with the proviso that b plus c is 2, 3, or 4.

e is zero, one, 2, 3, 4, or 5.

g is zero, one, 2, or 3.

j is one, 2, or 3.

p is one, 2, or 3 with the proviso that j plus p is 4.

~ (wavy line) indicates attachment in alpha or beta configuration.

± indicates a mixture of R and S epimers.

END OF TABLE

There are further provided 19-hydroxy compounds of formula IV. Included are the 19(S), 19(R), and 19(R,S) compounds.

There are also provided 19-keto compounds of formula V.

There are also provided 19-hydroxy-19-methyl compounds of formula VI.

Among the compounds of formulas III, IV, V, and VI there are PGE-type compounds when R$_2$ is hydroxyl and W is

there are 9-deoxo-9-methylene-PGE-type compounds when W is

there are PGF$_\alpha$-type compounds when W is

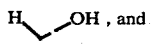

there are PGF$_\beta$-type compounds when W is

There are 11-deoxy compounds when R$_2$ is hydrogen, and there are 11-deoxy-11-hydroxymethyl compounds when R$_2$ is hydroxymethyl.

There are included acids, esters, and salts when R$_1$ is —COOR$_6$, there are C-1 alcohols, i.e. 2-decarboxy-2-hydroxymethyl derivatives when R$_1$ is —CH$_2$OH, there are C-1 amines, i.e. 2-decarboxy-2-aminomethyl derivatives when R$_1$ is —CH$_2$N(R$_7$)(R$_8$), there are C-1 amides, when R$_1$ is

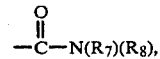

there are sulfonylamides, when R$_1$ is

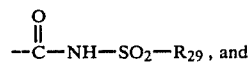

there are C-1 tetrazol derivatives when R$_1$ is

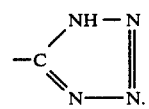

For those compounds of formula III–VI wherein Q is

i.e. wherein the C-15 hydroxyl group is attached to the side chain in alpha configuration, the configuration at C-15 is identical with that of the naturally occuring prostaglandins such as PGE$_1$ obtained from mammalian tissues. The 15-epimer compounds are represented by formulas III–VI when Q is

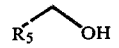

and are identified variously as "15-epi" or "15β" or "15R" by the appropriate prefix in the name. As is known in the art, "R" and "S" designations depend on the neighboring substituents. See R. S. Cahn, J. Chem. Ed. 41, 116 (1964).

The cis-13 prostaglandin derivatives are generally represented herein with a lower side chain shown partially as follows

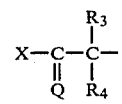

wherein X is cis—CH=CH— and, for the S configuration, Q is

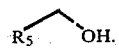

This is intended to be equivalent to the representation

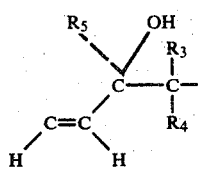

for the S configuration with the C-15 hydroxy in the 15β configuration as drawn (cf. U.S. Pat. No. 4,026,909 column 13).

A typical example of the formula-III compounds is represented by formula VII and is named by the trivial name 19,20-didehydro-PGF$_{2\alpha}$, methyl ester, alternatively $\Delta^{19}$-PGF$_{2\alpha}$, methyl ester. The full chemical name is (5Z,9α,11α,13E,15S) 9,11,15-trihydroxy-prosta-5,13,19-trien-1-oic acid, methyl ester. The formula-VII compound is a species of the formula-III compounds wherein D is cis—CH=CH—(CH$_2$)$_3$—, Q is

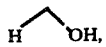

R$_1$ is —COOCH$_3$, R$_2$ is —OH, R$_3$ and R$_4$ are hydrogen, W is

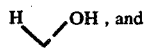

X is trans—CH=CH—.

The nomenclature of these compounds follows that of the prostaglandins. For example, compounds having longer or shorter side chains are named as "homo" or "nor" compounds, respectively.

The products of this invention within the scope of formula III–VI are extremely potent in causing various biological responses. For that reason, these compounds are useful for pharmacological purposes. A few of those biological responses are: inhibition of blood platelet aggregation, inhibition of gastric secretion and reduction of undesirable gastrointestinal effects from systemic administration of prostaglandin synthetase inhibitors, controlling spasm and facilitating breathing in asthmatic conditions, and decongesting nasal passages.

Because of these biological responses, these novel compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits and monkeys.

These compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative surgery, and to treat conditions such as arthrosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.01 to about 10 mg. per kg. of body weight per day are used, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through limbs and organs, e.g. heart and kidneys, whether attached to the original body, detached and being preserved or prepared for transplant, or attached to a new body. Blocking of aggregated platelets is avoided by the presence to these compounds. For this purpose, the compound is added gradually or in single or multiple portions to the circulating blood, to the blood of the donor person or animal, to the perfused body portion, attached or detached, to the recipient, or to two or all of those at a total steady state dose of about 0.001–1.0 μg./ml. of whole blood. These compounds are also useful in preparing platelet-rich concentrates from blood for use in treating thrombocytopenia or in chemotherapy.

These compounds are also useful in mammals, including man and certain useful animals, e.g. dogs and pigs, to reduce and control excessive gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.01 to about 10 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the formula III–VI compound and the anti-inflammatory prostaglandin synthetase inhibitor. See Partridge et al., U.S. Pat. No. 3,781,429, for a disclosure as to the administration of certain prostaglandins of the E and A series. The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration. The formula III–VI compound is administered along with the anti-inflammatory prostaglandin synthetase inhibitor either by the same route of administration or by a different route. The dosage regimen for the formula III–VI compound in accord with this treatment will depend upon a variety of factors, including the type, age, weight, sex and medical condition of the mammal, the nature and dosage regimen of the anti-inflammatory synthetase inhibitor being administered to the mammal, and the sensitivity of the particular formula III–VI compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the formula III-VI compound to reduce and then substantially to eliminate those undesirable effects.

These compounds are also useful in the treatment of asthma. For example they are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use the compound can be combined advantageously with other anti-asthmatic agents, such as sympathomimetics (isoproterenol, phenylephrine, ephedrine, etc.), xanthine derivatives (theophylline and aminophylline), and corticosteroids (ACTH and prednisolone).

These compounds are effectively administered to human asthma patients by oral inhalation or by aerosol inhalation. For administration by the oral inhalation route with conventional nebulizers or by oxygen aerosolization it is convenient to provide the formula III-VI ingredient in dilute solution, preferably at concentrations of about 1 part of medicament to from about 100 to 200 parts by weight of total solution. Entirely conventional additives may be employed to stabilize these solutions or to provide isotonic media, for example, sodium chloride, sodium citrate, citric acid, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispersing agent such as oleyl alcohol. Suitable means to employ the aerosol inhalation therapy technique are described fully in U.S. Pat. No. 2,868,691 for example.

These compounds are useful in mammals, including man, as nasal decongestants and are used for this purpose in a dose range of about 10 $\mu$g to about 10 mg. per ml. of a pharmacologically suitable liquid vehicle or as an aerosol spray, both for topical application.

These compounds are also useful in treating peripheral vascular disease in humans. The term peripheral vascular disease as used herein means disease of any of the blood vessels outside of the heart and to disease of the lymph vessels, for example, frostbite, ischemic cerebrovascular disease, arteriovenous, fistulas, ischemic leg ulcers, phlebitis, venous insufficiency, gangrene, hepatorenal syndrome, ductus arteriosus, non-obstructive mesenteric ischemia, arteritis lymphangitis and the like. These examples are included to be illustrative and should not be construed as limiting the term peripheral vascular disease. For these conditions the compounds are administered orally or parenterally via injection or infusion directly into a vein or artery. The dosages of such compounds are in the range of 0.01-1.0 $\mu$g. administered by infusions at an hourly rate or by injection on a daily basis, i.e. 1-4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed. These compounds are accordingly useful for treating peripheral vascular diseases in the extremities of humans who have circulatory insufficiencies in said extremities, such treatment affording relief of rest pain and induction of healing of ulcers. For a complete discussion of the nature of and clinical manifestations of human peripheral vascular disease and the method previously known of its treatment with prostaglandins see South African Pat. No. 74/0149 referenced as Derwent Farmdoc No. 58400V. See Elliott et al., Lancet, Jan. 18, 1975, pp. 140-142.

Surprisingly, the formula IV-VI compounds have little or no effect on stimulation of smooth muscle. The formula-III 19,20-didehydro compounds, however, are extremely potent in causing stimulation of smooth muscle.

The formula-III compounds are not only active in causing stimulation of smooth muscle, but are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range of 0.01 to 2 mg. per kg. of body weight per day, the exact dose depending on the age, weight, and condition of the patient or animal.

The formula-III compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The formula-III compounds are further useful for controlling the reproductive cycle in menstruating female mammals, including humans. By the term menstruating female mammals is meant animals which are mature enough to menstruate, but not so old that regular menstruation has ceased. For that purpose the compound is administered systemically at a dose level in the range of 0.01 mg to about 20 mg. per kg. of body weight of the female mammal, advantageously during a span of time starting approximately at the time of ovulation and ending approximately at the time of mensus or just prior to mensus. Intravaginal and intrauterine routes are alternate methods of administration. Additionally, expulsion of an embryo or a fetus is accomplished by similar administration of the compound during the first or second trimester of the normal mammalian gestation period.

The formula-III compounds are further useful in causing cervical dilation in pregnant and non-pregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by these compounds is also useful in operative gynecology such as D and C (Cervical Dilation and Uterine Curettage) where mechanical dilation may cause perforation of the uterus, cervical tears, or infections. It is also useful for diagnostic procedures where dilation is necessary for tissue examination. For these purposes, the compound is administered locally or systemically. The compound, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

There are further provided the various processes for preparing the compounds of formulas III-VI. Thus, for the 19,20-didehydro compounds of formula III, a process illustrated by Chart 1 comprises the steps of starting with a lactone of formula VIII and (a) transforming that starting compound to a compound of formula IX, (b) optionally oxidizing the product of step (a) to form a compound of formula XI and (c) transforming compound IX or compound XI to a compound of formula III.

For PGF$_\alpha$-type formula-III compounds wherein W is

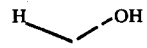

and R$_1$ is —COOR$_6$, also represented by formula X in Chart 1, the blocking groups of IX are simply removed by hydrolysis and the caboxyl group is optionally esterified. For PGE-type formula-III compounds wherein W is

and R$_1$ is —COOR$_6$, represented by formula XII in Chart 1, the same procedures are applied to XI. For PGF$_\beta$-type compounds wherein W is

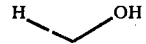

and R$_1$ is —COOR$_6$, the formula-XI compounds are reduced to a mixture of PGF$_\alpha$ and PGF$_\beta$ compounds, whereupon the PGF$_\beta$-type compounds are separated, hydrolyzed to remove blocking groups, and optionally esterified. For 9-deoxo-9-methylene-PGE compounds of formula III wherein W is

also represented by formula XIV in Chart 1, the 9-oxo group of formula-XI is transformed to a 9-methylene moiety applying the sulfoximine procedure of C. A. Johnson et al., J. Am. Chem. Soc. 95, 6462 (1973), to yield XIII and XIV.

Transformation at C-1 and C-2 to alcohol, amine, amide, or tetrazolyl groups within the scope of R$_1$ are made by methods known in the art or disclosed herein. Likewise, transformations at D, Q, and X are made by methods known in the art or disclosed herein.

For the 19-hydroxy compounds of formula IV, several processes are available. One process comprises the steps of starting with a lactone of formula XV and (a) transforming that starting material to a compound of formula XVI, (b) optionally oxidizing the product of step (a) to form a compound of formula XVII and (c) transforming compound XVI or XVII to a compound of formula IV. When the lactone starting materials of formula XV are replaced with mixed C-19(R,S) epimers of formula XVa the corresponding mixed C-19 epimeric products of formula IVa are obtained.

Another process for the mixed C-19 epimeric products of formula IVa comprises the steps of starting with a 19,20-didehydro compound of formula XVIII (a) hydroxylating it to form a compound of formula XIX and (b) transforming the product of step (a) to a compound of formula XX.

For the 19-keto compounds of formula V, a process comprises the steps of starting with a 19-hydroxy compound of formula XXI or a mixed C-19 epimeric hydroxy compound of formula XIX and (a) oxidizing either compound XXI or XIX to form a 19-keto compound of formula XXII and (b) transforming the product of step (a) to a compound of formula V.

For the 19-hydroxy-19-methyl compounds of formula VI, one process comprises the steps of starting with a lactone of formula XV or of formula XVa and (a) transforming that lactone to a compound of formula XXIII, (b) transforming the product of step (a) to a compound of formula XXIV and (c) transforming the product of step (b) to a compound of formula VI.

Still another process for the 19-hydroxy-19-methyl compounds comprises the steps of starting with a 19-keto compound of formula XXII and (a) transforming it to a compound of formula XXV and (b) transforming the product of step (a) to a compound of formula VI.

As with the formula-III compounds, the transformations of one compound to another with variations of D, Q, W, X, and, at C-1, of R$_1$ or R$_{19}$, are made for the formula-IV, —V, or —VI compounds by methods known in the art or disclosed herein, using appropriate blocking groups.

Charts 1-49, herein, illustrate the above processes and transformations. Those processes not illustrated are based on chemical procedures generally known to those skilled in the art. The steps of the charts will be discussed in detail below and further illustrated in the Examples.

With regard to Charts 2-49, examples of alkyl of one to 4 carbon atoms, inclusive, are methyl, ethyl, propyl, butyl, and isomeric forms thereof. Examples of alkyl of one to 8 carbon atoms, inclusive, are those given above and pentyl, hexyl, heptyl, octyl, and isomeric forms thereof. Examples of alkyl of one to 18 carbon atoms, inclusive, are those given above and nonyl, decyl, undecyl, dodecyl, tridecyl, tetradecyl, pentadecyl, hexadecyl, heptadecyl, octadecyl, and isomeric forms thereof. Examples of cycloalkyl of 3 to 10 carbon atoms, inclusive, which includes alkyl-substituted cycloalkyl, are cyclopropyl,
2-methylcyclopropyl,
2,2-dimethylcyclopropyl,
2,3-diethylcyclopropyl,
2-butylcyclopropyl,
cyclobutyl,
2-methylcyclobutyl,
3-propylcyclobutyl,
2,3,4-triethylcyclobutyl,
cyclopentyl,
2,2-dimethylcyclopentyl,
2-pentylcyclopentyl,
3-tert-butylcyclopentyl,
cyclohexyl,
4-tert-butylcyclohexyl,
3-isopropylcyclohexyl,
2,2-dimethylcyclohexyl,
cycloheptyl,
cyclooctyl,
cyclononyl, and
cyclodecyl.

Examples of aralkyl of 7 to 12 carbon atoms, inclusive are benzyl,
phenethyl,
1-phenylethyl,
2-phenylpropyl,
4-phenylbutyl,
3-phenylbutyl,
2-(1-naphthylethyl), and
1-(2-naphthylmethyl).

Examples of phenyl substituted with one, 2, or 3 chloro or alkyl groups of one to 3 carbon atoms, inclusive, are p-chlorophenyl,
m-chlorophenyl,
o-chlorophenyl,
2,4-dichlorophenyl,
2,4,6-trichlorophenyl,
4-chloro-2-methylphenyl,
2,4-dichloro-3-methylphenyl,
(o-, m-, or p-)tolyl,
p-ethylphenyl, and
2,5-dimethylphenyl.

Examples of phenyl substituted with hydroxycarbonyl or alkoxycarbonyl in which the alkoxy group consists of one to 4 carbon atoms, inclusive, are (o-, m-, p-)-carboxyphenyl, methyl (o-, m-, p-)-carboxyphenyl, and isopropyl (o-, m-, p-)-carboxyphenyl.

Examples of hydrocarbyl of one to 18 carbon atoms, inclusive, are any of the examples of alkyl of one to 18 carbon atoms, cycloalkyl of 3 to 10 carbon atoms, and aralkyl of 7 to 12 carbon atoms given above.

To obtain the optimum combination of biological response specificity, potency, and duration of activity, certain compounds within the scope of formulas III-VI are preferred. For example it is preferred that Q be

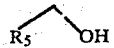

wherein it is especially preferred that $R_5$ be hydrogen or methyl.

When Q is

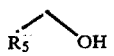

it is preferred that $R_5$ be methyl.

Another preference for the compounds of formulas III-VI, as to $R_1$, is that $R_6$ in $-COOR_6$ be either hydrogen or alkyl of one to 12 carbon atoms, inclusive, or a salt of a pharmacologically acceptable cation. Further, when $R_6$ is alkyl, it is more preferred that it be alkyl of one to 4 carbon atoms, and especially methyl or ethyl.

Still another preference for the 19-hydroxy compounds of formula-IV and VI is that the 19-hydroxy configuration be "R".

19,20-DIDEHYDRO PROSTAGLANDIN COMPOUNDS

This section will take up the procedures for preparing the formula-III 19,20-didehydro ("$\Delta^{19}$") prostaglandin compounds and intermediates illustrated by charts 1-21.

Referring to Chart 1, starting materials of formula VIII are lactones readily prepared from known materials by processes shown in Charts 2-5, and these processes will be discussed at this point. In Chart 2 the formula-XXVI aldehyde is reacted with a Grignard reagent of the formula $CH_2=CH-(CH_2)_3-Mg-Hal$ and the resulting compound XXVII is blocked to form XXVIII. The starting aldehyde XXVI is known in the art (for example see Derwent Farmdoc Abstract No. 28225W, Japanese Pat. No. 50-18460) or is available by the process shown in Chart 6, herein, and Preparation 1 (see also Derwent Farmdoc Abstract No. 56066Y, German Pat. No. 2703471).

In Chart 6, tricyclic lactone aldehyde XXIX is available from U.S. Pat. No. 3,816,462; either the exo or endo form will yield the formula-XXXII compound. In step (a) compound XXX is formed by the Wittig reaction with the ylid derived from methyltriphenylphosphonium bromide. In step (b) compound XXXI is obtained by hydroxylation. The formula-XXXII diester is then made by stepwise reaction, first using an ortho ester to form a cyclic ortho ester which is then reacted with anhydrous formic acid. Compound XXXIII is obtained in step (d) by solvolysis to remove formyl groups and, for XXXIV, free hydroxyl groups are blocked in step (e). Acyl groups of XXXIV are removed by basic solvolysis in step (f) and, finally the terminal hydroxyl groups of XXXV are oxidized to form XXXVI in step (g).

In Chart 2, and hereafter, blocking group $R_{15}$, is as defined in the Table, but preferably is tetrahydropyranyl (THP). Formula-XXVI compounds wherein $R_{15}$ is not THP are readily obtained from XXXVI of Chart 6 by replacing THP with hydrogen by mild acid hydrolysis and thereafter blocking with an appropriate form of $R_{15}$ as follows:

When the blocking group $R_{15}$ is tetrahydropyranyl (THP) or tetrahydrofuranyl, the appropriate reagent, e.g. 2,3-dihydropyran or 2,3-dihydrofuran, is used in an inert solvent such as dichloromethane in the presence of an acid condensing agent such as p-toluenesulfonic acid or pyridine hydrochloride. The reagent is used in slight excess, preferably 1.0 to 1.2 times theory, and the reaction is carried out at about 20°–50° C.

When $R_{15}$ is of the formula

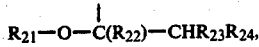

as defined herein, including 1-ethoxyethyl, the appropriate reagent is a vinyl ether, e.g. ethyl vinyl ether, isopropenyl methyl ether, isobutyl vinyl ether, or any vinyl ether of the formula $R_{21}$-OC($R_{22}$)=$CR_{23}R_{24}$ wherein $R_{21}$, $R_{22}$, $R_{23}$, and $R_{24}$ are as defined herein; or an unsaturated cyclic or heterocyclic compound, e.g. 1-cyclohex-1-yl methyl ether

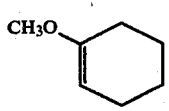

or 5,6-dihydro-4-methoxy-2H-pyran

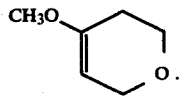

See C. B. Reese et al., J. Am. Chem. Soc. 89, 3366 (1967). The reaction conditions for such vinyl ethers and unsaturates are similar to those for dihydropyran above.

Again referring to Chart 2, if $R_5$ in $Q_1$ is alkyl, e.g. methyl, compound XXVII is oxidized with Jones reagent to form the 3'-oxo compound which is then reacted with a Grignard reagent or other appropriate organometallic reagent to introduce the alkyl group. See for example U.S. Pat. No. 3,728,382. The 3'R and 3'S isomers are separated, for example by silica gel chromatography. Compound XXVIII is then obtained by blocking.

In Chart 3 an aldehyde of formula XXXVII is used. It is available, for example when $R_{14}$ is acetyloxy, from E. J. Corey et al., J. Am. Chem. Soc. 91, 5675 (1969); when $R_{14}$ is benzoyloxy, from U.S. Pat. No. 3,778,450; when $R_{14}$ is hydrogen, see E. J. Corey et al., Tetrahedron Lett. No. 49, 4753 (1971); when $R_{14}$ is —$CH_2OR_{18}$, i.e. blocked hydroxymethyl, by blocking the hydroxymethyl-substituted lactone, for which see Derwent Farmdoc Abstract No. 12714W. In step (a), aldehyde XXXVII is reacted with a Wittig reagent derived from a phosphonate of formula CLX

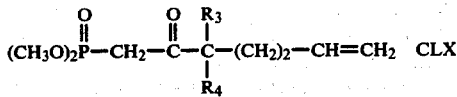

to form compound XXXVIII. For further details of the Wittig reaction see, for example, A. William Johnson, "Ylid Chemistry", Academic Press, N.Y., 1966.

For intermediates of formula XXXIX in which Q is

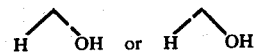

the 3'-oxo group of XXXVIII is reduced in step b, for example with zinc borohydride and the isomers are separated, for example by silica gel chromatography. The 3'α isomers are generally preferred. For intermediates in which Q is

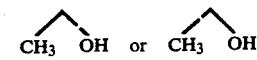

the compound XXXVIII is reacted with a Grignard reagent $CH_3MgHal$ or with trimethylaluminum and the isomers are separated by silica gel chromatography.

In step (c) the carboxyacyl blocking groups are removed by hydrolysis and hydroxyls are blocked with $R_{15}$ blocking groups such as tetrahydropyranyl to form XL.

Compounds of formula XL are within the scope of formula VIIi of Chart 1 and are accordingly useful as starting material therein. The remaining steps of Chart 3 produce compounds XLIV which correspond to formula VIII wherein X is —$CH_2CH_2$—.

In step (d) intermediate XLI is formed by hydroboration, for example with 9-borabicyclo[3.3.1]nonane ("9-BBN"), for which see Fieser et al., "Reagents for Organic Synthesis", Vol. 2, p. 31, 1969, Wiley and Sons, N.Y.

In step (e) compound XLI is reduced catalytically for example with hydrogen at atmospheric pressure over palladium on charcoal to yield XLII.

In step (f) the terminal hydroxy is mesylated or tosylated, for example, using methanesulfonyl chloride or p-toluenesulfonyl chloride in the presence of a tertiary base such as triethylamine or pyridine to yield XLIII, and finally in step (g) the olefin is restored by methods known in the art. For example, the sulfonate is reacted with the sodium derivative of phenyl selenide and the resulting phenyl selenide is oxidized with excess hydrogen peroxide. See Fieser et al., ibid, Vol. 5, p. 273, 1975. Compounds XLIV are thus obtained.

In Chart 4, the lactone XLV is obtained by photoisomerization whereby the latent $C_{13}$–$C_{14}$ double bond is isomerized from trans to cis. See for example U.S. Pat. No. 4,026,909. Compound XXXVIII is irradiated, preferably with a photon generating source producing photons of wave length about 3500 Angstroms, until an equilibrium mixture of cis and trans isomers is obtained. The progress is conveniently monitored by thin layer chromatography. The mixture is then separated by conventional methods, for example silica gel chromatography. Thereafter the 3'-oxo groups are replaced by Q in the manner described above, and the acyl groups of $R_4$ are replaced, first with hydrogen, and then with blocking groups $R_{15}$ to form the compounds of formula XLVI.

In Chart 5 the process is directed to lactones of formula LII wherein there is triple bond at latent $C_{13}$–$C_{14}$. The general procedure follows that of U.S. Pat. No. 4,029,681. The formula-XLIX mono-halo compound is obtained by halogenation of XXXVIII to yield XLVII followed by dehydrohalogenation and dehalogenation. The halogenation is conveniently done with a reagent such as N-bromosuccinimide or alternatively, a solution of bromine in carbon tetrachloride. Dehydrohalogenation proceeds by addition of a base such as pyridine or methanolic sodium acetate. Dehalogenation is achieved with the usual reagents, for example zinc-acetic acid.

Optionally the formula-XLIX mono-halo compound is prepared using lactone XXXVII of Chart 3 and a Wittig reagent derived from a 1-halophosphonate. Whereas bromo is shown in Chart 5, chloro derivatives are useful for this procedure.

The formula-L compounds are obtained by replacing the 3'-oxo group with Q, replacing acyl groups at $R_{14}$ with hydrogen, and then blocking hydroxyl groups with $R_{15}$. Thereafter formula-LI compounds are obtained by dehydrohalogenation, for example with a strong base such as potassium t-butoxide or sodium methoxide in dimethylsulfoxide or similar aprotic solvent. The formula-LII lactone results from LI on standing with a trace of acid present.

Referring now again to Chart 1, for those compounds in which D is:

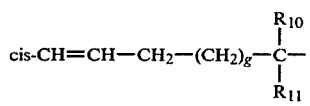

the transformation of VIII to IX and X is shown specifically in Chart 7 in the sequence VIII - LIII - LIV - LV. In Chart 7 step (a) the formula-VIII lactone is reduced to lactol LIII and thereafter that lactol is alkylated by the Wittig reaction using an ylid prepared from a phosphonium bromide of the formula

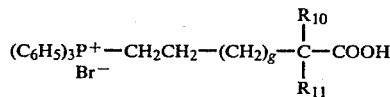

in step (b) of Chart 7 to yield LIV. Thereafter in step (c) the PGF$_{2\alpha}$-type products of formula LV are obtained by replacing blocking groups $R_{15}$ at $R_{13}$ and $Q_1$ with hydrogen and optionally esterifying the acid. When $R_{10}$ and $R_{11}$ are fluoro, for example, the products are 2,2-difluoro-19,20-didehydro-PGF$_{2\alpha}$-type compounds.

In Chart 1, the PGF$_{2\alpha}$-type products with blocking groups represented by formula IX are optionally transformed to PGE$_2$-type compounds XI using oxidizing agents and conditions which selectively oxidize secondary hydroxy groups to carbonyl groups in the presence of carbon-carbon double bonds. Oxidation reagents known in the art for this purpose include the Jones reagent, i.e. chromic acid, for which see J. Chem. Soc. 39 (1946). Thereafter the formula-XII 19,20-didehydro-PGE$_2$-type compounds are obtained by deblocking the formula-XI compounds.

The formula-XII 19,20-didehydro-PGE$_2$-type compounds are also useful for preparing PGF$_{2\beta}$-type compounds within the scope of formula III by the general method of carbonyl reduction as is known in the art. See for example U.S. Pat. No. 3,796,743 or Bergstrom et al., Acta Chem. Scand. 16, 969 (1962). Any reducing agent is used which does not react with carbon-carbon double bonds or ester groups. Preferred reagents are lithium (tri-tert-butoxy) aluminum hydride, the metal borohydrides, e.g., sodium, potassium and zinc borohydrides and metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See for example, Bergstrom et al., cited above, Granstrom et al., J. Biol. Chem. 240, 457 (1965), and Green et al., J. Lipid Research 5, 117 (1964). Especially preferred as separation methods are column or partition chromatography procedures, both normal and reversed phase, preparative thin layer chromatography, and countercurrent distribution procedures.

Again following Chart 1, 9-deoxy-9-methylene-19,20-didehydro-PGE$_2$ compounds of formula XIV are obtained from the formula-XI compounds using procedures known in the art. See for example U.S. Pat. No. 3,950,363, applying the procedure of C. A. Johnson et al., J. Am. Chem. Soc. 95, 6462 (1973). Here the carbanion of a sulfoximine of the formula

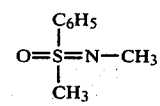

generated, for example, with an alkyllithium or an alkylmagnesium halide, is reacted with the formula-XI compound to form a sulfonimidoyl adduct of formula LVI. Thereafter reductive elimination with, for example aluminum amalgam in the presence of acids such as acetic acid or hydrochloric acid yields the formula-XIV products, generally free of the blocking groups. If formula-XIII compounds are present they are readily hydrolyzed in the known way to remove blocking groups $R_{15}$.

Other formula-III 19,20-didehydro compounds within the scope of D are prepared by the processes of charts 8-15. When D is cis—CH$_2$—CH=CH—CH$_2$—CH$_2$—, reference is made to chart 8. See also U.S. Pat. No. 3,933,889. Lactol LIII is transformed to enol ether LVII, for example by reaction with hydrocarbyloxymethylenetriphenylphosphorane of the formula (C$_6$H$_5$)$_3$P=CH—OR$_{17}$, although $R_{17}$ is preferably alkyl of one to 4 carbon atoms, inclusive. See, for example, S. G. Levine, J. Am. Chem. Soc. 80, 6150 (1958). The reagent is conveniently prepared from a corresponding quaternary phosphonium halide and a base, e.g. butyllithium or phenyllithium at a low temperature, such as below −10° C. Methoxymethylenetriphenylphosphonium chloride is particularly useful. Various other hydrocarbyloxymethylenetriphenylphosphoranes are useful for preparing the formula-LVII intermediates, wherein $R_{17}$ is hydrocarbyl, including alkoxy (of 1 to 4 carbon atoms)-, aralkoxy-, cycloalkoxy-, and aryloxymethylenetriphenylphosphoranes. Examples of these hydrocarbyloxymethylenetriphenylphosphoranes are 2-methylbutoxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropoxy-, cyclohexyloxy-, phenoxy-, and p-methylphenoxymethylenetriphenylphosphorane. See for example Organic Reactions Vol. 14, pages 346–348, John Wiley and Sons, Inc., N.Y. (1965).

Consider next step (b) of Chart 8 wherein the formula-LVII enol ether intermediates are hydrolyzed to the formula-LVIII lactols. This hydrolysis is done under acidic conditions for example with perchloric acid or acetic acid in tetrahydrofuran. Reaction temperatures of 10° C. to 100° C. may be employed.

Finally in step (c) of Chart 8, the formula-LIX compounds are obtained by the Wittig reaction using the ylid derived from 3-carboxypropyltriphenylphosphonium halide and sodio methylsulfinylcarbanide. Dimethyl sulfoxide is conveniently used as a solvent, and the reaction may be done at about 25° C. Thereafter the blocking groups are removed by mild acid hydrolysis to yield the $\Delta^4$ products of formula LIX.

Compounds of formula III wherein D is —(CH$_2$)$_3$—(CH$_2$)$_g$—CH$_2$— are prepared by the process of Chart 9. The enone compound LX is available by the steps of Chart 10. In Chart 10 the starting compound is a lactone of formula VIII blocked at $R_{13}$ and $Q_1$, for which see the same formula-VIII compound discussed above for chart 1 and related charts 2-5. In step (a) of Chart 10 the triol acid of formula LXVIII is formed by hydrolysis, opening the lactone ring. The hydrolysis occurs in a solvent containing water, for example, in methanol, dioxane, or tetrahydrofuran, in the presence of a base, such as an alkali metal hydroxide or carbonate, preferably sodium hydroxide. The reaction occurs in the range of about 0° to 100° C. and is conveniently done at ambient conditions. In this, as in all steps described herein, the duration of the reaction is determined most readily by following it with TLC. During this step the blocking groups $R_{15}$ are not removed.

In step (b) silylated compound LXIX is obtained from LXVIII by procedures known in the art or described herein. See, for example, Pierce, "Silylation of Organic Compounds", Pierce Chemical Co., Rockford, Illinois (1968). The necessary silylating agents for these transformations are known in the art or are prepared by methods known in the art. See, for example, Post, "Silicones and Other Organic Silicon Compounds", Reinhold Publishing Corp., New York, N.Y. (1949). These reagents are used in the presence of a tertiary base such as pyridine at temperatures in the range of about 0° to +50° C. Examples of trisubstituted monochlorosilanes suitable for this purpose include
chlorotrimethylsilane,
chlorotriisobutylsilane,
tert-butyldimethylchlorosilane,
chlorotriphenylsilane,
chlorotris(p-chlorophenyl)silane,
chlorotri-m-tolylsilane, and
tribenzylchlorosilane. Alternately, a chlorosilane is used with a corresponding disilazane. Examples of other silylating agents include
pentamethylsilylamine,
pentaethylsilylamine,
N-trimethylsilyldiethylamine,
1,1,1-triethyl-N,N-dimethylsilylamine,
N,N-diisopropyl-1,1,1-trimethylsilylamine,
1,1,1-tributyl-N,N-dimethylsilylamine,
N,N-dibutyl-1,1,1-trimethylsilylamine,
1-isobutyl-N,N,1,1-tetramethylsilylamine,
N-benzyl-N-ethyl-1,1,1-trimethylsilylamine,
N,N,1,1-tetramethyl-1-phenylsilylamine,
N,N-diethyl-1,1-dimethyl-1-phenylsilylamine,
N,N-diethyl-1,1-dimethyl-1-phenylsilylamine,
N,N-diethyl-1-methyl-1,1-diphenylsilylamine,
N,N-dibutyl-1,1,1-triphenylsilylamine, and
1-methyl-N,N-1,1-tetraphenylsilylamine.

Although a wide variety of silylating agents are available, it is preferred that the silyl groups on the ring contain at least one hindered group, for example:
isopropyl,
secondary butyl,
tert-butyl,
cyclohexyl, or
phenyl. The silyl groups with hindered substituents are characterized as being less susceptible to hydrolysis than, for example, trimethylsilyl, and therefore resistant to replacement during subsequent steps, particularly step (d). Examples of preferred silyl groups for the cyclopentane ring are:
isopropyldimethylsilyl,
sec-butyldimethylsilyl,
tert-butyldimethylsilyl,
triisopropylsilyl,
cyclohexyldimethylsilyl, and
triphenylsilyl. In addition to the silylation methods discussed above, it is advantageous to silylate with a chlorosilane in the presence of imidazole in a solvent such as dimethylformamide. See Corey et al., J. Am. Chem. Soc. 94, 6190 (1972). The temperature range for the reaction is about −10° to +80° C.

In step (c) the formula-LXX compound is obtained by selective hydrolysis of silyl from the terminal carboxyl group. Generally an alkali metal carbonate is employed in water and a cosolvent such as methanol, tetrahydrofuran or dioxane, in a temperature range of about −10° to +100° C. If the silyl group on the ring is hindered, a stronger base such as sodium hydroxide may be used to selectively remove the silyl group from the carboxyl.

In step (d), oxidative decarboxylation is employed to yield the formula-LXXI compound. See J. D. Bacha and J. K. Kochi, Tetrahedron, 24, 2215 (1968). Compound LXX is treated in solution, for example in benzene, toluene, xylene, or heptane, with a copper (II) salt such as the acetate, chloride, or nitrate, solubilized with a compound such as pyridine, followed by a lead (IV) salt such as the acetate or benzoate. Decarboxylation may be done either thermally (60°-100° C.) or photochemically using radiation of about 3000-3700 Å as from mercury vapor lamps, in a temperature range of about 0° to 60° C.

In step (e), the compound of formula LXXII is obtained by selective hydrolysis of the silyl groups without removing the $R_{15}$ blocking groups. For this purpose a base is used in a liquid medium such as dioxane or tetrahydrofuran. For unhindered silyl groups an alkali metal carbonate is useful; for hindered groups, such as dimethyl-t-butylsilyl, a tetra-n-alkylammonium fluoride such as tetra-n-butylammonium fluoride is preferred, in a temperature range of −10° to +50° C. See E. J. Corey et al., J. Am. Chem. Soc. 94, 6190 (1972).

In step (f) the formula-LX ketone is obtained by oxidation. Useful for this purpose is pyridinium chlorochromate, Collins reagent, and especially Jones reagent at about −40° C. to about 25° C. See J. Chem. Soc. 39 (1946). Acetone is a suitable diluent for this purpose, and a slight excess beyond the amount necessary to oxidize the hydroxy groups of the reactant is used.

Referring again to Chart 9, step (a), compound LXI is obtained by conjugative addition with a lithium diaryl cuprate reactant prepared from

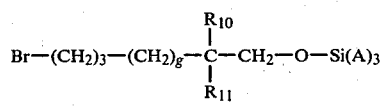

$$\text{Br}-(\text{CH}_2)_3-(\text{CH}_2)_g-\underset{\underset{R_{11}}{|}}{\overset{\overset{R_{10}}{|}}{C}}-\text{CH}_2-\text{O}-\text{Si(A)}_3$$

wherein Si(A)$_3$ is as defined above. For the synthesis of a cuprate reagent see, for example, Posner, Org. React. 19, 1 (1972) and Normant, Synthesis 63 (1972). See also Posner for typical conditions for addition to an enone. It is conveniently done in a solvent such as diethyl ether or tetrahydrofuran at about −78° C. to 0° C. A related addition has been reported by Stork et al., J. Am. Chem. Soc. 97, 4745 (1975).

In step (b) compound LXII is obtained by reduction of the ketone, using methods known in the art, for example with sodium borohydride at about 0° C. or lithium tri(sec-butyl)borohydride. The reduction yields both 9α and 9β hydroxy epimers which are separated, for example by silica gel chromatography.

In step (c) the formula-LXIII compounds are obtained from the formula-LXII compounds above by blocking free hydroxyls with $R_{18}$ carboxyacyl groups. For example, $R_{18}$ may represent an aromatic group such as benzoyl, substituted benzoyl, mono-esterified phthaloyl, naphthoyl and substituted naphthoyl, or an aliphatic group such as acetyl or pivaloyl. For introducing those blocking groups, methods known in the art are used.

Thus, an aromatic acid of the formula $R_{18}OH$, wherein $R_{18}$ is an aromatic group within the scope of $R_{18}$ as defined above, for example benzoic acid, is reacted with the formula-LXII compound in the presence of a dehydration agent, e.g. sulfuric acid, zinc chloride, or phosphoryl chloride; or an anhydride of the aromatic acid of the formula $(R_{18})_2O$, for example benzoic anhydride, is used. As examples of reagents providing $R_{18}$ for the purposes of this invention, the following are available as acids ($R_{18}OH$), anhydrides (($R_{18})_2O$), or acyl chlorides ($R_{18}Cl$): benzoyl; substituted benzoyl, e.g.

(2-, 3-, or 4-)methylbenzoyl,
(2-, 3-, or 4-)ethylbenzyl,
(2-, 3-, or 4-)isopropylbenzoyl,
(2-, 3-, or 4-)tert-butyl-benzoyl,
2,4-dimethylbenzoyl,
3,5-dimethylbenzoyl,
2-isopropyltoluyl,
2,4,6-trimethylbenzoyl,
pentamethylbenzoyl,
α-phenyl-(2-, 3-, or 4-)toluyl,
(2-, 3-, or 4-)phenethylbenzoyl,
(2-, 3-, or 4-)nitrobenzoyl,
(2,4-, 2,5-, or 3,5-)dinitrobenzoyl,
4,5-dimethyl-2-nitrobenzoyl,
2-nitro-6-phenethylbenzoyl,
3-nitro-2-phenethylbenzoyl;
mono-esterified phthaloyl, e.g.

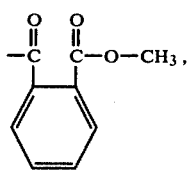

isophthaloyl, e.g.

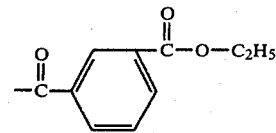

or terephthaloyl, e.g.

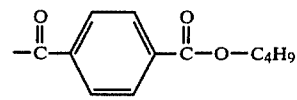

(1- or 2-)naphthoyl; and substituted naphthoyl, e.g.
(2-, 3-, 4-, 5-, 6-, or 7-)-methyl-1-naphthoyl,
(2- or 4-)-ethyl-1-naphthoyl,
2-isopropyl-1-naphthoyl,
4,5-dimethyl-1-naphthoyl,
6-isopropyl-4-methyl-1-naphthoyl,
8-benzyl-1-naphthoyl,
(3-, 4-, 5-, or 8-)-nitro-1-naphthoyl,
4,5-dinitro-1-naphthoyl,
(3-, 4-, 6-, 7- or 8-)-methyl-1-naphthoyl,
4-ethyl-2-naphthoyl, and
(5- or 8-)-nitro-2-naphthoyl.

Examples of aromatic acid anhydrides useful for this purpose are
benzoic anhydride,
(o, m, or p)-bromobenzoic anhydride,
2,4-(or 3,4)-dichlorobenzoic anhydride,
p-trifluoromethylbenzoic anhydride,
2-chloro-3-nitrobenzoic anhydride,
(o, m, or p)-nitrobenzoic anhydride,
(o, m, or p)-toluic anhydride,
4-methyl-3-nitrobenzoic anhydride,
4-octylbenzoic anhydride,
(2,3, or 4)-biphenylcarboxylic anhydride,
3-chloro-4-biphenylcarboxylic anhydride,
5-isopropyl-6-nitro-3-biphenylcarboxylic anhydride, and
(1 or 2)-naphthoic anhydride. Preferably, however, an aromatic acyl halide, for example benzoyl chloride, is reacted with the formula-LXII compound in the presence of a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess. There may be employed, therefore, benzoyl chloride, 4-nitrobenzoyl chloride, 3,5-dinitrobenzoyl chloride, and the like, i.e. $R_{18}Cl$ compounds corresponding to the above $R_{18}$ groups. If the acyl chloride is not available, it is made from the corresponding acid and phosphorus pentachloride as is known in the art.

Aliphatic carboxyacylating agents useful for this transformation are known in the art or readily obtainable by methods known in the art, and include carboxyacyl halides, preferably chlorides, bromides, or fluorides, and carboxyacid anhydrides. The preferred reagent is an acid anhydride. Examples of acid anhydrides useful for this purpose are acetic anhydride,
propionic anhydride,
butyric anhydride,
pentanoic anhydride,
nonanoic anhydride,
tridecanoic anhydride,
stearic anhydride,
(mono, di, or tri)chloroacetic anhydride,
3-chlorovaleric anhydride,
3-(2-bromoethyl)-4,8-dimethylnonanoic anhydride,
cyclopropaneacetic anhydride,
3-cycloheptanepropionic anhydride,
13-cyclopentanetridecanoic anhydride,
phenylacetic anhydride,
(2 or 3)-phenylpropionic anhydride,
13-phenyltridecanoic anhydride, and
phenoxyacetic anhydride.

In step (d) the formula-LXIII compounds are deblocked at C-1 to yield the formula-LXIV alcohols, by selective hydrolysis without removing blocking groups $R_{15}$ and $R_{18}$. For example, if $-Si(A)_3$ is tert-butyldimethylsilyl, tetra-n-butylammonium fluoride is employed.

In step (e) the formula-LXV compounds are obtained by oxidizing the terminal C-1 hydroxy groups of LXIV to carboxyl groups using methods described herein or known in the art.

In step (f) the formula-LXVI compounds are obtained by selective hydrolysis of the blocking groups, using base hydrolysis to replace acyl blocking groups $R_{18}$. For example aqueous potassium hydroxide is useful at about 25°-100° C.

Finally in step (g) the formula-LXVII $PGF_1$-type products are obtained by removing the $R_{15}$ blocking groups by mild acid hydrolysis.

The formula-LXVI compounds are useful for preparing $PGE_1$-type products following Chart 1.

Compounds of formula III where D is (trans-$(CH_2)_3$—CH1=CH— are prepared by the process of Chart 11. The starting materials of formula LXXIII are available, for example by esterifying the formula-LXVI compounds of Chart 9 and silylating at C-9. For background in preparing $\Delta^2$-prostaglandin analogs, see for example U.S. Pat. No. 4,024,174.

In step (a), selenylation is achieved by first forming 2-lithium derivatives of the formula-LXXIII compounds for example by reaction with a lithium amide formed from a secondary amine such as N-isopropylcyclohexylamine. Thereafter the formula-LXXIV compounds are obtained by reaction with diphenyldiselenide or benzeneselenyl bromide using about 3 equivalents for each molecular equivalent of the C-2 lithium derivative at about −78° C.

In step (b) the formula-LXXV $\Delta^2$ compounds are formed by oxidative elimination, for example with hydrogen peroxide or sodium periodate.

In steps (c) and (d) the blocking groups are removed stepwise. Intermediate LXXVI is useful for preparing $\Delta^2$-$PGE_1$ compounds.

Compounds of formula III wherein D is —$(CH_2)_j$—O—$(CH_2)_p$— including —$(CH_2)_3$—O—$CH_2$—, —$(CH_2)_2$—O— $(CH_2)_2$—, and —$CH_2$—O—$(CH_2)_3$—, are prepared by the process of Chart 12. The starting materials of formula LX are available from the steps of Chart 10, above. In step (a) compound LXXVIII is obtained by conjugative addition with a lithium diaryl cuprate reactant prepared from $$Br-(CH_2)_j-O-(CH_2)_p-CH_2-O-Si(A)_3$$

following the general procedure for Chart 9 above. Likewise steps (b) through (g) follow the procedures for Chart 9 described above, but proceeding here through intermediates LXXIX, LXXX, LXXXI, LXXXII, and LXXXIII to 3-, 4-, or 5-oxa-$PGF_{1\alpha}$ products represented by formula LXXXIV.

The 5-oxa-$PGF_{1\alpha}$ products are alternatively prepared by the steps of Chart 13 which yield LXXXVII. Starting materials are lactols LIII, for which see Chart 7 above. Step (a) yields alcohol LXXXV on reduction with aqueous methanolic or ethanolic sodium borohydride. Alternatively the predecessor lactone VIII of Chart 7 is reduced in one step to LXXXV for example with lithium aluminum hydride or diisobutylaluminum hydride at 0°-35° C. In step (b) the Williamson synthesis yields the formula-LXXXVI intermediates by reaction with a halobutyrate of the formula $$Hal-(CH_2)_3-COOR_9$$

or an orthoester of the formula $$Br-(CH_2)_3-C(OR_9)_3.$$

For background see U.S. Pat. No. 3,931,279, column 35. Finally in step (c) product LXXXVII is obtained by removing blocking groups $R_{15}$ by acid hydrolysis in the usual manner.

Inter-phenylene compounds of formula III wherein D is

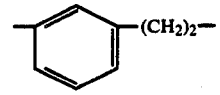

D        III        of are prepared by the process of Chart 14. The starting materials of formula LX are available from the steps of Chart 10, above. In step (a) compound LXXXVIII is obtained by conjugative addition with a lithium diaryl cuprate reactant prepared from a compound of the formula

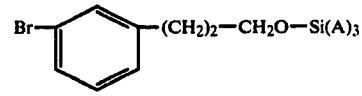

following the general procedure for Chart 9 above. Thereafter steps (b) through (g) follow the procedures for Chart 9, described above, but proceeding through intermediates LXXXIX, XC, XCI, XCII, and XCIII to the inter-phenylene end products XCIV.

The formula-XCIII compounds are useful for preparing $PGE_1$-type products following Chart 1.

Oxa-phenylene compounds of formula III wherein D is

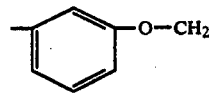

are prepared by the process of Chart 15. Here again the formula-LX starting materials are available from the steps of Chart 10 above. In step (a) compound XCV is obtained by conjugative addition with a lithium diaryl cuprate reactant prepared from a compound of the formula

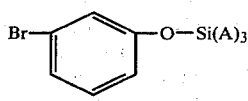

following the general procedure for Chart 9 above. Steps (b), (c), and (d) follow the procedures for similar steps (b), (c), and (d) in Chart 9 described above, but proceeding through intermediates XCVI, XCVII, and XCVIII. In step (e) the Williamson synthesis yields the formula-XCIX intermediate by reaction with a haloacetate of the formula

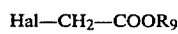

or an orthoester of the formula

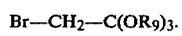

In step (f) compound C is obtained by selective hydrolysis of the acyl blocking groups, using base hydrolysis and in step (g) the $R_{15}$ blocking groups are removed by mild acid hydrolysis to yield CI.

The formula-C compounds are useful for preparing PGE$_1$-type products following Chart 1.

Referring to formula III for the 19,20-didehydro compounds disclosed herein, the preparation of compounds within the scope of D, Q, $R_2$, $R_3$, $R_4$, W, and X as defined herein has been discussed above and illustrated by Charts 1-15. Still other transformations may be accomplished by chemical processes which are known to those skilled in the art.

Charts 1-15 are generally shown to yield the acid form of the products. If a PGE-type product is obtained as an ester, the acid form is prepared by enzymatic hydrolysis using an esterase enzyme composition obtained from *Plexaura homomalla* (Esper) 1792, for which see U.S. Pat. No. 3,840,434, Oct. 8, 1974. If, as in Chart 11, a lower alkyl ester of a PGF$_1$-type intermediate or product is obtained, that ester is readily converted to the acid form by saponification. The acid is then used to prepare various esters of formula III within the scope of $R_6$ by methods known in the art. For example, the alkyl, cycloalkyl, and aralkyl esters are prepared by interaction of said acids with the appropriate diazohydrocarbon. For example, when diazomethane is used, the methyl esters are produced. Similar use of diazoethane, diazobutane, 1-diazo-2-ethylhexane, diazocyclohexane, and phenyldiazomethane, for example gives the ethyl, butyl, 2-ethylhexyl, cyclohexyl, and benzyl esters, respectively. Of these esters, the methyl or ethyl are preferred.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified, if desired, by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley & Sons, Inc., New York, N.Y., Vol. 8, pp. 389-394 (1954).

An alternative method for esterification of the carboxyl moiety of the acid compounds of formula III comprises transformations of the free acid to the corresponding silver salt, followed by interaction of that salt with an alkyl iodide. Examples of suitable iodides are
methyl iodide,
ethyl iodide,
butyl iodide,
isobutyl iodide,
tert-butyl iodide,
cyclopropyl iodide,
cyclopentyl iodide,
benzyl iodide,
phenethyl iodide,
and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters of the formula III compounds are prepared by silylating the acid to protect the hydroxy groups, for example, replacing each —OH with —O-Si—(CH$_3$)$_3$. Doing that may also change —COOH to —COO-Si—(CH$_3$)$_3$. A brief treatment of the silylated compound with water will change —COO—Si(CH$_3$)$_3$ back to —COOH. Procedures for this silylation are known in the art and are available. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—(CH$_3$)$_3$ are changed back to —OH by treatment with dilute acetic acid. Procedures for these transformations are known in the art.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See for example U.S. Pat. No. 3,984,454, German Offenlag. 2,535,693, and Derwent Farmdoc No. 16828X.

Charts 16-20 relate to transformations at C-1 for these 19,20-didehydro compounds.

When a 2-decarboxy-2-hydroxymethyl product is desired, i.e., when $R_1$ is -CH$_2$OH, the acid or lower alkyl ester form of III is reduced (see Chart 16 CII to CIII) using reagents known to reduce carboxylic acids to corresponding primary alcohols. See for example U.S. Pat. No. 4,028,419, as to lithium aluminum hydride or diisobutylaluminum hydride. Useful solvents include diethyl ether, tetrahydrofuran or dimethoxyethane. The reaction may be run at −78° C. to 100° C., although preferably at about 0° C. to 50° C. Other carbonyl groups in the molecule will also be reduced unless suitably protected as oximes, ketals, or similar carbonyl derivatives which are readily restored to carbonyls after the reduction has been accomplished.

A 2-decarboxy-2-hydroxymethyl-PGE type compound may also be prepared by blocking the C-1 alcohol groups as shown in Chart 16, formula CV. Thereafter the C-9 hydroxy is oxidized to form CVI and finally the —Si(A)₃ blocking group is removed by hydrolysis. It is preferred that —Si(A)₃ be tert-butyl-dimethylsilyl.

Compounds in which R₁ is

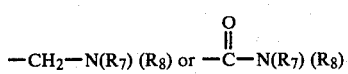

are conveniently prepared from the formula-III products which are acids, i.e. R₁ is —COOH. For background see U.S. Pat. No. 4,085,139. PGF-type compounds or 9-methylene compounds are simply converted to a mixed anhydride using an alkyl, aralkyl, phenyl, or substituted phenyl chloroformate in the presence of a tertiary amine. A preferred reagent is isobutylchloroformate. The anhydride is then reacted with ammonia or the appropriate amine (R₇)(R₈)NH to form the amide wherein R₁ is

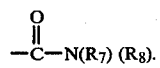

The 2-decarboxy-2-aminomethyl compound is prepared from the amide by carbonyl reduction using methods known in the art, for example lithium aluminum hydride reduction. PGE-type compounds are obtained by oxidation of the PGF-type compounds preferably when the terminal amine group is in the form of an amine salt.

In Chart 17 is shown an alternate procedure for the amine-terminated PGE-type compounds. The starting material of formula CVIII is obtained from a formula-III PGE-type compound by ketalization with ethylene glycol. For background see, for example, M. J. Cho et al., J. Medicinal Chem. 20, 1525 (1977). Anhydride CIX is formed in step (a), amide CX in step (b), and amine CXI in step (c). Finally in step (d) the ketal is hydrolysed to the PGE-type product CXII by methods known in the art. See also U.S. Pat. No. 3,915,994.

Compounds in which R₁ is

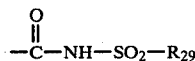

i.e. the N-sulfonylamides, are prepared from the formula-III compounds in their acid form. In Chart 18 are shown the steps by which those compounds, represented by formula CXIII, are transformed to the sulfonylamides of formula CXV. In step (a) the acid is converted to a mixed anhydride, here shown as CXIV, by reaction with isobutylchloroformate in the presence of a tertiary amine such as triethylamine. Other mixed anhydrides are also useful. In step (b) the anhydride is then reacted with the sodium derivative of a sulfonylamide of the formula Na-NH—SO₂—R₂₉ obtained for example by reaction of methanolic sodium methoxide with an equimolar amount of the sulfonylamide. The reaction of step (b) is promoted by the addition of a small amount of hexamethylphosphoramide to insure homogeneity.

Compounds in which R₁ is

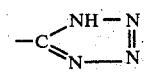

are obtained by either the process of Chart 19 or Chart 20. In Chart 19 the starting lactone LIII is available above, for example see Chart 7. Applying the Wittig reaction and using the ylid prepared from a phosphonium compound of the formula

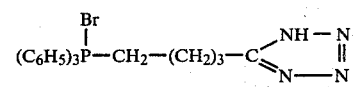

the formula-CXVI compound is obtained. See U.S. Pat. No. 3,928,391. Replacement of blocking groups R₁₅ then yields the products of formula CXVII. Optionally the CXVI compounds are transformed by methods disclosed herein or known in the art to other tetrazolyl compounds, e.g. PGE-type compounds, within the scope of formula III.

In Chart 20 the process goes stepwise from an amide to a nitrile to a tetrazolyl compound. The starting materials CXVIII are available herein, for example from an acid blocked preferentially with R₁₅ at C-11 and C-15 and converted to an amide by way of a mixed anhydride, then blocked with silyl groups at C-9.

In step (a) the formula-CXIX nitrile is prepared by dehydration of amide CXVIII with a carbodiimide. See C. Ressler et al., J. Org. Chem. 26, 3354 (1961). For example, N,N'-dicyclohexylcarbodiimide (DCC) is useful in pyridine at about room temperature.

In step (b) the tetrazolyl group in CXX is formed from the above nitrile by reaction with sodium azide and ammonium chloride in a medium such as dimethylformamide. See "Heterocyclic Compounds", R. C. Elderfield, ed., John Wiley and Sons, Inc., N.Y., Vol. 8, pages 11–12.

In steps (c) and (d) the blocking groups —Si(A)₃ and R₁₅ are replaced by desilylation and mild acid hydrolysis in the usual manner to yield CXXI and then CXXII. Compound CXXI is useful as an intermediate for preparing other tetrazolyl compounds including PGE-type products within the scope of formula III.

In Chart 21 is shown a preferred route to the 15-alkyl compounds of formula LV. In step (a) intermediate CXXIV is formed by the Grignard reaction on CXXIII using R₉MgHal or trialkylaluminum (see E. W. Yankee et al., J. Am. Chem. Soc. 96, 5865 (1974) and references cited therein). Starting material CXXIII is readily available, for example from XXXVIII of Chart 3 by steps disclosed herein or known in the art. Steps (b), (c), and (d) correspond to Chart 7, steps (a), (b), and (c) except that there need not be a blocking group at the 3' position. Products LV, mixed C-15 epimers, are separated into the 15S and 15R forms, for example by silica gel chromatography, preferably in the form of their methyl esters. The free acids are readily obtained by saponification of the methyl ester with mild alkaline conditions.

Included in the compounds of formula III are the pharmacologically acceptable salts when R₆ is a cation. Such pharmacologically acceptable salts useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are:
  methylamine,
  dimethylamine,
  trimethylamine,
  ethylamine,
  dibutylamine,
  triisopropylamine,
  N-methylhexylamine,
  decylamine,
  dodecylamine,
  allylamine,
  crotylamine,
  cyclopentylamine,
  dicyclohexylamine,
  benzylamine,
  dibenzylamine,
  α-phenylethylamine,
  β-phenylethylamine,
  ethylenediamine,
  diethylenetriamine,
and like aliphatic, cycloaliphatic, and araliphatic amines containing up to and including about 18 carbon atoms, as well as heterocyclic amines, e.g.,
  piperidine,
  morpholine,
  pyrrolidine,
  piperazine,
and lower-alkyl derivatives thereof, e.g.
  1-methylpiperidine,
  4-ethylmorpholine,
  1-isopropylpyrrolidine,
  2-methylpyrrolidine,
  1,4-dimethylpiperazine,
  2-methylpiperidine,
and the like, as well as amines containing water-solubilizing or hydrophilic groups, e.g., mono-, di-, and triethanolamine,
  ethyldiethanolamine,
  N-butylethanolamine,
  2-amino-1-butanol,
  2-amino-2-ethyl-1,3-propanediol,
  2-amino-2-methyl-1-propanol,
  tris(hydroxymethyl)aminomethane,
  N-phenylethanolamine,
  N-(p-tert-amylphenyl)diethanolamine,
  galactamine,
  N-methylglycamine,
  N-methylglucosamine,
  ephedrine,
  phenylephrine,
  epinephrine,
  procaine,
and the like.

Examples of suitable pharmacologically acceptable quaternary ammonium cations are tetramethylammonium, tetraethylammonium, benzyltrimethylammonium, phenyltriethylammonium, and the like.

Salts containing pharmacologically acceptable cations are prepared from the final formula-III compounds in free acid form, i.e. wherein $R_1$ is —COOH, by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salts to be prepared. In the case of the inorganic salts, it is usually suitable to dissolve the formula-III acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired. Amine and quaternary ammonium salts are prepared by similar methods using appropriate solvents.

19-HYDROXY PROSTAGLANDIN COMPOUNDS

This second section will disclose the procedures for preparing the formula-IV 19-hydroxy prostaglandin compounds and intermediates illustrated by Charts 22-28.

Referring to Chart 22, there is shown a simple method of forming (19R,S)-19-hydroxy-PGF's, i.e., mixed 19R and 19S isomers. The 19,20-didehydro-PGF compounds of formula CXXVII are available by the methods described in the section above. The olefin is hydrated by oxymercuration-demercuration using mercuric acetate and sodium borohydride for which see Fieser et al., Reagents for Organic Syntheses, Vol. II, 1969, p. 265. The oxymercuration is done conveniently at about 25° C., after which the mercury is removed by reduction with sodium borohydride, preferably at below 10° C. to minimize side reactions.

In Chart 23, (19R,S)-19-hydroxy prostaglandin compounds are also made by the processes disclosed, but here the approach is through a (19R,S)-19-hydroxy lactone of formula CXXIX. The formula-VIII 19,20-didehydro starting lactones are available by the methods describd in the section above. Oxymercuration-demercuration in step (a) followed by blocking the $R_{15}$ in step (b) then yields CXXIX, which is converted to CXXX and CXXXI by methods known in the art or described herein. The PGE-type compounds of formula CXXXIII are obtained by oxidizing the formula-CXXX compounds at C-9 to form CXXXII, thereafter removing blocking groups.

Chart 24 illustrates the preparation of other (19R,S)-19-hydroxy compounds, including 2-decarboxy-2-hydroxymethyl compounds of formulas CXLII, CXLIV, and CXLV. Chart 24 illustrates the reduction of carboxylate esters to the hydroxymethyl function and also the reduction of ethylenic unsaturation at C-5 and C-13. The formula-CXXXIV 19,20-didehydro starting materials are available from methods described in the section above. See for example the corresponding acids LIV of Chart 7 which are readily esterified to these lower alkyl esters.

In step (a) the silylated compound CXXXV is formed by the usual silylation reactions, for which see the description for Chart 9 above. Of the various silyl groups, dimethyl-t-butylsilyl is preferred. In step (b) the terminal olefinic group is hydrated by oxymercuration-demercuration to yield the mixed (19R)- and (19S)-19-hydroxy isomers. In step (c) catalytic hydrogenation over palladium yields a mixture of the $PGF_{1\alpha}$ and 13,14-dihydro-$PGF_{1\alpha}$ compounds, indicated in formula CXXXVII by a solid and a broken line at $C_{13}$-$C_{14}$. In step (d), 19-hydroxyls are blocked, for example with THP. In step (e) the ester is reduced to carbinol CXXXIX using for example, lithium aluminum hydride. In step (f) the newly-formed hydroxyls are blocked, for example with THP. In step (g) the CXL compounds are desilylated to the CXLI compounds, for example with a tetra-n-alkylammonium fluoride as described above for Chart 9. In step (h) deblocking, as in dilute acid, yields the PGF-type compounds of formula CXLII which are separated by silica gel chromatography. In step (i) the blocked PGF-type compounds CXLI are oxidized by the usual methods to the CXLIII PGE-type compounds which are deblocked and separated in step (j) to yield CXLIV and CXLV.

If only the PGF-type compounds of formula CXLII are desired, the process is simplified according to Chart 25. In step (a) the 19,20-didehydro starting material CXLVI is hydrated by oxymercuration-demercuration to yield CXLVII. Catalytic hydrogenation then yields CXLVIII, together with the 13,14-dihydro compound. CXLVIII is separated and reduced to CXLIX with lithium aluminum hydride and finally in step (d) the blocking groups are replaced with hydrogen using mild acid hydrolysis.

19-Hydroxy compounds having specific configuration at C-19 are obtained in several ways. Chart 26, herein, illustrates the use of a Grignard reagent prepared from one of the isomers of CLI. For details on the resolution of the (±)-1-penten-4-ol as its phthalate ester via the brucine salt see J. C. Sih, Prostaglandins, Vol. 13, No. 5, pp. 831–835 (1977). The starting material XXVI is available, for which see the discussion above for Chart 2. In step (a) the formula-CLII lactone is readily obtained using the Grignard reagent identified above. Other formula-CLIII lactones having the various forms of Q, are prepared by methods known in the art including blocking, or, when $Q_1$ includes 3'-alkyl substitution, forming the 3'-oxo compound by oxidation thereafter applying the Grignard reaction as for Chart 2 above.

Chart 27 shows the steps for forming other lactones, which together with the formula-CLIII lactones of Chart 26 above are useful for preparing 19-hydroxy prostaglandins by the processes of Chart 28.

In Chart 27, the formula-XXXVII starting aldehydes are available, as shown above for Chart 3. In step (a) the Wittig reaction is employed using the ylid derived from a phosphonate of formula CLXI. In preparing 19-hydroxy end products having specific configuration at C-19 the appropriate optically active isomer of CLXI is used. Preferably that isomer is used which yields an end product having highest pharmacological activity as determined by standard biological tests.

Various methods are available for obtaining optically active isomers of CLXI. Preferably the phosphonate is prepared from dimethyl methylphosphonate and an optically active methyl ester of a corresponding 5-hydroxy-hexanoic acid, suitably blocked with $R_{15}$. Such hexanoic acids are available in resolved state by application of the phthalate ester-brucine salt procedure of Sih cited above. Thus, for example the methyl ester of 5-hydroxy-hexanoic acid is esterified with phthalic acid and the half-ester thus formed is resolved via its brucine salt by fractional crystallization. Thereafter the acid is recovered and converted to the methyl ester and thence to the phosphonate. Other 2-substituted-5-hydroxy-hexanoic acids are known or available to those skilled in the art. For example when $R_3$ and $R_4$ are methyl, the methyl ester of 2,2-dimethyl-5-oxo-hexanoic acid is reduced. When $R_3$ and $R_4$ are fluoro, the methyl ester of 5-hydroxy-2-oxo-hexanoic acid is fluorinated, for example with molybdenum hexafluoride-boron trifluoride. See U.S. Pat. No. 3,962,293. These acids are resolved in the same manner as described above and thereafter converted to phosphonates.

Still another method of obtaining the optically active 5-hydroxy-hexanoic acids is by starting with an optically active ω-halopentan-2-ol, for example Br-$(CH_2)_3$-CH(OH)-$CH_3$, blocking the hydroxyl for example with THP, then forming a Grignard reagent and reacting it with carbon dioxide following Organic Synthesis, Coll. Vol. 1, 2nd ed., 1948, H. Gilman, editor, John Wiley, N.Y.

Continuing with Chart 27, in steps (b), (c), and (d), the 3'-oxo group of CLIV is reduced, the $R_{14}$ carboxyacyl blocking groups are replaced first with hydrogen and then with $R_{15}$ blocking groups, and all other free hydroxyl groups such as at Q are also blocked to yield the formula-CLVI intermediate. Conversion of the trans—CH=CH— olefinic group to cis—CH=CH—, to acetylenic —C≡C—, or to ethylenic —$CH_2CH_2$— is accomplished by adaptation of the procedures discussed above for Charts 3, 4, and 5.

In Chart 28 the steps leading to products CLXIV, CLXVI, and CLXVIII are shown. The starting materials CLXII include CLIII of Chart 26 and CLVI, CLVII, CLVIII, and CLIX of Chart 27, and the general procedures described above for Chart 1 are used.

19-KETO PROSTAGLANDIN COMPOUNDS

This third section will disclose the procedures for preparing the formula-V 19-keto prostaglandin compounds illustrated by Charts 29–33.

Referring to Chart 29, the formula-CXXXVI 19-hydroxy compounds of Chart 24 are oxidized to 19-keto compounds. Suitable blocking at C-9, C-11, and C-15 hydroxyls protects those hydroxyls from oxidation when preparing 19-keto-PGF-type compounds of formula CLXX. In preparing 19-keto-PGE-type compounds of formula CLXXIII, both C-9 and C-19 hydroxy groups are preferably oxidized in one step, using for example the Jones Reagent at about −35° C.

Chart 30 shows a series of similar reactions for preparing the more general compounds of formula CLXXVII and CLXXX. The starting materials of formula IX are available from Chart 1 above. The formula-CLXXV mixed (19R,S) or (±) 19-hydroxy compounds may be replaced with either the (19R) or (19S) compounds available, for example, from Chart 28 above.

Chart 31 shows a sequence of steps for preparing 2-decarboxy-2-hydroxymethyl-19-keto-$PGE_1$ compounds. The formula-CXLIX starting compounds are available from Chart 25 above. In step (a) the C-1 hydroxy groups are preferentially blocked by silyl. In step (b) the C-9 and C-19 hydroxyls are oxidized, for example with Collins reagent. In step (c) the blocking groups are replaced with hydrogen in the usual way, and the resulting product CLXXXIII and hemiacetal CLXXXIV separated by silica gel chromatography for example. The hemiacetal is converted to the 19-keto compound by mild acid, as in acetic acid-water-tetrahydrofuran.

Chart 32 illustrates a process for broadly-defined 2-decarboxy-2-hydroxymethyl-19-keto-PGE compounds of formula CXCI. The starting materials CLXXXV are readily available, for example by esterification and silylation of CLXXV of Chart 30 above. Procedures for each step have already been described. Thus, for step (a) the reduction of the ester to carbinol CLXXXVI follows that for step (e) of Chart 24. Intermediate CLXXXVIII is also a convenient source of 19-hydroxy products CLXXXIX.

Chart 33 shows steps leading to 2-decarboxy-2-hydroxymethyl-19-keto-PGF compounds of formula CXCVI utilizing previously discussed procedures for each transformation. The starting materials CXCII are readily available, for example by esterification and blocking of IX of Chart 1.

19-HYDROXY-19-METHYL PROSTAGLANDIN COMPOUNDS

This fourth section will disclose the procedures for preparing formula-VI 19-hydroxy-19-methyl prostaglandin compounds illustrated by Charts 34–49.

Referring to Chart 34, there are shown the process steps from lactone CXXIX to end products CCI and CCIII. Starting materials of formula CXXIX are available from Chart 23 above. In step (a) the hydroxyls are oxidized to keto groups, for example with Jones reagent. In step (b) the tertiary carbinol is formed, either with methylmagnesium halide or trimethylaluminum. Step (c) is the transformation to a lactol and step (d) is Wittig alkylation using an ylid as described above for Charts 1 and 7. Removal of blocking groups yields PGF compounds CCI; oxidation of hydroxyls of CC at C-9 leads to PGE-type compounds CCII and CCIII.

Chart 35 illustrates the transformation of 19-keto compounds in general, suitably blocked, to 19-hydroxy-19-methyl compounds. For the acids, trimethylaluminum in benzene is the preferred reagent in step (a); for esters, the Grignard reagent is useful. The formula-CCV and -CCVII intermediates are useful for making the formula-CCVI, -CCVIII, and -CCX products, applying the general procedures discussed above for Chart 1.

Referring to generic formula VI for the 19-hydroxy-19-methyl compounds, other compounds within the scope of D are available not only by the processes of Chart 35 but by the processes of Charts 36–45.

Chart 36 shows the reduction of the olefinic group in the "upper" (carboxy-terminated) side chain. For this purpose hydrogenation in the presence of palladium catalyst is useful. Thereafter products CCXIII and CCXV are obtained.

When D is cis—$CH_2$—$CH=CH$—$CH_2$—$CH_2$—, the steps of Chart 37 are useful. Lactol CXCIX is available from Chart 34 above. Thereafter steps (a), (b), and (c), following the procedures described above for Chart 8, yield product CCXVIII.

Compounds of formula VI ($\Delta^2$ compounds) wherein D is trans-$(CH_2)_3$—$CH=CH$— are prepared by the process of Chart 38. Starting materials CCXIX are available from a formula-CCIV compound (Chart 35) wherein D is trimethylene by reduction of the carboxyl group to hydroxymethyl, for example with lithium aluminum hydride. Aldehyde compound CCXX is obtained by oxidation of the —$CH_2OH$ of CCXIX to —CHO, using for example Collins reagent (pyridine —$CrO_3$) at about 0°–10° C. In step (b) the Wittig reaction is used, with an ylid obtained from $(CH_3O)_2$-$P(O)CH_2COOH$. See for example Derwent Farmdoc Abstract No. 50715V. Blocking groups are removed in step (c) in the conventional way to form CCXXII.

Chart 39 represents an alternate process to $\Delta^2$ compounds, via selenylation-deselenylation, applying the procedures described for Chart 11 above. Starting material CCXXIII is available herein, for example from CCXII of Chart 36. It is immaterial whether C-19 hydroxyls are blocked or not. Blocking at C-9 may be either with $R_{15}$ or silyl. Accordingly steps (a), (b), and (c) yield products CCXXVI.

The 3- and 4-oxa compounds are obtained by the processes of Charts 40 and 41. Those general procedures are known in the art, see for example U.S. Pat. No. 3,944,593. Compounds CCXXXI and CCXXXVIII are formed thereby.

The 5-oxa compounds of formula CCXLI are prepared by the steps of Chart 42. The procedures have been described above for Chart 13.

Inter-phenylene compounds of formula CCL are obtained by the procedures of Chart 43 starting with the intermediates of formula CCXLIII. Those intermediates are shown as the products of Chart 44 starting with lactone CXCVIII of Chart 34 and applying the general procedures of Chart 10 above.

Oxa-phenylene analogs of formula CCLXV are produced by the steps of Chart 45, starting with intermediates CCXLIII and following the general procedures of Chart 15 above.

Where the above processes yield an acid, the esters are prepared by any of the methods described for the 19,20-didehydro compounds above. Likewise esters are transformed to acids by processes known or described herein.

Charts 46–49 relate to transformations at C-1 for these 19-hydroxy-19-methyl compounds.

Formula-CCLXXI 2-decarboxy-2-hydroxymethyl compounds of Chart 46 are obtained by the general procedures described for Chart 16 above.

Amides of formula CCLXXIV and 2-decarboxy-2-amino methyl compounds of formula CCLXXV in Chart 47 are prepared following the general procedures of Chart 17 above. N-Sulfonylamides in which $R_1$ is

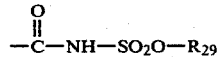

are prepared as described for the 19,20-didehydro compounds above.

Tetrazolyl-terminated compounds of formula CCLXXVIII and CCLXXXII are obtained according to Charts 48 and 49 applying the procedures of Charts 19 and 20 above.

Compounds of formulas IV–VI which are not specifically illustrated or exemplified herein are obtained by transformations using chemical processes disclosed herein or known to those skilled in the art.

For example the transformation of $R_5$ in Q from hydrogen to methyl at C-15 requires the intermediate 15-oxo compound prepared by oxidation, followed by alkylation with Grignard $R_5MgHal$ or trimethylaluminum, and subsequent separation of the 15$\alpha$ and 15$\beta$ products, for example by chromatography, preferably of the methyl esters. Preparation of esters and salts and various modifications at C-1, e.g., amides and sulfonamides follow the general procedures discussed for the formula-III 19,20-didehydro compounds.

It should be understood that many of the intermediates disclosed herein are useful not only for the purposes shown but also for many of the above transformations as known in the art.

The products formed from each step of the process are often mixtures, and, as known to one skilled in the art, may be used as such for a succeeding step or, optionally, separated and purified by conventional methods of fractionation, liquid extraction, and the like, before proceeding. It is intended that compounds are claimed not only in their purified form but also in mixtures, for example the formula-IV 19-hydroxy compounds in their mixed (R,S) form.

DESCRIPTION OF THE PREFERRED EMBODIMENTS

The invention is further illustrated by, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60, A-60D, T-60 or XL-100 spectrophotometer in deuterochloroform solution with tetramethylsilane as an internal standard.

Mass spectra are recorded on a Varian Model MAT CH7 Mass Spectrometer, a CEC Model 110B Double Focusing High Resolution Mass Spectrometer, or a LKB Model 9000 Gas Chromatograph-Mass Spectrometer (ionization voltage 22 or 70 ev.), and samples are usually run as TMS (trimethylsilyl) derivatives.

"Brine", herein, refers to an aqueous saturated sodium chloride solution.

"Celite ®" is a calcium aluminosilicate, useful as a filter aid.

"Collins reagent" is chromium trioxide in pyridine, See Tetrahedron Lett. p. 3363 (1968).

"DIBAL", herein, refers to diisobutylaluminum hydride.

"Florisil ®", herein, is a chromatographic magnesium silicate produced by the Floridin Co. See Fieser et al., "Reagents for Organic Synthesis" p. 393 John Wiley and Sons, Inc., New York, N.Y. (1967).

"HPLC", herein, refers to high pressure liquid chromatography.

"Jones reagent" is chromic acid, see J. Chem. Soc. p. 39 (1946).

"$R_f$" herein, refers to the measurement, in thin layer chromatography, of the movement of the sample spot relative to that of the solvent front, on silica gel plates unless specified, and in a solvent system that is identified.

"Skellysolve B", herein, refers to mixed isomeric hexanes.

"THP", herein, refers to tetrahydropyran-2-yl.

"TLC", herein, refers to thin layer chromatography.

"Concentrating", as used herein, refers to concentration under reduced pressure, preferably at less than 50 mm. and at temperatures below 35° C.

"Drying", as used herein, refers to contacting a compound, in solution, with an anhydrous aagent such as sodium sulfate or magnesium sulfate to remove water and filtering to remove solids.

Silica gel chromatography, as used herein, is understood to include elution, collection of fractions, and combination of those fractions shown by TLC to contain the desired product free of starting materials and impurities.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 247 (1966).

PREPARATION 1

5α-Hydroxy-3α-tetrahydropyran-2-yloxy-2β-(trans-2-formylethenyl)-1α-cyclopentaneacetic Acid, γ-Lactone (Formula XXXVI)

Refer to Chart 6. The title compound is obtained in seven steps starting with the formula-XXIX tricyclic lactone aldehyde, for which see U.S. Pat. No. 3,816,462.

a. Exo-3-hydroxy-endo-6-vinyl-bicyclo[3.1.0]-hexanexo-2-acetic acid, γ-lactone (Formula XXX). A solution of the formula-XXIX tricyclic lactone aldehyde (20 g.) in 150 ml. of benzene is treated at 5°-10° C. with a solution of the ylid prepared from methyltriphenylphosphonium bromide (54 g.) and 95 ml. of 1.6 M butyllithium in one liter of benzene (previously heated at reflux for one hr. and cooled). The addition is completed within 1-1.5 hr., and, after an additional 0.5 hr. stirring, the mixture is filtered and concentrated. The residue is taken up in 100-200 ml. of ethyl acetate-Skellysolve B (40:60) and left standing to crystallize out the by-product triphenylphosphine oxide. After filtration, the filtrate is subjected to silica gel chromatography, eluting with ethyl acetate-Skellysolve B (40:60). There is obtained the formula-XXX compound, 16.2 g., an oil, having NMR peaks at 1.3-3.0, 4.6-4.9, and 5.0-5.4δ; and $R_f$ 0.74 (in ethyl acetate-Skellysolve B (50-50)).

b. Endo-6-(1,2-dihydroxyethyl)-exo-3-hydroxy-bicyclo[3.1.0]-hexen-exo-2-acetic acid, 3-lactone (Formula XXXI). A solution of the formula-XXX alkene (step a, 8.0 g.) in 80 ml. of acetone is treated with a solution of N-methylmorpholine oxide dihydrate (9.0 g.) in 12 ml. of water, followed by a solution of osmium tetroxide (130 mg.) in 6.5 ml. of t-butanol. When the reaction is completed, the acetone is removed under reduced pressure. The residue is diluted with 100 ml. of water, saturated with ammonium sulfate, and extracted with tetrahydrofuran. The organic phase is dried over magnesium sulfate and concentrated under reduced pressure to yield 12 g. of crude oily product. The oil is subjected to silica gel chromatography to yield the formula-XXXI compound, 8.5 g., an oil, having NMR peaks at 0.7-1.2, 1.3-1.9, 2.4-3.4, 3.4-3.7, 3.7-4.2, and 4.7-5.0δ; $R_f$ 0.66 (in methanoldichloromethane (15:85)).

c. 3α-Formyloxy-5α-hydroxy-2β-(3-propionyloxy-trans-1-propenyl)-1α-cyclopentaneacetic acid, γ-lactone (Formula XXXII). A solution of the formula-XXXI glycol (step b, 7.2 g.) and triethyl orthopropionate (15 g.) in 30 ml. of tetrahydrofuran is treated with 3 μl of trifluoroacetic acid. After one hr. the solvent is removed under reduced pressure and the residue treated with 100 ml. of anhydrous formic acid with stirring. After 15 min. there is added 100 ml. of 1 N. sodium hydroxide and 100 ml. of crushed ice. The mixture is extracted with dichloromethane and the organic phase is washed with 5% aqueous sodium bicarbonate, dried over magnesium sulfate, and concentrated. The oil (9.6 g.) thus obtained is subjected to silica gel chromatography, eluting with ethyl acetatecyclohexane (1:1), to yield the formula-XXXII compound, 4.1 g., having NMR peaks at 1.1, 1.9–3.0, 4.4–4.6, 4.8–5.2, 5.6–5.8, and 8.0δ; and R$_f$ 0.49 (in ethyl acetate-cyclohexane (1:1)).

d. 3α,5α-Dihydroxy-2β-(3-propionyloxy-trans-1-propenyl)-1α-cyclopentaneacetic acid, γ-lactone (Formula XXXIII). A solution of the formula-XXXII formate (step c, 4.1 g.) in 35 ml. of dry methanol is treated with sodium bicarbonate (0.5 g.). When the reaction is finished in about 2–3 hr., the solvent is removed under reduced pressure. The residue is partitioned between water and dichloromethane, and the organic phase is dried over magnesium sulfate and concentrated. The oily residue is subjected to silica gel chromatography, eluting with ethyl acetate to yield the formula-XXXIII compound, 2.8 g., having NMR peaks at 1.13, 3.7–4.3, 4.3–4.7, 4.7–5.2, and 5.5–5.8δ; and R$_f$ 0.65 (in ethyl acetate).

e. 3α-Tetrahydropyran-2-yloxy-5α-hydroxy-2β-(2-propionyloxy-trans-1-propenyl)-1α-cyclopentaneacetic acid, γ-lactone (Formula-XXXIV). A solution of the formula-XXXIII 5-hydroxy lactone (step d, 2.8 g.) in 10 ml. of dichloromethane is treated with 5 ml. of dihydropyran and 5 mg. of p-toluenesulfonic acid dissolved in 1 ml. of tetrahydrofuran. After the reaction is finished, in about 0.5 hr., the mixture is washed with 5% aqueous sodium bicarbonate. The organic phase is dried over sodium sulfate and concentrated. The residue is subjected to silica gel chromatography, eluting with ethyl acetate-Skellysolve B (60:40) to yield the formula-XXXIV compound.

f. 3α-Tetrahydropyran-2-yloxy-5α-hydroxy-2β-(3-hydroxy-trans-1-propenyl)-1α-cyclopentaneacetic acid, γ-lactone (Formula-XXXV). The formula-XXXIV propionate, (step e, 3.0 g.) in 10 ml. of methanol is added to a solution of sodium methoxide (freshly prepared from 20 mg. of sodium in 40 ml. of anhydrous methanol). After the reaction is complete, in about 20 min., the methanol is removed under reduced pressure. The residue is partitioned between dichloromethane and 0.4 M phosphate buffer of pH 4.5. The organic phase is dried over sodium sulfate and concentrated to yield the formula-XXXV compound.

g. 3α-Tetrahydropyran-2-yloxy-5α-hydroxy-2β-(trans-2-formylethenyl)-1α-cyclopentaneacetic acid, γ-lactone (Formula XXXVI). An oxidizing reagent is prepared from chromium trioxide (5.4 g.) and 3,5-dimethylpyrazole (5.2 g.) in 150 ml. of dichloromethane, stirred for 15 min. To the solution is then added the formula-XXXV 3-hydroxy compound (step f, 1.8 g.) dissolved in 20 ml. of dichloromethane. After the reaction is finished, in about 5 min., the mixture is washed with 5% aqueous bicarbonate. The organic phase is dried over sodium sulfate and concentrated. The residue is subjected to silica gel chromatography, eluting with acetone-dichloromethane (1:9) to yield the formula-XXXVI compound.

EXAMPLE 1

3α,5α-Dihydroxy-2β-[(3R,S)-3-hydroxytrans-1,7-octadienyl]-1α-cyclopentaneacetic Acid γ-Lactone, 3-tetrahydropyran-2-yl ether and also 3,3'-bis(tetrahydropyran-2-yl ether) (Formula XXVIII)

I. Via Lactone XXVI. Refer to Chart 2.

A. A solution of lactone XXXVI, i.e. 5α-hydroxy-3α-tetrahydropyran-2-y loxy-2β-(trans-2-formylethenyl)-1α-cyclopentaneacetic acid, γ-lactone (2.775 g., Preparation 1) in 40 ml. of diethyl ether and 10 ml. of tetrahydrofuran is treated at −70° C. with 1-pentenylmagnesium bromide (prepared from 5-bromo-1-pentene (4.115 g.) and magnesium (0.667 g.) in 40 ml. of diethyl ether) added dropwise over 17 min. The mixture is then stirred at about −60° C. for 22 min. and quenched with saturated aqueous ammonium chloride. Sodium sulfate powder is added for coagulation and the solids filtered off. The filtrate, together with ether washings, is dried and concentrated to an oil, 3.109 g. The product is chromatographed, eluting with methylene chloride-acetone (6:1) to obtain the mono-THP ether, mixed C-15 epimers, 2.427 g., having R$_f$ 0.34 and 0.29 (in methylene chloride-acetone (4:1)), NMR peaks at 6.20–5.4, 5.2–4.78, 4.68, 4.3–3.2, 3.02–2.4, 2.35–1.85, and 1.8–1.2δ, infrared absorption at 3450, 2995, 1775, 1200, 1180, 1120, 1075, 1030, 1020, 975, 920, 870, and 815 cm$^{-1}$, and mass spectral lines at 422.2446, 407, 353, 337, 321, 320, 269, 251, and 85.

b. The above mono-THP ether is treated in methylene chloride solution with excess dihydropyran in the presence of pyridine hydrochloride at about 25° C. for 16 hr. The mixture is diluted with about 300 ml. of methylene chloride and washed with 5% aqueous sodium bicarbonate, water, and brine, and dried. Concentration yields the formula-XXXVIII bis-THP ether title compound, viz. 3α,5α-dihydroxy-2β-[(3R,S)-3-hydroxy- trans-1,7-octadienyl]-1α-cyclopentaneacetic acid γ-lactone, 3,3'-bis(tetrahydropyran-2-yl ether).

II. Via Lactone XXXVII. Refer to Chart 3. A phosphonate reagent is first prepared. Methyl 5-hexenoate is prepared from 5-hexenoic acid by reaction with methanol and concentrated sulfuric acid in refluxing ethylene dichloride, thereafter washing and distilling the product. The anion of dimethyl methylphosphonate, prepared from dimethyl methylphosphonate (82 g.) and 400 ml. of 1.6 M butyllithium in 800 ml. of tetrahydrofuran at −55° to −60° C. is treated with methyl 5-hexenoate (41 g.) added in 65 ml. of tetrahydrofuran over about 10 min. The mixture is stirred at −75° C. for 2 hr. and then at about 25° C. for 18 hr. Acetic acid (26 ml.) is added and the solvent removed under reduced pressure. The residue is taken up in water and ether-methylene chloride (3:1). The organic phase, combined with extractions of the aqueous phase, is washed with cold aqueous sodium bicarbonate and brine, dried, and concentrated. There is obtained, on distillation, dimethyl 2-oxo-6-heptenylphosphonate.

a. The formula-XXXVII bicyclic aldehyde wherein R is benzoyl, i.e. 2-hydroxy-4-benzoxy-5-carboxaldehyde-cyclopentanyl acetic acid γ-lactone (U.S. Pat. No. 3,778,450, 14.5 g.) is added in methylene chloride solution (100 ml.) to the ylid prepared from 25.5 g. of the above phosphonate and 4.2 g. of sodium hydride (57% dispersion) in tetrahydrofuran (500 ml.) first at 0° and then at 20° C. The reaction mixture is warmed from 0° to about 25° C. for one hr., then acidified with 10 ml. of acetic acid and concentrated. The residue is diluted with water and extracted with ether-methylene chloride (3:1). The extracts are washed with cold dilute hydrochloric acid, water, cold aqueous sodium bicarbonate and brine, dried, and concentrated. The residue is chromatographed to yield the formula-XXXVIII 3-oxo-trans-1,7-octadienyl lactone with benzoate blocking group.

b. The formula-XXXIX 3-hydroxy compound, i.e. 5-hydroxy-3-benzoxy-2β-[(3R,S)-3-hydroxy-trans-1,7- octadienyl]-1α-cyclopentaneacetic acid γ-lactone is obtained on reduction with zinc borohydride. For this purpose sodium borohydride (3.78 g.) and anhydrous zinc chloride (13.7 g.) are reacted in 1,2-dimethoxyethane at 0°–25° C. The solution of the reagent is cooled to −20° C. and treated dropwise under nitrogen with a solution of the above 3-oxo compound (10.0 g.) in 75 ml. of dimethoxyethane. When the reaction is completed as shown by TLC, excess borohydride is destroyed by careful addition of water and stirring. The mixture is filtered and the filtrate washed with water and brine, dried, and concentrated. The residue is chromatographed.

c. The benzoate group is removed by treatment of the above product of step b (3.55 g.) with potassium carbonate (1.23 g.) in methanol at about 25° C. for 1.25 hr. The solvent is removed under reduced pressure and the residue is acidified with cold aqueous potassium hydrogen sulfate and extracted with ethyl acetate. The organic phase is washed with water and brine, dried, and concentrated. The residue is lactonized in refluxing benzene for 18 hr. and is thereafter chromatographed to yield the unblocked alkadienyl lactone, i.e. 3α,5α-dihydroxy-2β-[(3R,S)-3-hydroxy-trans-1,7-octadienyl]-1α-cyclopentaneacetic acid γ-lactone.

The above unblocked lactone is treated with excess dihydropyran in the presence of pyridine hydrochloride and worked up as in I-b above to obtain the formula-XXVIII bis-THP ether title compound.

EXAMPLE 2

3α,5α-Dihydroxy-2β-[(3S)-3-hydroxytrans-1,7-octadienyl]-1α-cyclopentaneacetic Acid γ-Lactol, 3,3′-bis-(tetrahydropyran-2-yl Ether) (Formula LIII)

I. Refer to Chart 7. There is first prepared the (3S)-mono-THP 1,7-octadienyl lactone following the procedures of Chart 2 and Example 1-I. A Grignard reagent is prepared in 170 ml. of ether from magnesium (3.14 g.) and 5-bromo-1-pentene (20.80 g.) added dropwise. The reaction mixture is refluxed for one hr., then cooled and added to a solution of the formula-XXVI aldehyde, i.e. 5α-hydroxy-3α-tetrahydropyran-2-yloxy-2β-(trans-2-formylethenyl)-1α-cyclopentaneacetic acid, γ-lactone (24.43 g., Preparation 1) in 250 ml. of diethyl ether at −70° C. over a period of 22 min. The mixture is stirred for an additional 45 min. at −70°, then poured into a mixture of saturated ammonium chloride solution (900 ml.)-ice-ether (300 ml.). The organic phase is separated, combined with extracts of the aqueous layer, dried, and concentrated. The residue is chromatographed, eluting with acetone-methylene chloride (1:8) to (1:6) to yield the mixed 3(S) and 3(R) mono-THP lactones. They are separated by high pressure liquid chromatography on a series of Merck "B" prepacked columns, eluting with acetone-methylene chloride (1:10), to yield the mono-THP 3(S) isomer, 7.92 g. having $R_f$ 0.34 (in acetone-methylene chloride (1:4)), and the same spectral properties reported in Example 1-I-a. There is also obtained the mono-THP 3(R) isomer, 8.83 g., having $R_f$ 0.29 and substantially the same spectral properties.

Continuing with the above 3(S) compound, namely 3α,5α-dihydroxy-2β-[(3S)-3-hydroxy-trans-1,7-octadienyl]1α-cyclopentaneacetic acid γ-lactone, 3-(tetrahydropyran-2-yl ether), there is next prepared the formula-VIII bis (THP ether) intermediate. The above 3(S) compound (7.92 g.) is treated in 55 ml. of methylene chloride with pyridine hydrochloride (about 0.7 g.) and dihydropyran (3.42 g.) at about 25° C. After 4 hr. the mixture is warmed and stirred at 32°–35° C. for 4 hr. The mixture is cooled in an ice bath, diluted with 100 ml. of methylene chloride, washed with cold 5% sodium bicarbonate and brine, dried, and concentrated to the bis (THP ether) intermediate, 9.88 g. having $R_f$ 0.70 (in acetone-methylene chloride (1:6)).

II. The lactone of part I (9.82 g.) is treated in 100 ml. of toluene at −68° C. with diisobutylaluminum hydride (22.65 ml. of 1.5 M. toluene solution) added dropwise over 8 min. The mixture is stirred at −75° for one hr. and then 10 ml. of saturated aqueous sodium sulfate added. The mixture is warmed to room temperature, diluted with 700 ml. of diethyl ether, and treated with powdered sodium sulfate. The solids are removed on a Celite ® filter. The filtrate is dried and concentrated to yield the formula-LIII lactol title compound, having $R_f$ 0.35 (in acetone-methylene chloride (1:6)).

EXAMPLE 3

19,20-Didehydro-PGF$_{2\alpha}$, 11,15-bis-(tetrahydropyran-2-yl Ether) (Formula LIV) and Methyl Ester Refer to Chart 7. The lactol of Example 2 (9.87 g.) is alkylated by the Wittig reaction. The Wittig reagent is first prepared from 4-carboxybutyl triphenylphosphonium bromide (35.1 g.) added to the reaction product of sodium hydride (7.6 g.) and 180 ml. of dimethyl sulfoxide previously warmed to 70°–75° C. for 1.5 hr. and then cooled to about 25° C. for 25 min., then treated with the formula-LIII (3S) lactol in 65 ml. of dimethylsulfoxide added dropwise over 25 min. and stirred additional 30 min. The mixture is acidified in ice water with 2 N potassium hydrogen sulfate and then extracted with ether. The organic phase is washed with brine, dried, and concentrated to yield the formula-LIV bis-THP free acid.

The acid is then esterified with ethereal diazomethane and the resulting methyl ester is chromatographed to yield the title methyl ester 9.37 g., having $R_f$ 0.62 (in acetone-methylene chloride (1:6)), and NMR peaks at 6.18–4.56, 4.37–3.20, 3.65, and 2.78–1.11δ.

EXAMPLE 4

19,20-Didehydro-PGF$_{2\alpha}$ and 19,20-Didehydro-PGF$_{2\alpha}$, Methyl Ester (Formula LV).

Refer to Chart 7.

The bis-THP ether of the title acid (Example 3) is hydrolyzed in acetic acid:water:tetrahydrofuran (20:10:3) at 40° C. for 3 hr. The solvents are removed under reduced pressure and the residue is chromatographed on silica gel, eluting with ethyl acetate-hexane (1:1) to yield the title acid.

The bis-THP ether of the title methyl ester (Example 3) is likewise hydrolyzed in acetic acid:water:tetrahydrofuran (20:10:3) following the same procedure to yield the title compound having $R_f$ 0.48 (in ethyl acetate-methanol (10:1)), and mass spectral lines at 582.3570, 567, 551, 541, 513, 492, 423, 402, and 217.

EXAMPLE 5

19,20-Didehydro-(15R)-PGF$_{2\alpha}$, Methyl Ester (Formula LV).

Refer to Chart 7. Following the procedures of Examples 2–4, but utilizing the (3R) isomer of Example 2-I, namely 3α,5α-dihydroxy-2β-[(3R)-3-hydroxy-trans-1,7-octadienyl]-1α-cyclopentaneacetic acid γ-lactone, 3(tetrahydropyran-2-yl ether) there is prepared the corresponding formula-VIII (3R) bis(THP ether) intermediate and the formula-LIII lactol, then by Wittig alkylation the formula-LIV 19,20-didehydro-(15R)-PGF$_{2\alpha}$, 11,15-bis-(tetrahydropyran-2-yl ether). Finally, after esterification and hydrolysis of the blocking groups, the title compound is obtained, having R$_f$ 0.66 (TLC on silica gel in ethyl acetate-methanol (10:1)).

EXAMPLE 6

19,20-Didehydro-PGF$_{2\alpha}$, Methyl Ester (Formula LV) and 19,20-Didehydro-15R-PGF$_{2\alpha}$,Methyl Ester (Formula LV).

Following the procedure of Example 2-II, the (3R,S) mono-THP lactone of Example 2-I (1.720 g.) is reduced to the corresponding lactol, using 26.3 ml. of 0.56 M diisobutylaluminum hydride at about $-75°$ C. There is obtained 1.660 g. of lactol, having R$_f$ 0.17 (in methylene chloride-acetone (4:1)), and infrared absorption at 3450, 2995, 1130, 1200, 1070, 1020, 975, 915, 870, and 815 cm$^{-1}$.

Following the procedure of Example 3, the above lactol (1.620 g.) is alkylated by the Wittig reaction using the ylid prepared from 4-carboxybutyl triphenylphosphonium bromide (9.105 g.) to yield the corresponding acid. The acid is esterified in methanol-ether with ethereal diazomethane to yield 3.497 g. The ester is chromatographed, eluting with ethyl acetate-Skellysolve B (1:1), to yield the mono-THP mixed C-15 epimers, 1.536 g., having R$_f$ 0.47 and 0.38 (in ethyl acetate-Skellysolve B (1:1)) and infrared absorption at 3450, 2990, 1740, 1430, 1200, 1020, 975, 910, 870 and 815 cm$^{-1}$.

The above mono-THP product is hydrolyzed in acetic acid-water-tetrahydrofuran (20:10:3) at 40° C. for 3 hr., thereafter concentrating. The resulting oil is chromatographed, eluting with ethyl acetate-Skellysolve B (16–0%) to yield first the (15R) title compound, 0.070 g., then a mixture, and finally the (15S) title compound, 0.083 g. The (15R) compound has R$_f$ 0.66, the (15S) has R$_f$ 0.48 (in ethyl acetate-methanol (10:1)), and both have mass spectral peaks at 582.3570, 567, 551, 541, 513, 492, 423, 402, and 217.

EXAMPLE 7

19,20-Didehydro-PGE$_2$, Methyl Ester (Formula (III).

Refer to Chart 1. The formula-IX 11,15-bis(tetrahydropyran-2-yl ether), available from Example 3, is oxidized by the Jones reagent. Thereafter the THP blocking groups are replaced by hydrogen to yield the title compound.

EXAMPLE 8

19,20-Didehydro-PGF$_{2\alpha}$, p-Acetylphenyl Ester

The mixed anhydride is first prepared. A solution of 19,20-didehydro-PGF$_{2\alpha}$ (Example 4) in methylene chloride is treated with triethylamine (2 equiv. ) and isobutylchloroformate (1.01 equiv.) at about 25° C. for 0.5 hr. Solid p-hydroxyacetophenone (1.01 equiv.) is added and stirring continued for 4 hr. The mixture is diluted with methylene chloride, washed with water, 0.1 N sodium hydroxide, water, and brine, dried, and concentrated. The product is chromatographed on silica gel eluting with acetone-hexane to yield the title compound.

EXAMPLE 9

19,20-Didehydro-PGF$_{2\alpha}$, Sodium Salt

A solution of 19,20-didehydro-PGF$_{2\alpha}$, (Example 3) in methanol is neutralized with a solution of sodium carbonate in water. The mixture is concentrated to a small volume, diluted with acetonitrile and concentrated to a residue of the title compound.

EXAMPLE 10

19,20-Didehydro-PGF$_{2\alpha}$, Amide

Refer to Chart 17. The formula-CIX mixed anhydride is prepared following the procedure of Example 8. There is then added at about $-5°$ C., a saturated solution of ammonia in acetonitrile and the mixture stirred at $-5°$ C. for 10 min. The reaction mixture is diluted with brine and water (5:1) and extracted with ether. The organic phase is washed with brine and 2 N hydrochloric acid, then with brine and 5% sodium bicarbonate, finally with brine, dried and concentrated. The residue is chromatographed on a HPLC silica gel column, eluting with acetone to yield the title compound.

EXAMPLE 11

19,20-Didehydro-PGF$_{2\alpha}$, Methanesulfonamide (Formula CXV)

Refer to Chart 18. A solution of mixed anhydride in dimethylformamide (prepared from 19,20-didehydro-PGF$_2$ of Example 4 by reaction with isobutylchloroformate in the presence of triethylamine as in Example 8) is treated, with stirring, at 0° C. with about 4 equivalents of methanesulfonamide sodium salt (prepared from methanesulfonamide and methanolic sodium methoxide in methanol, concentrating and azeotroping with benzene), thereafter adding sufficient hexamethylphosphoramide to insure a homogeneous mixture. The mixture is stirred at about 25° C. for 16 hr., then acidified with cold dilute hydrochloric acid and extracted with ethyl acetate. The organic phase is washed with water and brine, dried, and concentrated. The residue is chromatographed on silica gel, eluting with methanol-methylene chloride, to yield the title compound.

EXAMPLE 12

3α,5α-Dihydroxy-2β-(3-oxo-trans-1,7-octadienyl)-1α-cyclopentaneacetic Acid γ-Lactone, 3-tetrahydropyran-2-yl Ether (Formula CXXIII)

Refer to Chart 21. The formula-XXXVIII 3-oxo intermediate of Example 1-II-a is deblocked by treatment with potassium carbonate in methanol at about 25° C. for 1.25 hr., following the procedure of Example 1-II-c. Thereafter the THP ether is formed with excess dihydropyran in the presence of pyridine hydrochloride to yield the title compound.

Alternatively, the 3-hydroxy mono-THP lactones of Example 2 are oxidized by Jones reagent. Thus, the mono-THP 1,7-octadienyl lactone (8.83 g.) is treated in acetone at $-35°$ C. with Jones Reagent (17 ml. of 2.67 M) added dropwise. Then stirring is continued for 35 min. and finally isopropanol (6.0 ml.) added with additional stirring. The mixture is added to a mixture of 5% sodium bicarbonate and ice-water and extracted with ether. The organic phase is washed with brine, dried, and concentrated to yield the title compound, 7.63 g., having R$_f$ 0.52 (in ethyl acetate-Skellysolve B (2:1)).

EXAMPLE 13

3α,5α-Dihydroxy-2β-[(3R,S)-3-hydroxy-3-methyl-trans-1,7-octadienyl]-1α-cyclopentaneacetic Acid γ-Lactone, 3-tetrahydropyran-2-yl ether (Formula CXXIV).

Refer to Chart 21. The formula-CXXIII 3-oxo lactone (Example 12, 7.63 g.) in 500 ml. of tetrahydrofuran is treated at −78° C. with methylmagnesium bromide (35.4 ml. of 3.1 M) added dropwise over 20 min. Stirring is continued for 2.5 hr. at about −60° C. and then the reaction is quenched with 400 ml. of saturated aqueous ammonium chloride and 300 ml. of ice water and ether is added. The organic phase is separated, combined with organic extracts of the aqueous phase, dried, and concentrated. The residue is chromatographed, eluting with ethyl acetate-Skellysolve B (2:1) to yield the mono (THP ether) of the title compound having $R_f$ 0.27 (in ethyl acetate-Skellysolve B (2:1)), NMR peaks at 6.20–5.40, 5.40–4.52, 4.30–3.18, 3.07–1.35, and 1.23δ; and infrared absorption at 3400, 2850, 1740, 1620, 1420, 1330, 1150, 1110, 1060, 1020, 965, 900, 960, and 805 cm$^{-1}$.

EXAMPLE 14

3α,5α-Dihydroxy-2β-[(3R,S)-3-hydroxy-3-methyl-trans-1,7-octadienyl]-1α-cyclopentaneacetic Acid γ-Lactol, 3-tetrahydropyran-2-yl Ether (Formula CXXV)

Refer to Chart 21. The formula-CXXIV lactone (Example 13, 5.20 g.) in 100 ml. of toluene at −68° C. is treated with diisobutylaluminum hydride (23.8 ml. of 1.5 M. toluene solution) added dropwise over 8 min. Thereafter following the procedure of Example 2-II, there is obtained the formula-CXXV lactol title compound, 3.79 g., having $R_f$ 0.31 (in acetone-methylene chloride (1:3)), NMR peaks at 6.18–5.37, 5.33–4.29, 4.25–3.21, 3.05–1.34, and 1.26δ, and IR absorption at 3350, 2900, 1640, 1440, 1340, 1260, 1200, 1120, 1060, 970, 910, 865, and 810 cm$^{-1}$.

EXAMPLE 15

(15R,S)-15-Methyl-19,20-didehydro-PGF$_{2α}$, 11-tetrahydropyran-2-yl Ether, Methyl ester (Formula CXXVI).

Refer to Chart 21. The formula-CXXV lactol (Example 14, 3.79 g.) is subjected to the Wittig reaction following the procedure of Example 3, and thereafter esterified to yield the formula-CXXVI title compound, having $R_f$ 0.34 (in acetone-methylene chloride (1:6)), NMR peaks at 6.16–5.20, 5.20–4.55, 4.27–3.17, 3.65, 2.67–1.34, and 1.27δ, and infrared absorption at 3400, 2900, 1720, 1630, 1430, 1340, 1190, 1120, 1065, 1010, 965, 900, 860, and 805 cm$^{-1}$.

EXAMPLE 16

15-Methyl-19,20-didehydro-PGF$_{2α}$, Methyl Ester (Formula LV) and (15R)-15-Methyl-19,20-didehydro-PGF$_{2α}$, Methyl Ester (Formula LV).

Refer to Chart 21. The product of Example 15 is hydrolyzed to replace tetrahydropyranyl groups in the usual way, for which see Example 4. The 15-epimers are separated by silica gel chromatography to yield the title compounds.

EXAMPLE 17

3α,5α-Dihydroxy-2β-[(3R,S)(7R,S)-3,7-dihydroxy-trans-1-octenyl]-1α-cyclopentaneactic Acid γ-Lactone, 3,3′-bis(Tetrahydropyran-2-yl Ether) (Formula CXXIX)

Refer to Chart 23. The title compound is obtained by oxymercuration-demercuration. The formula-VIII alkadienyl lactone, i.e. 3α,5α-dihydroxy-2β-[(3R,S)-3-hydroxy-trans-1,7-octadienyl]-1α-cyclopentaneacetic acid γ-lactone, 3,3′-bis(tetrahydropyran-2-yl ether) (Example 1, 14.54 g.) is added dropwise to a stirred suspension of mercuric acetate (14.946 g.) in 120 ml. of water and 120 ml. of tetrahydrofuran and the mixture is stirred at about 25° C. for 22 hr. The mixture is cooled in an ice bath and treated with sodium borohydride (3.752 g.) added in portions over 6–8 min. The temperature is raised to about 25° C. and stirring continued for 3 min. The mixture is diluted with ether (300 ml.) decanted from mercury, separated, and the organic phase combined with ether extracts of the aqueous phase. The organic phase is washed with brine, dried, and concentrated to an oil, 15.88 g. The oil is chromatographed on silica gel, eluting with acetone-methylene chloride (1:4 to 2:4) to obtain the formula CXXIX 7-hydroxy title compound, 11.566 g., having $R_f$ 0.38 (TLC on silica gel in acetone-methylene chloride (1:3)), NMR peaks at 5.50, 5.00, 4.63, 4.20–3.10, 3.00–1.20, and 1.15δ, and infrared absorption at 3500, 2990, 1775, 1120, 1020, 970, 910, 865, 810, and 730 cm$^{-1}$.

EXAMPLE 18

2-Decarboxy-2-hydroxymethyl-(19R,S)-19-hydroxy-PGE$_1$ (Formula CXLIV) and 2-Decarboxy-2-hydroxymethyl-13,14-dihydro-(19R,S)-19-hydroxy-PGE$_1$ (Formula CXLV).

I. Refer to Chart 24. The formula-CXXXV compound is first prepared. The formula-CXXXIV compound, namely 19,20-didehydro-PGF$_{2α}$, 11,15-bis(tetrahydropyran-2-yl ether), methyl ester (Example 3, 2.60 g.) is silylated with dimethyl-t-butyl-chlorosilane (1.465 g.) in 10 ml. of dimethylformamide and 1.325 g. of imidazole for 16 hr. at about 25° C. The mixture is diluted with ice-water and extracted with diethyl ether. The extracts are washed, dried, concentrated, and chromatographed to yield the formula-CXXXV 19,20-didehydro-9(dimethyl-t-butylsilyl)-PGF$_{2α}$, 11,15-bis(-tetrahydropyran-2-yl ether), methyl ester having $R_f$ 0.69 (in ethyl acetate-Skellysolve B (1:4)).

II. The formula-CXXXVI compound is prepared by oxymercuration-demercuration. The formula-CXXXVI compound (11.30 g.) in 100 ml. of tetrahydrofuran is added dropwise over a 15 minute period to a stirred suspension of mercuric acetate (7.76 g.) in 100 ml. of water and 100 ml. of tetrahydrofuran at about 25° C. After 3.75 hr. the mixture is cooled to 5° C. and treated with sodium borohydride (1.46 g.). The mixture is stirred an additional 5 min. without cooling, then diluted with ether and filtered. The organic phase, together with ether-extracts of the aqueous phase, is dried and concentrated. The residue is chromatographed, eluting with ethyl acetate-Skellysolve B (1:2 to 1:1) to yield the formula-CXXXVI compound, 9-(dimethyl-t-butylsilyl)-(19R,S)-19-hydroxy-PGF$_{2α}$, 11,15-bis(tetrahydropyran-2-yl ether), methyl ester, 8.86 g., having $R_f$ 0.23 (TLC on silica gel in ethyl acetate-Skellysolve B (1:2)), and NMR peaks at 5.72–5.15, 4.76–4.46, 4.28–3.09, 3.58, 2.74–1.22, 1.08, and 0.87δ.

III. The above material is reduced with hydrogen over palladium (5%)-on-carbon catalyst (0.250 g.) in 75 ml. of ethyl acetate containing about 0.3 ml. of acetic acid. Additional catalyst and acetic acid are added as necessary to obtain 106 ml. uptake of hydrogen. The product (CXXXVII) is a mixture of the $PGE_1$ and 13,14-dihydro compounds in a ratio of about 0.4/0.6.

IV. The above formula-CXXXVII compounds (about 2.55 g.) are treated with dihydropyran (1.50 ml.) and pyridine hydrochloride (0.120 g.) in 40 ml. of methylene chloride for 15 hr. at about 25° C. The mixture is diluted with 175 ml. of methylene chloride, washed with 5% aqueous sodium bicarbonate, water, and brine, dried and concentrated to the formula-CXXXVII compounds, 2.765 g.

V. The above methyl esters are reduced with lithium aluminum hydride (0.278 g.) in 10 ml. of diethyl ether with stirring for 1.5 hr. at about 25° C. The mixture is chilled and quenched with saturated aqueous sodium sulfate, diluted with ether, and treated with powdered sodium sulfate. The mixture is filtered, washed with ether, concentrated and dried to an oil, 2.542 g. represented by formula CXXXIX.

VI. The formula-CXXIX C-1 alcohols are blocked by treating with dihydropyran (1.40 ml.) and pyridine hydrochloride (0.120 g.) in 40 ml. of methylene dichloride for about 17 hr. at about 25° C. After the usual work-up there is obtained 2.829 g. of an oil represented by formula-CXL.

VII. The above product is desilylated in preparation for oxidation at C-9. The product of VI is treated with n-tetrabutylammonium fluoride (12 ml. of 0.75 M in tetrahydrofuran with 15 ml. of tetrahydrofuran) for about 6.5 hr. at 25° C. and one hr. at 40° C. There is added an additional 3 ml. of reagent and the reaction continued at 40° C. for one hr. The mixture is diluted with 250 ml. of ether, washed with brine, water, and brine, dried and concentrated. The mixture is chromatographed to yield an oil, 1.970 g., represented by formula CXLI.

VIII. The formula-CXLI product of VII above is oxidized with Jones reagent, using 1.85 ml. (2.67 M) in 65 ml. of acetone, quenching with 3 ml. of isopropanol, to yield 1.910 g. of the mixed formula-CXLIII compounds.

IX. The product of VIII is hydrolyzed to remove blocking groups, using 80 ml. of acetic acid-water-tetrahydrofuran (20:10:3) for 4 hr. at about 45° C. The solvents are removed azeotropically with benzene to give an oil, 1.680 g. The residue is chromatographed by HPLC, eluting with acetone-methylene chloride (2:1), to yield (after some mechanical losses) the $PGE_1$-type title compound (0.114 g.) and the less polar 13,14-dihydro-$PGE_1$-type title compound (0.230 g.), CXLIV and CXLV respectively.

EXAMPLE 19

2-Decarboxy-2-hydroxymethyl-(19R,S)-19-hydroxy-$PGF_{1\alpha}$ and
2-Decarboxy-2-hydroxymethyl-13,14-dihydro-(19R,S)-19-hydroxy-$PGF_{1\alpha}$ Refer to Chart 24. The formula-CXLI compounds are deblocked in dilute acid to yield CXLII, the mixed title compounds, which are separated by silica gel chromatography.

EXAMPLE 20

2-Decarboxy-2-hydroxymethyl-(19R,S)-19-hydroxy-$PGF_{1\alpha}$ (Formula CL)

I. Refer to Chart 25. The formula-CXLVI starting material, namely 19,20-didehydro-$PGF_{2\alpha}$, 11,15-bis(tetra-hydropyran-2-yl ether), methyl ester (Example 3), is first oxymercurated. A stirred suspension of mercuric acetate (7.76 g.) in 100 ml. of water and 100 ml. of tetrahydrofuran is treated with 19,20-didehydro-$PGF_{2\alpha}$, methyl ester (9.25 g.) in 100 ml. of tetrahydrofuran added dropwise at 25° C. in about 15 min. The mixture is stirred at about 25° C. for 3.75 hr., cooled to 5° C. and treated with portions of sodium borohydride (1.46 g.) to demercurate. Stirring is continued for 5 min. while warming to about 25° C. The mixture is diluted with ether (about one l.) and filtered through Celite ®. The organic phase is dried and concentrated to crude CXLVII. The residue is chromatographed, eluting with ethyl acetate, to yield CXLVII, namely (19R,S)-19-hydroxy-$PGF_{2\alpha}$, 11,15-bis(tetrahydropyran-2-yl ether), methyl ester, having $R_f$ 0.38 (in ethyl acetate-Skellysolve B (4:1)), and NMR peaks at 5.89–5.03, 4.83–4.52, 4.28–3.17, 3.65, 2.78–1.28, and 1.18δ.

II. Next is prepared the formula-CXLVIII corresponding $PGF_{1\alpha}$ compound. Compound CXLVII above (1.270 g.) in 40 ml. of ethyl acetate together with 0.130 g. of 5 percent palladium-on-carbon catalyst is reduced with hydrogen at one atmosphere at about 25° C. The catalyst is filtered off and the filtrate is concentrated to yield the formula-CXLVIII compound, namely (19R,S)-19-hydroxy-$PGF_{1\alpha}$, 11,15-bis(tetrahydropyran-2-yl ether), methyl ester, 1.230 g., having $R_f$ (in ethyl acetate-Skellysolve B (4:1)), NMR peaks at 5.50, 4.70, 4.30–3.20, 3.67, 2.50, 2.70–1.20, and 1.15δ, and infrared absorption at 3500, 2995, 1730, 1430, 1200, 1020, 970, 865, and 805 $cm^{-1}$.

III. The corresponding C-1 alcohol is obtained by reduction. A solution of compound CXLVIII above (1.230 g.) in 15 ml. of ether is added to an ice-cold suspension of lithium aluminum hydride (0.337 g.) in 10 ml. of ether. An additional 20 ml. of ether is added and the mixture is stirred at about 25° C. for one hr. Thereafter about 7 ml. of saturated aqueous sodium sulfate is added dropwise, and solid sodium sulfate to coagulate aluminum salts, and the mixture is filtered. The filtrate is concentrated to an oil, 1.150 g. The procedure of reduction is repeated if necessary to convert unreacted formula-CXLVIII material. The resulting oil is chromatographed by HPLC on a Merck "B" column, eluting with ethyl acetate-Skellysolve B (9:1)), to yield the formula-CXLIX compound, namely 2-decarboxy-2-hydroxymethyl-(19R,S)-19-hydroxy-$PGF_{1\alpha}$, 11,15-bis(-tetrahydropyran-2-yl ether), 0.985 g., having NMR peaks at 5.50, 4.70, 4.25–3.20, 2.80, 2.60–1.20, and 1.15δ, and infrared absorption at 3400, 2990, 1430, 1120, 1020, 970, 900, 860, and 805 $cm^{-1}$.

IV. The formula-CL title compound is obtained on deblocking the formula-CXLIX compound above in acetic acid-water-tetrahydrofuran (20:10:3) at about 40°–45° C. for 45 min., concentrating, and chromatographing.

EXAMPLE 21

9-(Dimethyl-t-butylsilyl)-19-keto-PGF$_{2\alpha}$, bis(Tetrahydropyranyl Ether) (Formula CLXIX) and 19-Keto-PGF$_{2\alpha}$, Methyl Ester (Formula CLXX)

I. Refer to Chart 29. The formula-CXXXVI product of Example 18 (0.500 g.) in 8 ml. of methylene chloride is added to Collins reagent (prepared from chromic anhydride (0.526 g.) in pyridine (0.831 g.)) and methylene chloride at 0° C. The mixture is stirred at about 25° C. for 1.2 hr., then diluted with 200 ml. of ether, filtered, and concentrated. The residue (0.502 g.) consists of the formula-CLXIX 9-silyl-11,15-bis(THP ether)-19-keto compound.

II. The product of I is hydrolyzed in tetrahydrofuran-acetic acid-water (3:20:10) at 47°-50° C. for 4 hr. The mixture is concentrated and then chromatographed eluting with acetone-methylene chloride (1:1). There is obtained the title compound, 0.126 g., having R$_f$ 0.33 (TLC on silica gel in acetone-methylene chloride (1:1)), NMR peaks at 5.87–5.06, 4.60–3.12, 3.65, 2.69–0.84, and 2.13$\delta$; infrared absorption at 3350, 2900, 1730, 1430, 1350, 1220, 1160, and 965 cm$^{-1}$, and mass spectral lines at 598.3545, 583, 513, 508, 493, 423, 418, 217, and 187.

EXAMPLE 22

(15R)-19-Keto-PGF$_{2\alpha}$ (Formula CLXX)

Refer to Charts 24 and 29. Following the procedures of Examples 3, 18, and 21 but replacing the (3S) lactone isomer of Example 3 with the corresponding (3R) isomer obtained in Example 2, there is obtained the title compound, having R$_f$ 0.27 (TLC on silica gel in methylene chloride-acetone (1:1)), NMR peaks at 5.70–5.15, 4.10, 3.67, 3.20, 2.17, and 2.70–120$\delta$; infrared absorption at 3300, 2990, 1710, 1420, 1350, and 965 cm$^{-1}$; and high resolution mass spectral line at 598.3516.

EXAMPLE 23

19-Keto-13,14-dihydro-PGF$_{1\alpha}$, Methyl Ester (Formula V)

I. The formula-CXXXVI product of Example 18-II, i.e. 9-dimethyl-t-butylsilyl-(19R,S)-19-hydroxy-PGF$_{2\alpha}$, 11,15-bis(tetrahydropyran-2-yl ether), methyl ester (2.0 g.) is reduced at C$_5$-C$_6$ and C$_{13}$-C$_{14}$ by catalytic hydrogenation in 75 ml. of ethyl acetate using 200 mg. of 5% palladium-on-carbon catalyst to a mixture of the corresponding PGF$_{1\alpha}$ and 13,14-dihydro-PGF$_{1\alpha}$ products which is further hydrogenated to the 13,14-dihydro compound.

II. Following the oxidation procedures of Example 21, the corresponding 9-silyl-11-15-bis(THP ether)-13,14-dihydro-19-keto-PGF$_{1\alpha}$, methyl ester is obtained.

Thereafter, by hydrolysis in tetrahydrofuran-acetic acid-water, the title compound is obtained. The TLC and NMR data show the presence of a less polar acetal form as well as the 19-keto form. R$_f$ 0.26, 0.54, and 0.67 (TLC on silica gel in A-IX solvent); NMR peaks at 4.52–3.30, 3.62, 3.38, 3.00–0.87, 2.08, and 1.18$\delta$; and mass spectral lines at 512.3336, 528, 517, 497, 427, 422, 412, 369, and 217.

EXAMPLE 24

2-Decarboxy-2-hydroxymethyl-19-keto-PGE$_1$ (Formula CLXXXIII).

I. Refer to Chart 31. The formula-CXLIX compound, namely 2-decarboxy-2-hydroxymethyl-(19R,S)-19-hydroxy-PGF$_{1\alpha}$, 11,15-bis(tetrahydropyranyl ether) (Example 20-III, 0.985 g.) is blocked at C-1 with silyl by treating in 6 ml. of ice-cold dimethylformamide with 0.135 g. of dimethyl-t-butylsilyl chloride and 0.122 g. of imidazole. The mixture is stored at 0°-5° C., for 2 hr., then treated with additional 0.135 g. of dimethyl-t-butylsilyl chloride and 0.122 g. of imidazole. Finally, after 18 hr. at 0°-5° C., the mixture is again treated with 0.085 g. of silyl reagent and stored at 0°-5° C. for 3 hr. The mixture is quenched with crushed ice (about 10 g.), stirred, diluted with water, and extracted with ether. The organic phase is washed with water, and brine, dried, and concentrated to an oil, 1.125 g. The oil is chromatographed by HPLC, eluting with ethyl acetate-Skellysolve B (1:1), to yield the formula-CLXXXI compound, 0.475 g. having NMR peaks at 5.50, 4.70, 4.30–3.30, 2.70–1.25, 1.15, 0.90, and 0.03$\delta$, and infrared absorption at 3500, 2995, 1460, 1225, 1100, 1020, 835, and 770 cm$^{-1}$.

II. The C-9 and C-19 hydroxy groups of the formula-CLXXXI compound of I are oxidized, using Collins reagent following the procedure of Example 21 but using 1.036 g. of chromic anhydride and 1.66 ml. of pyridine in 54 ml. of methylene chloride with 0.475 g. of CLXXXI above. There is obtained the formula-CLXXXII compound, namely 2-decarboxy-2-hydroxymethyl-19-keto-PGE$_1$, 1-dimethyl-t-butylsilyl ether, 11,15-bis(tetrahydropyran-2-yl ether), 0.428 g., having NMR peaks at 5.60, 4.70, 4.30–3.10, 2.10, 2.85–1.10, 0.90 and 0.05$\delta$; and infrared absorption at 2990, 1730, 1710, 1460, 1340, 1200, 1100, 970, 830, and 770 cm$^{-1}$.

III. The product of II above is deblocked in 15 ml. of acetic acid-water-tetrahydrofuran (20:10:3) at 40°-45° C. for 3 hr. The solvents are removed azeotropically with chloroform under reduced pressure. The residue is chromatographed, eluting with acetone-methylene chloride (1:1) to yield the formula-CLXXXIII title compound, 0.042 g., and its formula-CLXXXIV hemi-acetal, 0.052 g. The hemi-acetal is converted to the 19-keto form in acetic acid-water-tetrahydrofuran. The 19-keto compound has NMR peaks at 5.65, 4.15, 3.60, 3.00, 2.13, and 2.65–1.20$\delta$, infrared absorption at 3400, 2990, 1715, 1350, 1220, 1070, and 965 cm$^{-1}$, and high resolution mass spectral peak at 570.3626.

EXAMPLE 25

(19R,S)-19-Hydroxy-PGF$_{2\alpha}$, Methyl Ester, 9,19-bis(dimethyl-t-butylsilyl ether), 11,15-bis(tetrahydropyran-2-yl ether) (Formula CLXXXV)

Refer to Chart 32. Following the procedure of Example 18-I the formula CXXXVI 19-hydroxy compound of Example 18-II (4.34 g.) is silylated to yield the title compound, 4.84 g.

EXAMPLE 26

2-Decarboxy-2-hydroxymethyl-(19R,S)-19-hydroxy-PGF$_{2\alpha}$, 9,19-bis(dimethyl-t-butylsilyl ether), 11,15-bis(tetrahydropyran-2-yl ether) (Formula CLXXXVI)

Refer to Chart 32. The formula-CLXXXV product of Example 25 (4.84 g.) in 35 ml. of ether is added dropwise to a suspension of lithium aluminum hydride (0.943 g.) in 125 ml. of ether at about 25° C. After 4.5 hr. an additional 0.472 g. of lithium aluminum hydride is added and again after another hour. The mixture is heated at reflux for 30 min., then cooled in an ice bath and quenched with gradual addition of 55 ml. of saturated aqueous sodium sulfate. Anhydrous powdered sodium sulfate is added and the mixture filtered. The filtrate is concentrated to yield the title compound, having $R_f$ 0.58 (TLC on silica gel in ethyl acetate-Skellysolve B (1:2)) and NMR peaks at 5.73–5.00, 4.76–4.43, 4.32–3.12, 2.75–1.19, 1.08, 0.87, and 0.84$\delta$.

EXAMPLE 27

2-Decarboxy-2-hydroxymethyl-(19R,S)-19-hydroxy-PGF$_{2\alpha}$, 9,19-bis(dimethyl-t-butylsilyl ether), 1,11,15-tris(tetrahydropyran-2-yl ether) (Formula CLXXXVII).

Refer to Chart 32. The formula-CLXXXVI product of Example 26 (4.67 g.) in 25 ml. of methylene chloride is treated with dihydropyran (0.941 g.) in the presence of a catalytic amount of pyridine hydrochloride at about 25° C. After 5 hr. additional dihydropyran (0.52 g.) is added. Finally the mixture is diluted with 150 ml. of methylene chloride, washed with 5% aqueous sodium bicarbonate and brine, dried, and concentrated to yield the title compound, 5.25 g., having $R_f$ 0.71 (in ethyl acetate-Skellysolve B (1:2)).

EXAMPLE 28

2-Decarboxy-2-hydroxymethyl-(19R,S)-19-hydroxy-PGF$_{2\alpha}$, 1,11,15-tris(tetrahydropyran-2-yl ether) (Formula CLXXXVIII)

Refer to Chart 32. The formula-CLXXXVII compound of Example 27 (5.19 g.) is desilylated by treatment in tetrahydrofuran with 8 equivalents of tetra(n-butyl)ammonium fluoride at 40° C. The reaction mixture is diluted with 150 ml. of ethyl acetate, washed with brine and water and brine again, dried, and concentrated. The residue is chromatographed, eluting with ethyl acetate-Skellysolve B (2:1) to yield the title compound, 3.10 g., having $R_f$ 0.35 (in ethyl acetate-Skellysolve B (2:1)) and NMR peaks at 5.75–5.12, 4.84–4.50, 4.35–3.15, 2.73–1.05, and 1.16$\delta$.

EXAMPLE 29

2-Decarboxy-2-hydroxymethyl-(19R,S)-19-hydroxy-PGF$_{1\alpha}$, 1,11,15-tris(tetrahydropyran-2-yl ether) (Formula CLXXXVIII)

Following the procedure of Example 23 the formula-CLXXXVIII product of Example 28 is catalytically hydrogenated to the PGF$_{1\alpha}$ title compound, having $R_f$ 0.32 (in ethyl acetate-Skellysolve B (2:1)) and NMR peaks at 5.73–5.27, 4.89–4.45, 4.33–3.15, 2.83–1.00, and 1.18$\delta$.

EXAMPLE 30

2-Decarboxy-2-hydroxymethyl-19-keto-PGE$_1$ (Formula CXCI)

Refer to Chart 32. Following the procedure of Example 21 the formula-CLXXXVIII product of Example 29 (1.90 g.) is oxidized and then hydrolyzed to the title compound, 0.360 g. The product is contaminated with a small amount of the corresponding cis-$\Delta^5$-13,14-dihydro compound. Data for the product are: $R_f$ 0.24 (in acetone-methylene chloride (1:1)), NMR peaks at 5.80–5.55, 5.55–5.28 (impurity), 4.60–3.22, 3.53, 2.92–0.95, and 2.08$\delta$, and infrared absorption at 3300, 2850, 2800, 1700, 1420, 1390, 1340, 1300, 1230, 1150, 1065, 1000, 960, and 720 cm$^{-1}$.

EXAMPLE 31

2-Decarboxy-2-hydroxymethyl-(19R,S)-19-hydroxy-PGF$_{2\alpha}$ (Formula CLXXXIX)

Refer to Chart 32. Following the procedure of Example 21, the formula-CLXXXVIII compound of Example 28 is deblocked by acid hydrolysis in tetrahydrofuran-acetic acid-water (3:20:10) at about 40°–45° C. to yield the title compound.

EXAMPLE 32

2-Decarboxy-2-hydroxymethyl-19-keto-PGE$_2$ (Formula CXCI)

Refer to Chart 32. The formula-CLXXXVIII compound of Example 28 (1.2 g.) is oxidized with Jones reagent (3.6 ml. of 2.67 M) added dropwise to the acetone solution at $-35°$ C., thereafter stirring at about $-20°$ C. for 35 min. The reaction is quenched with isopropanol (6.0 ml.) and stirring continued for 5 min. The mixture is poured into 250 ml. of 5% aqueous sodium bicarbonate and 150 ml. of ice water and extracted with ether. The organic phase is washed with brine, dried, and concentrated. The residue is hydrolyzed to remove blocking groups in tetrahydrofuran-acetic acid-water (3:20:10) at 30° C. for 16 hr. and the solution is concentrated. The residue is chromatographed on a high pressure Merck "B" column eluting with acetone-methylene chloride )1:1) containing 1% acetic acid, to yield the title compound, 0.310 g., having $R_f$ 0.30 (in acetone-methylene chloride (1:1)) and NMR peaks at 5.84–5.52, 5.52–5.00, 4.58–3.78, 3.78–3.16, 2.98–0.90, and 2.07$\delta$.

EXAMPLE 33

3$\alpha$,5$\alpha$-Dihydroxy-2$\beta$-[(3RS)-3-hydroxy-7-oxo-trans-1-octenyl)-1$\alpha$-cyclopentaneacetic] Acid $\gamma$-Lactone, 3,3'-bis(Tetrahydropyran-2-yl Ether) (Formula CXCVII).

Refer to Chart 34. The formula-CXXIX 7-hydroxy lactone (Example 17, 10.02 g.) in 300 ml. of acetone is treated at $-30°$ C. with Jones reagent (14.95 ml. of 2.67 M) added dropwise within 10 min. The mixture is stirred at $-25°$ to $-20°$ C. for additional 18 min., then quenched with 20 ml. of isopropanol and stirred 5 min. more. The mixture is added to 500 ml. of cold 5% sodium bicarbonate and 800 ml. of ethyl acetate, separated, and the organic phase is combined with ether extracts of the aqueous phase. The organic phase is washed with 5% sodium bicarbonate, ice water, and brine, dried, and concentrated to yield the title compound, 9.93 g., having $R_f$ 0.64 (TLC on silica gel in acetone-methylene chloride (1:3), and NMR peaks at 5.50, 5.00, 4.63, 4.25–3.0), 2.13, and 3.00–1.20$\delta$.

EXAMPLE 34

3$\alpha$,5$\alpha$-Dihydroxy-2$\beta$[(3R,S)-3,7-dihydroxy-7-methyl-trans-1-octenyl]-1$\alpha$-cyclopentaneacetic Acid $\gamma$-Lactone, 3,3'-bis(Tetrahydropyran-2-yl Ether) (Formula CXCVIII)

Refer to Chart 34. The Formula-CXCVII 7-oxo lactone (Example 33, 0.500 g.) in 33 ml. of diethyl ether is treated at $-78°$ C. with 2 equivalents of methylmagnesium bromide (0.766 ml. of 2.9 M) added dropwise over one min. The mixture is stirred at $-78°$ for 30 min. more, then treated with an additional 2 equivalents of methylmagnesium bromide at $-78°$ for 2 hr. The mixture is added to 40 ml. of saturated aqueous ammonium chloride and extracted with ether. The organic phase is washed with brine, dried, and concentrated. The concentrate is chromatographed on a HPLC column, eluting with acetonemethylene chloride (1:5) to yield the title compound, 0.391 g., having $R_f$ 0.39 (TLC on silica gel in acetonemethylene chloride (1:3)), NMR peaks at 5.66–5.33, 5.184.81, 4.81–4.47, 4.29–3.16, 2.97–1.29, and 1.16$\delta$, infrared absorption at 3550, 3000, 1770, 1460, 1440, 1430, 1350, 910, 865, 840, 810, 765, and 735 cm$^{-1}$, and mass spectral lines at 523.3118, 439, 437, 436, 421, 395, 131, and 85.

EXAMPLE 35

3$\alpha$,5$\alpha$-Dihydroxy-2$\beta$-[(3R,S)-3,7-dihydroxy-7-methyl-trans-1-octenyl)-1$\alpha$-cyclopentaneacetaldehyde $\gamma$-Lactol, 3,3'-bis(Tetrahydropyran-2-yl Ether) (Formula CXCIX).

Refer to Chart 34. The formula-CXCVIII 7-hydroxy-7-methyl lactone (Example 34, 6.98 g.) in 100 ml. of toluene is reduced at $-78°$ C. with diisobutylaluminum hydride (DIBAL) (25 ml. of 1.5 M in toluene) added dropwise over 13 min. The mixture is stirred at $-78°$ for one hr., treated with additional DIBAL (5 ml.), stirred for 2.25 hr. and again treated with DIBAL (5 ml.). After 0.75 hr. more stirring, the mixture is warmed to $-40°$ over 30 min., then cooled to $-78°$ and carefully quenched with saturated aqueous sodium sulfate. The mixture is diluted with 850 ml. of diethyl ether, stirred with powdered sodium sulfate (20 g.) until the aluminum salts coagulate, then filtered. The filtrate is concentrated and then chromatographed on silica gel eluting with acetone-methylene chloride (1:2 to 1:1) to yield the title lactol compound, 4.89 g. The product has $R_f$ 0.24 (TLC on silica gel in acetone-methylene chloride (1:2)), NMR peaks at 5.77–5.0, 4,86–4.33, 4.33–3.18, 3.11–1.27, and 1.15$\delta$, infrared absorption at 3500, 3000, 1750, 1730, 1470, 1450, 1440, 1370, 1340, 1200, 1120, 910, 865, and 810 cm$^{-1}$, and mass spectral lines at 527.3201, 426, 336, 247, 246, 131, and 85.

EXAMPLE 36

19-Hydroxy-19-methyl-PGF$_{2\alpha}$, Methyl Ester, 11,15-bis(Tetrahydropyran-2-yl Ether), Mixed C-15 Epimers (Formula CC).

Refer to Chart 34. The Wittig reagent is first prepared from 4-carboxybutyl triphenylphosphonium bromide (16.19 g.) added to the reaction product of sodium hydride (3.51 g.) and 85 ml. of dimethylsulfoxide previously warmed to 70°–75° C. for 1.5 hr. and then cooled to about 25° C. The mixture is stirred at about 25° C. for 25 min., then treated with the formula-CXCIX lactol (Example 35, 4.89 g.) in 35 ml. of dimethylsulfoxide added dropwise over 15 min. and stirred additional 30 min. The mixture is added to one liter of ice-water containing 250 ml. of 2 N potassium hydrogen sulfate and then extracted with ether. The organic phase is washed with brine, dried, and concentrated. The product, in 100 ml. of ether and 5 ml. of methanol, is esterified and diazomethane. The solution is concentrated and then chromatographed on a HPLC column eluting with ethyl acetate-Skellysolve B (1:1) to yield the title compounds, 4.08 g. having $R_f$ 0.20 (TLC on silica gel in ethyl acetate-Skellysolve B (2:1)) and 0.60 (TLC on silica gel in acetone-methylene chloride (1:2)), NMR peaks at 5.77–5.29, 4.89–4.60, 4.34–3.16, 3.67, 2.82–1.33, and 1.20$\delta$, and infrared absorption at 3550, 3000, 1740, 1430, 1350, 1200, 1130, 1070, 1020, 970, 900, 865, and 810 cm$^{-1}$.

EXAMPLE 37

19-Hydroxy-19-methyl-PGF$_{2\alpha}$, Methyl Ester and its (15R) Epimer (Formula CCI).

Refer to Chart 34. The mixed formula-CC bis(THP ether) compounds (Example 36, 0.590 g.) are hydrolyzed in 33 ml. of acetic acid-water-tetrahydrofuran (20:10:3) at about 25° C. overnight. The mixture is concentrated from toluene and then ethyl acetate. The residue is chromatographed on a HPLC column eluting with acetone-methylene chloride (3:2) to obtain, first, the (15R) title compound, 0.129 g. The (15R) compound has $R_f$ 0.38 and the (15S) compound has $R_f$ 0.27 (TLC on silica gel in acetone-methylene chloride (3:1)). The 15S compound has NMR peaks at 5.75–5.04, 4.32–3.03, 3.65, 2.66–1.31, and 1.17$\delta$, infrared absorption at 3450, 3000, 1740, 1430, 1360, 1200, 1150, 965, 920, and 900 cm$^{-1}$, and mass spectral lines at 671.4000, 686, 596, 581, 513, 506, 491, 423, 397, 333, 307, 243, and 217. The (15R) compound has very nearly the same spectral properties.

EXAMPLE 38

19-Hydroxy-19-methyl-PGE$_2$, Methyl Ester, and its (15R) Epimer (Formula CCIII)

Refer to Chart 34. The mixed formula-CC bis(THP ether) PGF$_{2\alpha}$ compounds (Example 36, 0.602 g.) are oxidized with Jones reagent following the procedure of Example 12, and then are hydrolyzed to replace THP blocking groups following the procedure of Example 37. The mixed C-15 epimers are separated by chromatography on a HPLC column, eluting with acetone-methylene chloride (1:1) to obtain, first, the 15R title compound, 0.119 g. and then the 15S title compound, 0.138 g. The 15R compound has $R_f$ 0.48 and the 15S compound has $R_f$ 0.36 (TLC on silica gel in acetone-methylene chloride (3:1)). The 15S compound has NMR peaks at 5.83–5.02, 4.56–3.33, 3.66, 3.04–1.34, and 1.20$\delta$, infrared absorption at 3450, 3000, 1740, 1430, 1360, 1300, 1230, 1150, 1070, 1000, 965, 900, and 760 cm$^{-1}$, and mass spectral lines at 597.3441, 581, 522, 507, 439, 349, 295, and 131. The 15R compound has very nearly the same spectral properties.

EXAMPLE 39

19-Hydroxy-19-methyl-PGF$_{2\alpha}$, Methyl Ester (Formula CCVI)

Refer to Chart 35. The formula-CLXXVI 9-silyl-11,15bis(THP ether)-19-keto compound (Example 21, 0.500 g.) in 50 ml. of benzene is treated at about 25° C. with 2.3 equivalents of trimethylaluminum added dropwise over one min. The mixture is stirred for 30 min. and then added to 50 ml. of saturated aqueous ammonium chloride and extracted with ethyl acetate. The organic phase is washed with brine, dried, and concentrated. The residue is chromatographed to yield the corresponding 19-hydroxy-19-methyl compound which is then deblocked in tetrahydrofuran-acetic acid-water (3:20:10) to yield the title compound, having the same properties as the product of Example 37.

EXAMPLE 40

15,19-Dimethyl-19-hydroxy-PGF$_{2\alpha}$, Methyl Ester and its (15R) Epimer (Formula CCVI)

Refer to Charts 30 and 35. As starting material there is used the formula-CXXVI products of Example 15, namely (15R,S)-15-methyl-19,20-didehydro-PGF$_{2\alpha}$, 11-tetrahydropyranyl ether, methyl ester (Example 15). After saponification and recovery as the free acid, the compound is treated first with the silylating agent, and then with dihydropyran in the presence of pyridine hydrochloride to form a formula-CLXXIV compound of Chart 30. Thereafter the 15-methyl 19-keto compound of formula CLXXVI is prepared using procedures described herein. Finally, following the steps of Chart 35, the title compounds are obtained and separated by silica gel chromatography using procedures described herein or known in the art.

EXAMPLE 41

19-Hydroxy-19-methyl-PGF$_{1\alpha}$, Methyl Ester, and its (15R) Epimer. (Formula CCXIII).

I. Refer to Chart 36. The mixed formula-CC bis(THP ether) of the PGF$_{2\alpha}$ compounds (Example 36, 1.5 g.) in 60 ml. of ethyl acetate are reduced at C$_5$–C$_6$ by hydrogenation at about 25° C. in the presence of 200 mg. of 5% palladium-on-carbon with slightly over the theory for one equivalent of hydrogen. The solids are filtered off and the filtrate concentrated to yield the corresponding formula-CCXII bis(THP ether) of the PGF$_{1\alpha}$ compounds having R$_f$ 0.28 (TLC on silica gel in acetone-Skellysolve B (1:2)).

II. The above compounds are hydrolyzed to the title compounds following the procedure of Example 37, thereafter separating them by HPLC eluting with acetone-methylene chloride (1:1). The (15S) title compound has R$_f$ 0.23 (TLC on silica gel in acetone-Skellysolve B (3:1)), NMR peaks at 5.85–5.05, 4.52–3.23, 3.67, 2.68–1.27, and 1.19$\delta$, infrared absorption at 3450, 3000, 1740, 1440, 1360, 970, and 900 cm$^{-1}$, and high resolution mas spectral line at 688.4380. The (15R) title compound has R$_f$ 0.29 (TLC on silica gel in acetone-Skellysolve B (3:1)), NMR peaks at 5.85–5.09, 4.33–3.0, 3.65, 2.68–1.28, and 1.20$\delta$, infrared absorption at 3450, 2950, 1740, 1440, 1360, 970, 905, 825, and 765 cm$^{-1}$, and high resolution mass spectral line at 688.4394.

EXAMPLE 42

19-Hydroxy-19-methyl-PGE$_1$, Methyl Ester and its (15R) Epimer. (Formula CCXV).

Refer to Chart 36. The formula-CCXII bis(THP ether) of the PGF$_{1\alpha}$ compounds (Example 41, 0.900 g.) are oxidized with Jones reagent following the procedure of Example 33 and then are hydrolyzed to replace THP blocking groups following the procedure of Example 37. The mixed C-15 epimers are separated by chromatography on a HPLC column, eluting with acetone-methylene chloride (1:1). The (15S) compound has R$_f$ 0.33 (TLC on silica gel in acetone-methylene chloride (2:1)), NMR peaks at 5.80–5.40, 4.55–3.33, 3.65, 3.00–0.80, and 1.20$\delta$, infrared absorption at 3450, 2950, 1740, 1430, 1360, 1240, 1150, 1070, 1040, 1000, 965, 910, and 730 cm$^{-1}$, and high resolution mass spectral line at 599.3590. The (15R) compound has R$_f$ 0.39 (TLC on silica gel in acetone-methylene chloride (2:1)), NMR peaks at 5.85–5.52, 4.38–3.58, 3.67, 3.58–2.81, 2.81–1.03, and 1.20$\delta$, infrared absorption at 3450, 2950, 1740, 1430, 1260, 1150, 1070, and 965 cm$^{-1}$, and high resolution mass spectral line at 628,3900.

EXAMPLE 43

19-Hydroxy-19-methyl-13,14-dihydro-(15R)-PGE$_1$, Methyl Ester.

The formula-CCXV 19-hydroxy-19-methyl-(15R)-PGE$_1$, methyl ester (Example 42, 0.148 g.) is hydrogenated again over 5% palladium-on-carbon, following the procedure of Example 41. The product is chromatographed by HPLC, eluting with acetone-methylene chloride (1:2) to yield the title compound, 0.031 g. having R$_f$ 0.35 (TLC on silica gel in acetone-methylene chloride (2:1)), NMR peaks at 4.44–3.60, 3.66, 3.46–3.08, 2.96–1.08, and 1.21$\delta$, infrared absorption at 3500, 3000, 1740, 1430, 1270, and 1150, and high resolution mass spectral peak at 601.3797.

EXAMPLE 44

19-Hydroxy-19-methyl-13,14-dihydro-(15S)-PGE$_1$, Methyl Ester

The formula-CCXIII 19-hydroxy-19-methyl-PGE$_1$, methyl ester (Example 42, 0.179 g.) is converted to its bis(THP ether) and hydrogenated again following the procedure of Example 41. Thereafter the THP groups are replaced by hydrolysis and the product chromatographed by HPLC eluting with acetone-methylene chloride (2:3) to yield the title compound, 0.031 g. The compound has R$_f$ 0.41 (TLC on silica gel in acetone-methylene chloride (2:1)), and spectral data similar to that for the 15R epimer (Example 43).

EXAMPLE 45

2-Decarboxy-2-hydroxymethyl-19-hydroxy-19-methyl-PGF$_{2\alpha}$, 11,15-bis(tetrahydropyran-2-yl ether), Mixed C-15 Epimers. (Formula CCLXVII)

Refer to Chart 46. The formula-CCLXVI 19-hydroxy-19-methyl-PGF$_{2\alpha}$, methyl ester, 11,15-bis(tetrahydropyran-2-yl ether) (Example 36, 1.98 g.) in 65 ml. of ether is added dropwise in 20 min. to a stirred suspension of lithium aluminum hydride (0.530 g.) in 130 ml. of ether at about 25° C. The mixture is stirred for 2.5 hr. and then quenched by careful addition of saturated sodium sulfate solution. There is then added 400 ml. of ether and 10–12 g. of powdered anhydrous sodium sulfate and, after about 30 min. stirring, the solids are filtered off and the filtrate is concentrated to yield the title compounds. They have R$_f$ 0.30 (TLC on silica gel in ethyl acetate) and NMR peaks at 5.82–5.00, 4.86–4.57, 4.36–3.17, 2.88–1.31, and 1.19$\delta$.

EXAMPLE 46

2-Decarboxy-2-hydroxymethyl-19-hydroxy-19-methyl-PGF$_{2\alpha}$ and its (15R) Epimer. (Formula CCLXVIII).

Refer to Chart 46. Following the procedures of Example 37 the bis(THP ether) compounds of Example 45 are hydrolyzed and chromatographed to yield the title compounds.

EXAMPLE 47

2-Decarboxy-2-hydroxymethyl-19-hydroxy-19-methyl-PGE$_2$ and its (15R) Epimer. (Formula CCLXXI).

I. Refer to Chart 46. There are first prepared the formula-CCLXIX monosilyl compounds. The formula-CCLXVII bis(THP ether) compounds (Example 45, 1.88 g.) in 18 ml. of dimethylformamide are treated at 0° C. with imidazole (0.332 g.) and t-butyldimethylsilyl chloride (0.529 g.). After 40 min. there is added ice-water (200 ml.) and ether (200 ml.) and the layers are separated. The organic phase is washed with water, dried, and concentrated. The residue is chromatographed on a HPLC column, eluting with ethyl acetate-Skellysolve B (2:3) to yield the mixed formula-CCLXIX monosilyl compounds, 1.8 g., having $R_f$ 0.27 (TLC on silica gel in acetone-methylene chloride (1:6)).

II. The above compounds are oxidized with Collins reagent prepared from pyridine (3.05 g.) in 65 ml. of methylene chloride and chromic anhydride (1.93 g.). The above compounds (1.8 g.) in 40 ml. of methylene chloride are added dropwise over 8 min. to the reagent to 0° C. Thereafter the mixture is stirred at about 25° C. for one hr., diluted with ether and filtered. The filtrate is concentrated to yield the title compounds as their 1-silyl, 11,15-bis(THP ether) derivatives of formula CCLXX. The blocking groups are replaced by hydrolysis in 66 ml. of acetic acid-water-tetrahydrofuran (20:10:3) at about 25° C. for 16 hr. and finally at about 40° C. for 4 hr. The products are separated by HPLC chromatography, eluting with acetone-methylene chloride (1:1) to yield the (15R) compound, 0.332 g., having $R_f$ 0.20 (in acetone-methylene chloride (2:1)) NMR peaks at 5.88–5.08, 4.48–3.36, 3.20–2.84, 2.78–1.35, and 1.20$\delta$, infrared absorption at 3450, 2950, 1730, 1360, 1230, 1150, 1060, 1040, 965, 920, 840, 820, and 760 cm$^{-1}$, and mass spectral lines at 641.566, 551, 483, 476, 393, 339, and 131. The (15S) compound, 0.417 g., has $R_f$ 0.13, NMR peaks at 5.98–5.03, 4.66–3.21, 3.04–1.33 and 1.20$\delta$, and infrared and mass spectral properties similar to those of the (15R) compound.

EXAMPLE 48

2-Decarboxy-2-hydroxymethyl-19-hydroxy-19-methyl-PGE$_1$ and its (15R) Epimers.

Following the procedures of Examples 45 and 47, the mixed 15-epimers of 19-hydroxy-19-methyl-PGF$_{1\alpha}$, methyl ester, as their 11,15-bis(THP ethers) (Example 41-I, 0.726 g.) are reduced first to their 2-decarboxy-2-hydroxymethyl counterparts. There are next prepared the corresponding mono-silyl bis(THP ether) compounds, which are oxidized with Collins reagent to form the PGE compounds. Finally, the blocking groups are replaced by hydrolysis to yield the title compounds. The (15R) compound, 0.130 g., has $R_f$ 0.35 (TLC on silica gel in acetone-methylene chloride (1:1)), NMR peaks at 5.84–5.29, 4.83–3.05, 2.95–1.96, and 1.17$\delta$, infrared absorption at 3400, 2950, 1740, 1460, 1370, 1230, 1150, 1070, 970, 900, and 765 cm$^{-1}$, and high resolution mass spectral peak at 643.4037. The (15S) compound, 0.115 g., has $R_f$ 0.26, NMR peaks at 5.82–5.26, 4.92–3.03, 2.93–1.25, and 1.15$\delta$, and infrared absorption similar to the 15(R) compound.

Following the procedures disclosed herein, but substituting the appropriate starting materials, intermediates, and reagents as are apparent to those skilled in the art, there are prepared the following compounds within the scope of this invention:

I. 19,20-DIDEHYDRO($\Delta^{19}$) PROSTAGLANDIN-TYPE COMPOUNDS OF FORMULA III A. Wherein R$_1$ is —COOR$_6$ 19,20-didehydro-PGF$_{2\alpha}$, methyl ester,
16,16-dimethyl-19,20-didehydro-PGF$_{2\alpha}$, methyl ester,
16,16-difluoro-19,20-didehydro-PGF$_{2\alpha}$, methyl ester,
(15S)-15-methyl-19,20-didehydro-PGF$_{2\alpha}$, methyl ester,
(15R)-15-methyl-19,20-didehydro-PGF$_{2\alpha}$, methyl ester,
13,14-cis-19,20-didehydro-PGF$_{2\alpha}$, methyl ester,
13,14,19,20-tetradehydro-PGF$_{2\alpha}$, methyl ester,
2,2-difluoro-19,20-didehydro-PGF$_{2\alpha}$, methyl ester,
2,2,16,16-tetrafluoro-19,20-didehydro-PGF$_{2\alpha}$, methyl ester,
2,2-difluoro-(15S)-15-methyl-19,20-didehydro-PGF$_{2\alpha}$, methyl ester,
2,2-difluoro-(15R)-15-methyl-19,20-didehydro-PGF$_{2\alpha}$, methyl ester,
2,2-difluoro-13,14-dihydro-19,20-didehydro-PGF$_{2\alpha}$, methyl ester,
4,5,19,20-tetradehydro-PGF$_{1\alpha}$, methyl ester,
4,5,19,20-tetradehydro-16,16-difluoro-PGF$_{1\alpha}$, methyl ester,
4,5,19,20-tetradehydro-(15S)-15-methyl-PGF$_{1\alpha}$, methyl ester,
4,5,19,20-tetradehydro-(15R)-15-methyl-PGF$_{1\alpha}$, methyl ester,
2,3,19,20-tetradehydro-PGF$_{1\alpha}$, methyl ester,
2,3,19,20-tetradehydro-16,16-difluoro-PGF$_{1\alpha}$, methyl ester,
2,3,19,20-tetradehydro-(15S)-15-methyl-PGF$_{1\alpha}$, methyl ester,
2,3,19,20-tetradehydro-(15R)-15-methyl-PGF$_{1\alpha}$, methyl ester,
2,3,19,20-tetradehydro-13,14-cis-PGF$_{1\alpha}$, methyl ester,
2,3,19,20-tetradehydro-13,14-cis-16,16-dimethyl-PGF$_{1\alpha}$, methyl ester,
2,3,19,20-tetradehydro-13,14-cis-16,16-difluoro-PGF$_{1\alpha}$, methyl ester,
2,3,19,20-tetradehydro-13,14-dihydro-PGF$_{1\alpha}$, methyl ester,
19,20-didehydro-PGF$_{1\alpha}$, methyl ester,
(15S)-15-methyl-19,20-didehydro-PGF$_{1\alpha}$, methyl ester,
(15R)-15-methyl-19,20-didehydro-PGF$_{1\alpha}$, methyl ester,
13,14-cis-19,20-didehydro-PGF$_{1\alpha}$, methyl ester,
13,14-cis-16,16-difluoro-19,20-didehydro-PGF$_{1\alpha}$, methyl ester,
13,14-cis-(15S)-15-methyl-19,20-didehydro-PGF$_{1\alpha}$, methyl ester,
13,14-cis-(15R)-15-methyl-19,20-didehydro-PGF$_{1\alpha}$, methyl ester,
13,14,19,20-tetradehydro-PGF$_{1\alpha}$, methyl ester,
13,14,19,20-tetradehydro-16,16-dimethyl-PGF$_{1\alpha}$, methyl ester,
13,14,19,20-tetradehydro-16,16-difluoro-PGF$_{1\alpha}$, methyl ester,
13,14-dihydro-19,20-didehydro-PGF$_{1\alpha}$, methyl ester,
13,14-dihydro-16,16-dimethyl-19,20-didehydro-PGF$_{1\alpha}$, methyl ester,
13,14-dihydro-16,16-difluoro-19,20-didehydro-PGF$_{1\alpha}$, methyl ester,
13,14-dihydro-(15S)-15-methyl-19,20-didehydro-PGF$_{1\alpha}$, methyl ester,
13,14-dihydro-(15R)-15-methyl-19,20-didehydro-PGF$_{1\alpha}$, methyl ester,
2,2-difluoro-19,20-didehydro-PGF$_{1\alpha}$, methyl ester, 2,2,16,16-tetrafluoro-19,20-didehydro-PGF$_{1\alpha}$, methyl ester,
2,2-difluoro-(15S)-15-methyl-19,20-didehydro-PGF$_{1\alpha}$, methyl ester,
2,2-difluoro-(15R)-15-methyl-19,20-didehydro-PGF$_{1\alpha}$, methyl ester,
2,2-difluoro-13,14-dihydro-19,20-didehydro-PGF$_{1\alpha}$, methyl ester,
3-oxa-19,20-didehydro-PGF$_{1\alpha}$, methyl ester,
3-oxa-16,16-dimethyl-19,20-didehydro-PGF$_{1\alpha}$, methyl ester,
3-oxa-13,14-cis-19,20-didehydro-PGF$_{1\alpha}$, methyl ester,
3-oxa-13,14,19,20-tetradehydro-PGF$_{1\alpha}$, methyl ester,
3-oxa-13,14-dihydro-19,20-didehydro-PGF$_{1\alpha}$, methyl ester,
5-oxa-19,20-didehydro-PGF$_{1\alpha}$, methyl ester,
5-oxa-16,16-dimethyl-19,20-didehydro-PGF$_{1\alpha}$, methyl ester,
5-oxa-13,14-cis-19,20-didehydro-PGF$_{1\alpha}$, methyl ester,
5-oxa-13,14,19,20-tetradehydro-PGF$_{1\alpha}$, methyl ester,
5-oxa-13,14-dihydro-19,20-didehydro-PGF$_{1\alpha}$, methyl ester,
3-oxa-3,7-inter-m-phenylene-4,5,6-trinor-19,20-didehydro-PGF$_{1\alpha}$, methyl ester,
3-oxa-3,7-inter-m-phenylene-4,5,6-trinor-16,16-dimethyl-19,20-didehydro-PGF$_{1\alpha}$, methyl ester,
3-oxa-3,7-inter-m-phenylene-4,5,6-trinor-16,16-difluoro-19,20-didehydro-PGF$_{1\alpha}$, methyl ester,
3-oxa-3,7-inter-m-phenylene-4,5,6-trinor-(15S)-15-methyl-19,20-didehydro-PGF$_{1\alpha}$, methyl ester,
3-oxa-3,7-inter-m-phenylene-4,5,6-trinor-(15R)-15-methyl-19,20-didehydro-PGF$_{1\alpha}$, methyl ester,
3-oxa-3,7-inter-m-phenylene-4,5,6-trinor-13,14,19,20-tetradehydro-PGF$_{1\alpha}$, methyl ester,
3-oxa-3,7-inter-m-phenylene-4,5,6-trinor-16,16-difluoro-13,14,19,20-tetradehydro-PGF$_{1\alpha}$, methyl ester,
11-deoxy-19,20-didehydro-PGF$_{2\alpha}$, methyl ester,
11-deoxy-16,16-dimethyl-19,20-didehydro-PGF$_{2\alpha}$, methyl ester,
11-deoxy-16,16-difluoro-19,20-didehydro-PGF$_{2\alpha}$, methyl ester,
11-deoxy-(15S)-15-methyl-19,20-didehydro-PGF$_{2\alpha}$, methyl ester,
11-deoxy-(15R)-15-methyl-19,20-didehydro-PGF$_{2\alpha}$, methyl ester,
11-deoxy-13,14-cis-19,20-didehydro-PGF$_{2\alpha}$, methyl ester,
11-deoxy-13,14,19,20-tetradehydro-PGF$_{2\alpha}$, methyl ester,
11-deoxy-2,2-difluoro-19,20-didehydro-PGF$_{2\alpha}$, methyl ester,
11-deoxy-2,2,16,16-tetrafluoro-19,20-didehydro-PGF$_{2\alpha}$, methyl ester,
11-deoxy-2,2-difluoro-(15S)-15-methyl-19,20-didehydro-PGF$_{2\alpha}$, methyl ester,
11-deoxy-2,2-difluoro-(15R)-15-methyl-19,20-didehydro-PGF$_{2\alpha}$, methyl ester,
11-deoxy-2,2-difluoro-19,20-didehydro-PGF$_{1\alpha}$, methyl ester,
11-deoxy-4,5,19,20-tetradehydro-PGF$_{1\alpha}$, methyl ester,
11-deoxy-4,5,19,20-tetradehydro-16,16-difluoro-PGF$_{1\alpha}$, methyl ester,
11-deoxy-(15S)-15-methyl-4,5,19,20-tetradehydro-PGF$_{1\alpha}$, methyl ester,
11-deoxy-(15R)-15-methyl-4,5,19,20-tetradehydro-PGF$_{1\alpha}$, methyl ester,
11-deoxy-2,3,19,20-tetradehydro-PGF$_{1\alpha}$, methyl ester,
11-deoxy-2,3,19,20-tetradehydro-16,16-difluoro-PGF$_{1\alpha}$, methyl ester,
11-deoxy-2,3,19,20-tetradehydro-(15S)-15-methyl-PGF$_{1\alpha}$, methyl ester,
11-deoxy-2,3,19,20-tetradehydro-(15R)-15-methyl-PGF$_{1\alpha}$, methyl ester,
11-deoxy-2,3,19,20-tetradehydro-13,14-cis-PGF$_{1\alpha}$, methyl ester,
11-deoxy-2,3,19,20-tetradehydro-13,14-cis-16,16-dimethyl-PGF$_{1\alpha}$, methyl ester,
11-deoxy-2,3,19,20-tetradehydro-13,14-cis-16,16-difluoro-PGF$_{1\alpha}$, methyl ester,
11-deoxy-2,3,19,20-tetradehydro-13,14-dihydro-PGF$_{1\alpha}$, methyl ester,
11-deoxy-19,20-didehydro-PGF$_{1\alpha}$, methyl ester,
11-deoxy-(15S)-15-methyl-19,20-didehydro-PGF$_{1\alpha}$, methyl ester,
11-deoxy-(15R)-15-methyl-19,20-didehydro-PGF$_{1\alpha}$, methyl ester,
11-deoxy-13,14-cis-19,20-didehydro-PGF$_{1\alpha}$, methyl ester,
11-deoxy-13,14-cis-16,16-difluoro-19,20-didehydro-PGF$_{1\alpha}$, methyl ester,
11-deoxy-13,14-cis-(15S)-15-methyl-19,20-didehydro-PGF$_{1\alpha}$, methyl ester,
11-deoxy-13,14-cis-(15R)-15-methyl-19,20-didehydro-PGF$_{1\alpha}$, methyl ester,
11-deoxy-13,14,19,20-tetradehydro-PGF$_{1\alpha}$, methyl ester,
11-deoxy-13,14,19,20-tetradehydro-16,16-dimethyl-PGF$_{1\alpha}$, methyl ester,
11-deoxy-11$\alpha$-hydroxymethyl-19,20-didehydro-PGF$_{2\alpha}$, methyl ester,
11-deoxy-11$\alpha$-hydroxymethyl-16,16-dimethyl-19,20-didehydro-PGF$_{2\alpha}$, methyl ester,
11-deoxy-11$\alpha$-hydroxymethyl-16,16-difluoro-19,20-didehydro-PGF$_{2\alpha}$, methyl ester,
11-deoxy-11$\alpha$-hydroxymethyl-(15S)-15-methyl-19,20-didehydro-PGF$_{2\alpha}$, methyl ester,
11-deoxy-11$\alpha$-hydroxymethyl-(15R)-15-methyl-19,20-didehydro-PGF$_{2\alpha}$, methyl ester,
11-deoxy-11$\alpha$-hydroxymethyl-13,14-cis-19,20-didehydro-PGF$_{2\alpha}$, methyl ester,
11-deoxy-11$\alpha$-hydroxymethyl-13,14,19,20-tetradehydro-PGF$_{2\alpha}$, methyl ester,
11-deoxy-11$\alpha$-hydroxymethyl-2,2-difluoro-19,20-didehydro-PGF$_{2\alpha}$, methyl ester,
11-deoxy-11$\alpha$-hydroxymethyl-2,2,16,16-tetrafluoro-19,20-didehydro-PGF$_{2\alpha}$, methyl ester,
11-deoxy-11$\alpha$-hydroxymethyl-2,2-difluoro-(15S)-15-methyl-19,20-didehydro-PGF$_{2\alpha}$, methyl ester,
11-deoxy-11$\alpha$-hydroxymethyl-2,2-difluoro-(15R)-15-methyl-19,20-didehydro-PGF$_{2\alpha}$, methyl ester,
11-deoxy-11$\alpha$-hydroxymethyl-2,2-difluoro-19,20-didehydro-PGF$_{2\alpha}$, methyl ester,
11-deoxy-11$\alpha$-hydroxymethyl-4,5,19,20-tetradehydro-PGF$_{1\alpha}$, methyl ester,
11-deoxy-11$\alpha$-hydroxymethyl-4,5,19,20-tetradehydro-16,16-difluoro-PGF$_{1\alpha}$, methyl ester,
11-deoxy-11$\alpha$-hydroxymethyl-(15S)-15-methyl-4,5,19,20-tetradehydro-PGF$_{1\alpha}$, methyl ester,
11-deoxy-11$\alpha$-hydroxymethyl-(15R)-15-methyl-4,5,19,20-tetradehydro-PGF$_{1\alpha}$, methyl ester, 11-deoxy-11α-hydroxymethyl-2,3,19,20-tetrahydro-PGF$_{1α}$, methyl ester, Likewise following the procedures disclosed herein, there are prepared the corresponding 19,20-didehydro-PGF$_β$, -PGE, and -9-deoxo-9-methylene-PGE methyl ester compounds within the scope of formula III.

Also following the procedures disclosed herein, there are prepared the corresponding free acid from each of the above methyl esters and, likewise, the corresponding sodium salt.

B. Wherein R$_1$ is —CH$_2$OH.

2-decarboxy-2-hydroxymethyl-19,20-didehydro-PGF$_{2α}$,
2-decarboxy-2-hydroxymethyl-4,5,19,20-tetradehydro-PGF$_{1α}$,
2-decarboxy-2-hydroxymethyl-(15S)-15-methyl-4,5,19,20-tetradehydro-PGF$_{1α}$,
2-decarboxy-2-hydroxymethyl-(15R)-15-methyl-4,5,19,20-tetradehydro-PGF$_{1α}$,
2-decarboxy-2-hydroxymethyl-4,5,13,14,19,20-hexadehydro-PGF$_{1α}$,
2-decarboxy-2-hydroxymethyl-4,5,13,14,19,20-hexadehydro-16,16-difluoro-PGF$_{1α}$,
2-decarboxy-2-hydroxymethyl-2,3,19,20-tetradehydro-PGF$_{1α}$,
2-decarboxy-2-hydroxymethyl-2,3,19,20-tetradehydro-16,16-difluoro-PGF$_{1α}$,
2-decarboxy-2-hydroxymethyl-2,3,19,20-tetradehydro-15(S)-15-methyl-PGF$_{1α}$,
2-decarboxy-2-hydroxymethyl-2,3,19,20-tetradehydro-15(R)-15-methyl-PGF$_{1α}$,
2-decarboxy-2-hydroxymethyl-19,20-didehydro-PGF$_{1α}$,
2-decarboxy-2-hydroxymethyl-16,16-dimethyl-19,20-didehydro-PGF$_{1α}$,
2-decarboxy-2-hydroxymethyl-16,16-difluoro-19,20-didehydro-PGF$_{1α}$,
2-decarboxy-2-hydroxymethyl-13,14-dihydro-19,20-didehydro-PGF$_{1α}$,
2-decarboxy-2-hydroxymethyl-11-deoxy-19,20-didehydro-PGF$_{2α}$,
2-decarboxy-2-hydroxymethyl-11-deoxy-4,5,19,20-tetradehydro-PGF$_{1α}$,
2-decarboxy-2-hydroxymethyl-11-deoxy-(15S)-15-methyl-4,5,19,20-tetradehydro-PGF$_{1α}$,
2-decarboxy-2-hydroxymethyl-11-deoxy-(15R)-15-methyl-4,5,19,20-tetradehydro-PGF$_{1α}$,
2-decarboxy-2-hydroxymethyl-11-deoxy-4,5,13,14,19,20-hexadehydro-PGF$_{1α}$,
2-decarboxy-2-hydroxymethyl-11-deoxy-4,5,13,14,19,20-hexadehydro-16,16-difluoro-PGF$_{1α}$,
2-decarboxy-2-hydroxymethyl-11-deoxy-2,3,19,20-tetradehydro-PGF$_{1α}$,
2-decarboxy-2-hydroxymethyl-11-deoxy-2,3,19,20-tetradehydro-16,16-difluoro-PGF$_{1α}$,
2-decarboxy-2-hydroxymethyl-11-deoxy-2,3,19,20-tetradehydro-(15R)-15-methyl-PGF$_{1α}$,
2-decarboxy-2-hydroxymethyl-11-deoxy-2,3,19,20-tetradehydro-(15S)-15-methyl-PGF$_{1α}$,
2-decarboxy-2-hydroxymethyl-11-deoxy-19,20-didehydro-PGF$_{1α}$,
2-decarboxy-2-hydroxymethyl-11-deoxy-16,16-dimethyl-19,20-didehydro-PGF$_{1α}$,
2-decarboxy-2-hydroxymethyl-11-deoxy-16,16-difluoro-19,20-didehydro-PGF$_{1α}$,
2-decarboxy-2-hydroxymethyl-11-deoxy-13,14-dihydro-19,20-didehydro-PGF$_{1α}$,
2-decarboxy-2-hydroxymethyl-11-deoxy-11α-hydroxymethyl-19,20-didehydro-PGF$_{2α}$,
2-decarboxy-2-hydroxymethyl-11-deoxy-11α-hydroxymethyl-4,5,19,20-tetradehydro-PGF$_{1α}$,
2-decarboxy-2-hydroxymethyl-11-deoxy-11α-hydroxymethyl-(15S)-15-methyl-4,5,19,20-tetradehydro-PGF$_{1α}$,
2-decarboxy-2-hydroxymethyl-11-deoxy-11α-hydroxymethyl-(15R)-15-methyl-4,5,19,20-tetradehydro-PGF$_{1α}$,
2-decarboxy-2-hydroxymethyl-11-deoxy-11α-hydroxymethyl-4,5,13,14,19,20-hexadehydro-PGF$_{1α}$,
2-decarboxy-2-hydroxymethyl-11-deoxy-11α-hydroxymethyl-4,5,13,14,19,20-hexadehydro-16,16-difluoro-PGF$_{1α}$,
2-decarboxy-2-hydroxymethyl-11-deoxy-11α-hydroxymethyl-2,3,19,20-tetradehydro-PGF$_{1α}$,
2-decarboxy-2-hydroxymethyl-11-deoxy-11α-hydroxymethyl-2,3,19,20-tetradehydro-16,16-difluoro-PGF$_{1α}$,
2-decarboxy-2-hydroxymethyl-11-deoxy-11α-hydroxymethyl-2,3,19,20-tetradehydro-(15S)-15-methyl-PGF$_{1α}$,
2-decarboxy-2-hydroxymethyl-11-deoxy-11α-hydroxymethyl-2,3,19,20-tetradehydro-(15R)-15-methyl-PGF$_{1α}$,
2-decarboxy-2-hydroxymethyl-11-deoxy-11α-hydroxymethyl-19,20-didehydro-PGF$_{1α}$,
2-decarboxy-2-hydroxymethyl-11-deoxy-11α-hydroxymethyl-16,16-dimethyl-19,20-didehydro-PGF$_{1α}$, Likewise following the procedures disclosed herein, there are prepared the corresponding 19,20-didehydro-PGF$_β$, -PGE, and 9-deoxo-9-methylene-PGE 2-decarboxy-2-hydroxymethyl compounds within the scope of formula III.

C. Wherein R$_1$ is —CH$_2$NH$_2$ 2-decarboxy-2-amino-19,20-didehydro-PGF$_{2α}$,
2-decarboxy-2-amino-(15S)-15-methyl-19,20-didehydro-PGF$_{2α}$,
2-decarboxy-2-amino-(15R)-15-methyl-19,20-didehydro-PGF$_{2α}$,
2-decarboxy-2-amino-2,3,19,20-tetradehydro-PGF$_{1α}$,
2-decarboxy-2-amino-2,3,19,20-tetradehydro-16,16-dimethyl-PGF$_{1α}$,
2-decarboxy-2-amino-2,3,19,20-tetradehydro-16,16-difluoro-PGF$_{1α}$,
2-decarboxy-2-amino-19,20-didehydro-PGF$_{1α}$,
2-decarboxy-2-amino-16,16-dimethyl-19,20-didehydro-PGF$_{1α}$,
2-decarboxy-2-amino-16,16-difluoro-19,20-didehydro-PGF$_{1α}$,
2-decarboxy-2-amino-11-deoxy-19,20-didehydro-PGF$_{1α}$,
2-decarboxy-2-amino-11-deoxy-(15S)-15-methyl-19,20-didehydro-PGF$_{2α}$,
2-decarboxy-2-amino-11-deoxy-(15R)-15-methyl-19,20-didehydro-PGF$_{2α}$,
2-decarboxy-2-amino-11-deoxy-2,3,19,20-tetradehydro-PGF$_{1α}$,
2-decarboxy-2-amino-11-deoxy-2,3,19,20-tetradehydro-16,16-dimethyl-PGF$_{1α}$, 2-decarboxy-2-amino-11-deoxy-2,3,19,20-tetradehydro-16,16-difluoro-PGF$_{1\alpha}$,
2-decarboxy-2-amino-11-deoxy-19,20-didehydro-PGF$_{1\alpha}$,
2-decarboxy-2-amino-11-deoxy-16,16-dimethyl-19,20-didehydro-PGF$_{1\alpha}$,
2-decarboxy-2-amino-11-deoxy-16,16-difluoro-19,20-didehydro-PGF$_{1\alpha}$,
2-decarboxy-2-amino-11-deoxy-11$\alpha$-hydroxymethyl-19,20-didehydro-PGF$_{2\alpha}$,
2-decarboxy-2-amino-11-deoxy-11$\alpha$-hydroxymethyl-(15S)-15-methyl-19,20-didehydro-PGF$_{2\alpha}$,
2-decarboxy-2-amino-11-deoxy-11$\alpha$-hydroxymethyl-(15R)-15-methyl-19,20-didehydro-PGF$_{2\alpha}$,
2-decarboxy-2-amino-11-deoxy-11$\alpha$-hydroxymethyl-2,3,19,20-tetradehydro-PGF$_{1\alpha}$,
2-decarboxy-2-amino-11-deoxy-11$\alpha$-hydroxymethyl-2,3,19,20-tetradehydro-16,16-dimethyl-PGF$_{1\alpha}$,
2-decarboxy-2-amino-11-deoxy-11$\alpha$-hydroxymethyl-2,3,19,20-tetradehydro-16,16-difluoro-PGF$_{1\alpha}$,
2-decarboxy-2-amino-11-deoxy-11$\alpha$-hydroxymethyl-19,20-didehydro-PGF$_{1\alpha}$,
2-decarboxy-2-amino-11-deoxy-11$\alpha$-hydroxymethyl-16,16-dimethyl-19,20-didehydro-PGF$_{1\alpha}$,
2-decarboxy-2-amino-11-deoxy-11$\alpha$-hydroxymethyl-16,16-difluoro-19,20-didehydro-PGF$_{1\alpha}$.

Likewise following the procedures disclosed herein, there are prepared the corresponding 19,20-didehydro-PGF$_{1\beta}$, -PGE$_1$, and 9-deoxo-9-methylene-PGE 2-decarboxy-2-amino compounds within the scope of formula III wherein R$_1$ is —CH$_2$NH$_2$.

D. Wherein R$_1$ is —C(O)—NH$_2$ 19,20-didehydro-PGF$_{2\alpha}$, amide,
2,2-difluoro-19,20-didehydro-PGF$_{2\alpha}$, amide,
4,5,19,20-tetradehydro-PGF$_{1\alpha}$, amide,
4,5,19,20-tetradehydro-(15S)-15-methyl-PGF$_{1\alpha}$, amide,
4,5,19,20-tetradehydro-(15R)-15-methyl-PGF$_{1\alpha}$, amide,
2,3,19,20-tetradehydro-PGF$_{1\alpha}$, amide,
2,3,19,20-tetradehydro-16,16-dimethyl-PGF$_{1\alpha}$, amide,
2,3,19,20-tetradehydro-16,16-difluoro-PGF$_{1\alpha}$, amide,
19,20-didehydro-PGF$_{1\alpha}$, amide,
16,16-dimethyl-19,20-didehydro-PGF$_{1\alpha}$, amide,
16,16-difluoro-19,20-didehydro-PGF$_{1\alpha}$, amide,
2,2-difluoro-19,20-didehydro-PGF$_{1\alpha}$, amide,
3-oxa-3,7-inter-m-phenylene-4,5,6-trinor-19,20-didehydro-PGF$_{1\alpha}$, amide,
3-oxa-3,7-inter-m-phenylene-4,5,6-trinor-(15S)-15-methyl-19,20-didehydro-PGF$_{1\alpha}$, amide,
3-oxa-3,7-inter-m-phenylene-4,5,6-trinor-(15R)-15-methyl-19,20-didehydro-PGF$_{1\alpha}$, amide,
3-oxa-3,7-inter-m-phenylene-4,5,6-trinor-13,14-dihydro-19,20-didehydro-PGF$_{1\alpha}$, amide,
11-deoxy-19,20-didehydro-PGF$_{2\alpha}$, amide,
11-deoxy-2,2-difluoro-19,20-didehydro-PGF$_{2\alpha}$, amide,
11-deoxy-4,5,19,20-tetradehydro-PGF$_{1\alpha}$, amide,
11-deoxy-4,5,19,20-tetradehydro-(15S)-15-methyl-PGF$_{1\alpha}$, amide,
11-deoxy-4,5,19,20-tetradehydro-(15R)-15-methyl-PGF$_{1\alpha}$, amide,
11-deoxy-2,3,19,20-tetradehydro-PGF$_{1\alpha}$, amide,
11-deoxy-2,3,19,20-tetradehydro-16,16-dimethyl-PGF$_{1\alpha}$, amide,
11-deoxy-2,3,19,20-tetradehydro-16,16-difluoro-PGF$_{1\alpha}$, amide,
11-deoxy-19,20-didehydro-PGF$_{1\alpha}$, amide,
11-deoxy-16,16-dimethyl-19,20-didehydro-PGF$_{1\alpha}$, amide,
11-deoxy-16,16-difluoro-19,20-didehydro-PGF$_{1\alpha}$, amide,
11-deoxy-2,2-difluoro-19,20-didehydro-PGF$_{1\alpha}$, amide,
11-deoxy-3-oxa-3,7-inter-m-phenylene-4,5,6-trinor-19,20-didehydro-PGF$_{1\alpha}$, amide,
11-deoxy-3-oxa-3,7-inter-m-phenylene-4,5,6-trinor-15(S)-15-methyl-19,20-didehydro-PGF$_{1\alpha}$, amide,
11-dexoy-3-oxa-3,7-inter-m-phenylene-4,5,6-trinor-15(R)-15-methyl-19,20-didehydro-PGF$_{1\alpha}$, amide,
11-deoxy-3-oxa-3,7-inter-m-phenylene-4,5,6-trinor-13,14-dihydro-19,20-didehydro-PGF$_{1\alpha}$, amide,
11-deoxy-11$\alpha$-hydroxymethyl-19,20-didehydro-PGF$_{2\alpha}$, amide,
11-deoxy-11$\alpha$-hydroxymethyl-2,2-difluoro-19,20-didehydro-PGF$_{2\alpha}$, amide,
11-deoxy-11$\alpha$-hydroxymethyl-4,5,19,20-tetradehydro-PGF$_{1\alpha}$, amide,
11-deoxy-11$\alpha$-hydroxymethyl-4,5,19,20-tetradehydro-15(S)-15-methyl-PGF$_{1\alpha}$, amide,
11-deoxy-11$\alpha$-hydroxymethyl-4,5,19,20-tetradehydro-15(R)-15-methyl-PGF$_{1\alpha}$, amide,
11-deoxy-11$\alpha$-hydroxymethyl-2,3,19,20-tetradehydro-PGF$_{1\alpha}$, amide,
11-deoxy-11$\alpha$-hydroxymethyl-2,3,19,20-tetradehydro-16,16-dimethyl-PGF$_{1\alpha}$, amide,
11-deoxy-11$\alpha$-hydroxymethyl-2,3,19,20-tetradehydro-16,16-difluoro-PGF$_{1\alpha}$, amide,
11-deoxy-11$\alpha$-hydroxymethyl-19,20-didehydro-PGF$_{1\alpha}$, amide,
11-deoxy-11$\alpha$-hydroxymethyl-16,16-dimethyl-19,20-didehydro-PGF$_{1\alpha}$, amide,
11-deoxy-11$\alpha$-hydroxymethyl-16,16-difluoro-19,20-didehydro-PGF$_{1\alpha}$, amide,
11-deoxy-11$\alpha$-hydroxymethyl-2,2-difluoro-19,20-didehydro-PGF$_{1\alpha}$, amide,
11-deoxy-11$\alpha$-hydroxymethyl-3-oxa-3,7-inter-m-phenylene-4,5,6-trinor-19,20-didehydro-PGF$_{1\alpha}$, amide,
11-deoxy-11$\alpha$-hydroxymethyl-3-oxa-3,7-inter-m-phenylene-4,5,6-trinor-(15S)-15-methyl-19,20-didehydro-PGF$_{1\alpha}$, amide,
11-deoxy-11$\alpha$-hydroxymethyl-3-oxa-3,7-inter-m-phenylene-4,5,6-trinor-(15R)-15-methyl-19,20-didehydro-PGF$_{1\alpha}$, amide,
11-deoxy-11$\alpha$-hydroxymethyl-3-oxa-3,7-inter-m-phenylene-4,5,6-trinor-13,14-dihydro-19,20-didehydro-PGF$_{1\alpha}$, amide.

Likewise following the procedures disclosed herein, there are prepared the corresponding 19,20-didehydro-PGF$_{1\beta}$, -PGE$_1$, and 9-deoxo-9-methylene-PGE amides within the scope of formula III wherein R$_1$ is —C(O)—NH$_2$.

E. Wherein R$_1$ is —C(O)NH—SO$_2$—CH$_3$.

19,20-didehydro-PGF$_{2\alpha}$, methanesulfonylamide,
16,16-dimethyl-19,20-didehydro-PGF$_{2\alpha}$, methanesulfonylamide,
2,3,19,20-tetradehydro-PGF$_{1\alpha}$, methanesulfonylamide, 2,3,19,20-tetradehydro-16,16-dimethyl-PGF$_{1\alpha}$, methanesulfonylamide, 2,3,19,20-tetradehydro-16,16-difluoro-PGF$_{1\alpha}$, methanesulfonylamide,
19,20-didehydro-PGF$_{1\alpha}$, methanesulfonylamide,
16,16-difluoro-19,20-didehydro-PGF$_{1\alpha}$, methanesulfonylamide,
11-deoxy-19,20-didehydro-PGF$_{2\alpha}$, methanesulfonylamide,
11-deoxy-16,16-dimethyl-19,20-didehydro-PGF$_{2\alpha}$, methanesulfonylamide,
11-deoxy-2,3,19,20-tetradehydro-PGF$_{1\alpha}$, methanesulfonylamide,
11-deoxy-2,3,19,20-tetradehydro-16,16-dimethyl-PGF$_{1\alpha}$, methanesulfonylamide,
11-deoxy-2,3,19,20-tetradehydro-16,16-difluoro-PGF$_{1\alpha}$, methanesulfonylamide,
11-deoxy-19,20-didehydro-PGF$_{1\alpha}$, methanesulfonylamide,
11-deoxy-16,16-difluoro-19,20-didehydro-PGF$_{1\alpha}$, methanesulfonylamide,
11-deoxy-11$\alpha$-hydroxymethyl-19,20-didehydro-PGF$_{2\alpha}$, methanesulfonylamide,
11-deoxy-11$\alpha$-hydroxymethyl-16,16-dimethyl-19,20-didehydro-PGF$_{2\alpha}$, methanesulfonylamide,
11-deoxy-11$\alpha$-hydroxymethyl-2,3,19,20-tetradehydro-PGF$_{1\alpha}$, methanesulfonylamide,
11-deoxy-11$\alpha$-hydroxymethyl-2,3,19,20-tetradehydro-16,16-dimethyl-PGF$_{1\alpha}$, methanesulfonylamide,
11-deoxy-11$\alpha$-hydroxymethyl-2,3,19,20-tetradehydro-16,16-difluoro-PGF$_{1\alpha}$, methanesulfonylamide,
11-deoxy-11$\alpha$-hydroxymethyl-19,20-didehydro-PGF$_{1\alpha}$, methanesulfonylamide,
11-deoxy-11$\alpha$-hydroxymethyl-16,16-difluoro-19,20-didehydro-PGF$_{1\alpha}$, methanesulfonylamide.

Likewise following the procedures disclosed herein, there are prepared the corresponding 19,20-didehydro-PGF$_{1\beta}$, -PGE$_1$, and 9-deoxo-9-methylene-PGE methanesulfonylamides within the scope of formula III wherein R$_1$ is —C(O)—NH—SO$_2$—CH$_3$.

II. 19-Hydroxy Prostaglandin-Type Compounds of Formula IV

For every 19,20-didehydro compound listed above, including tetradehydro or hexadehydro compounds having the 19,20-didehydro feature, there is a corresponding 19-hydroxy prostaglandin-type compound, (19R) or (19S), and the mixed (19R,S) or "19(+)" hydroxy compounds.

Following the procedures disclosed herein, all of the corresponding 19-hydroxy-PGF$_\alpha$, -PGF$_\beta$, -PGE, and -9-deoxo-9-methylene-PGE compounds within the scope of formula IV are prepared as follows:

A. Wherein R$_{19}$ is —COOR$_6$, specifically the methyl esters, free acids, and sodium salts; for example corresponding to 16,16-dimethyl-19,20-didehydro-PGF$_{2\alpha}$, methyl ester listed above there are:
16,16-dimethyl-(19R)-19-hydroxy-PGF$_{2\alpha}$, methyl ester,
16,16-dimethyl-(19S)-19-hydroxy-PGF$_{2\alpha}$, methyl ester,
16,16-dimethyl-(19R,S)-19-hydroxy-PGF$_{2\alpha}$, methyl ester.
B. Wherein R$_{19}$ is —CH$_2$OH.
C. Wherein R$_{19}$ is —CH$_2$NH$_2$.
D. Wherein R$_{19}$ is —C(O)—NH$_2$.
E. Wherein R$_{19}$ is —C(O)—NH—SO$_2$—CH$_3$.

III. 19-Keto Prostaglandin-Type Compounds of Formula V

For every 19,20-didehydro compound listed above, including tetradehydro or hexadehydro compounds having the 19,20-didehydro feature, there is a corresponding 19-keto prostaglandin-type compound.

Following the procedures disclosed herein, all of the corresponding 19-keto-PGF$_\alpha$, -PGF$_\beta$, -PGE, and 9-deoxo-9-methylene-PGE compounds within the scope of formula V are prepared as follows:

A. Wherein R$_{20}$ is —COOR$_6$, specifically the methyl esters, free acids, and sodium salts; for example corresponding to 16,16-difluoro-19,20-didehydro-PGF$_{2\alpha}$, methyl ester listed above there is:
16,16-difluoro-19-keto-PGF$_{2\alpha}$, methyl ester.
B. Wherein R$_{20}$ is —CH$_2$OH.
C. Wherein R$_{20}$ is —CH$_2$NH$_2$.
D. Wherein R$_{20}$ is —C(O)—NH$_2$.
E. Wherein R$_{20}$ is —C(O)—NH—SO$_2$—CH$_3$.

IV. 19-Hydroxy-19-Methyl Prostaglandin-Type Compounds of Formula VI

For every 19,20-didehydro compound listed above, including tetradehydro or hexadehydro compounds having the 19,20-didehydro feature, there is a corresponding 19-hydroxy-19-methyl prostaglandin-type compound.

Following the procedures disclosed herein, all of the corresponding 19-hydroxy-19-methyl-PGF$_\alpha$, -PGF$_\beta$, -PGE, and 9-deoxo-9-methylene-PGE compounds within the scope of formula VI are prepared, as follows:

A. Wherein R$_1$ is —COOR$_6$, specifically the methyl esters, free acids, and sodium salts; for example corresponding to 19,20-didehydro-PGF$_{2\alpha}$, methyl ester listed above there is
19-hydroxy-19-methyl-PGF$_{2\alpha}$, methyl ester.
B. Wherein R$_1$ is —CH$_2$OH.
C. Wherein R$_1$ is —CH$_2$NH$_2$.
D. Wherein R$_1$ is —C(O)—NH$_2$.
E. Wherein R$_1$ is —C(O)—NH—SO$_2$—CH$_3$.

FORMULAS

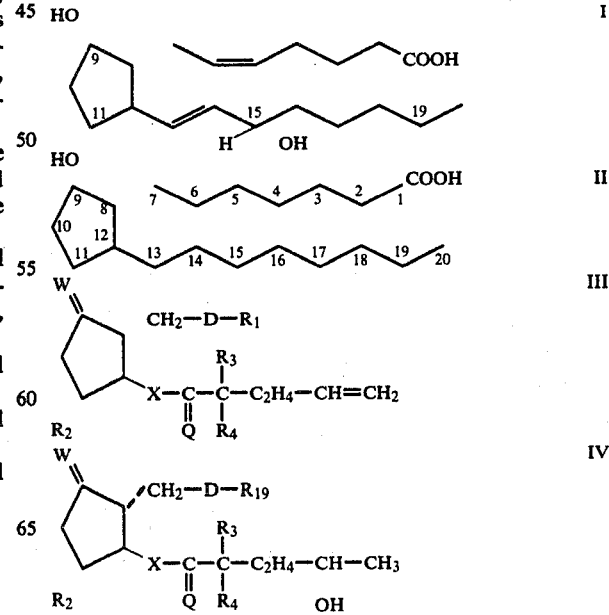

-continued
FORMULAS
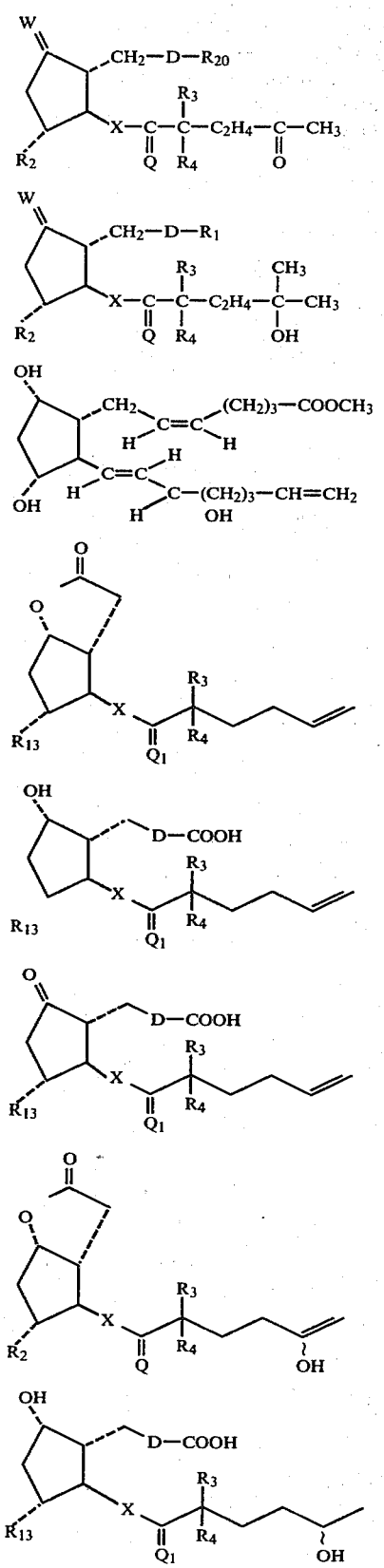
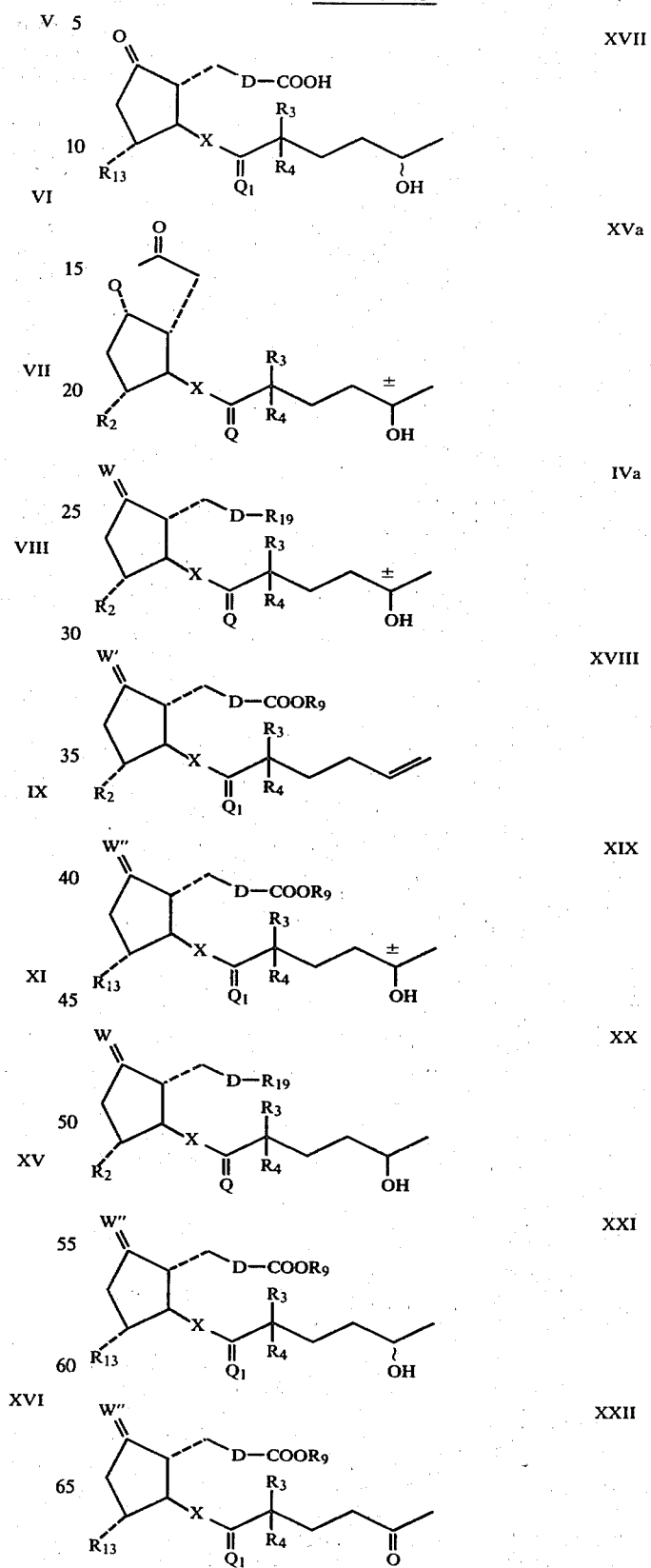

-continued
FORMULAS
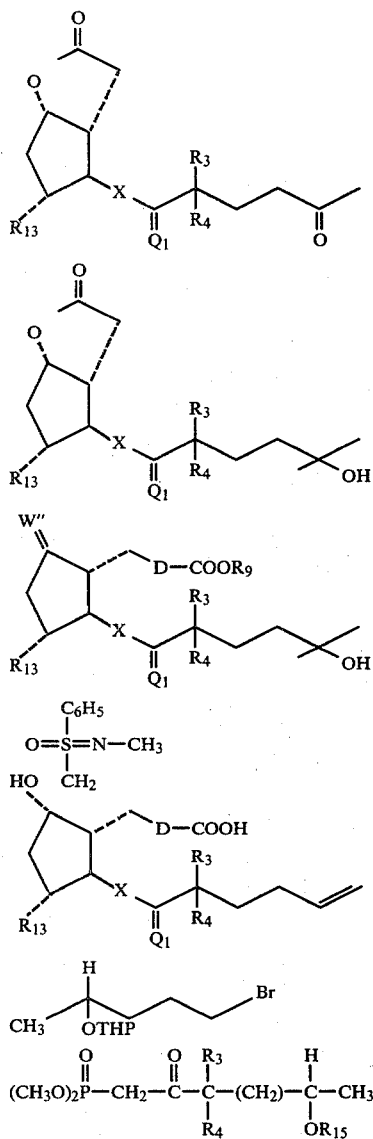
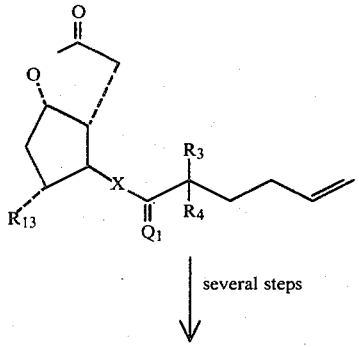
CHART 1
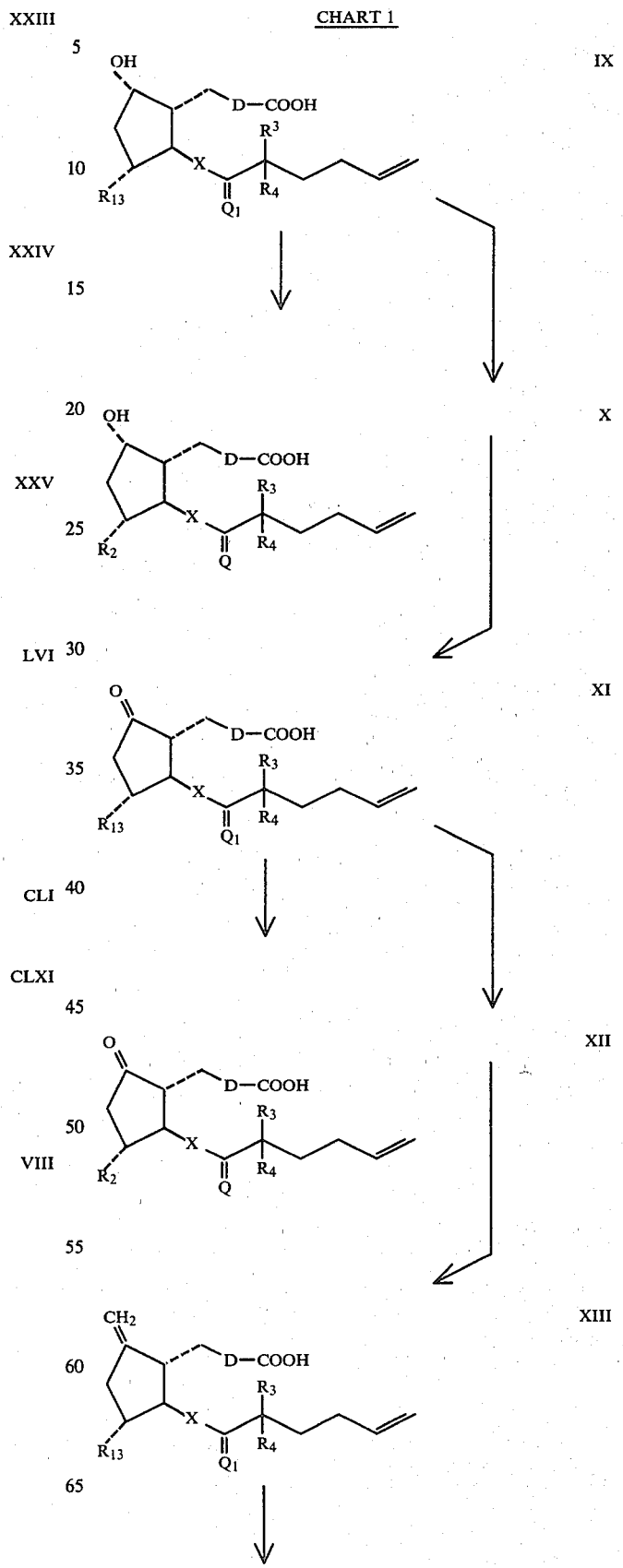

-continued
CHART 1
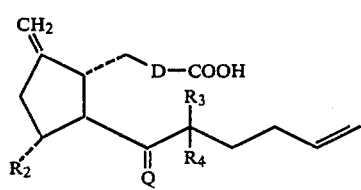
CHART 2
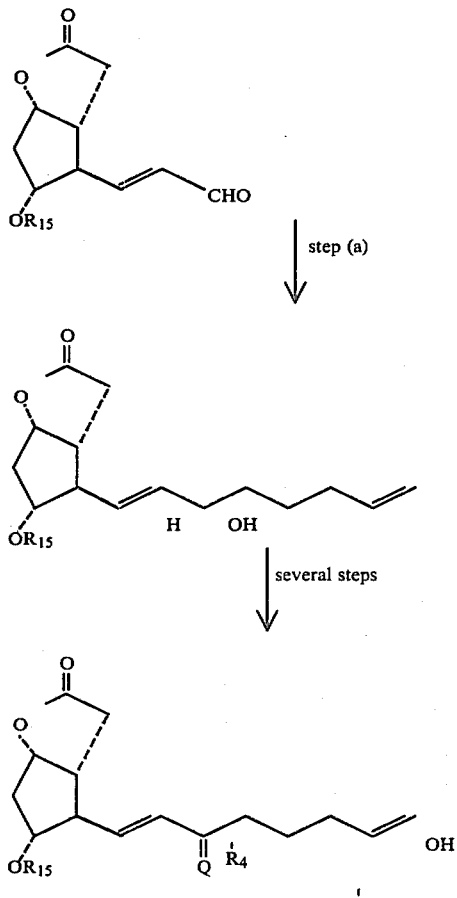
CHART 3
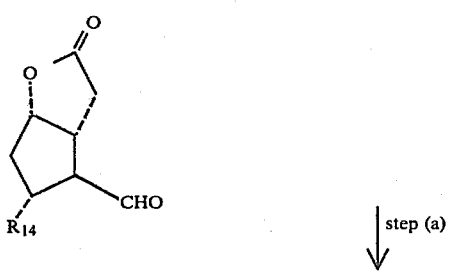
-continued
CHART 3
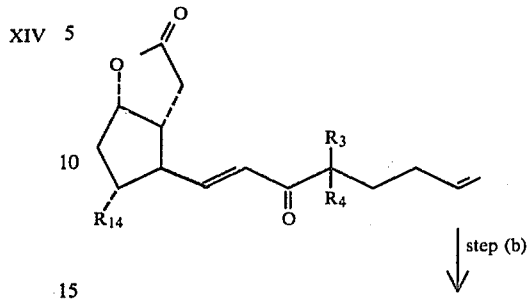 XXXVIII
↓ step (b)
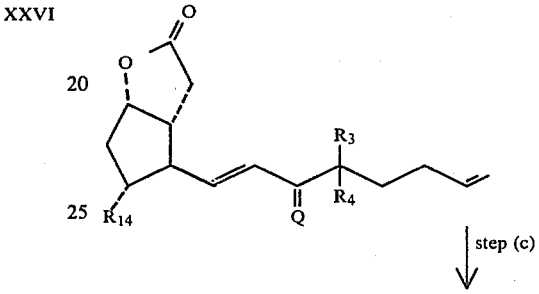 XXXIX
↓ step (c)
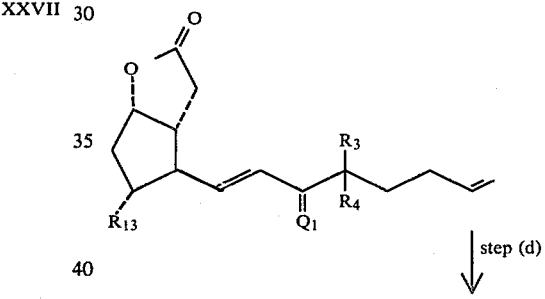 XL
↓ step (d)
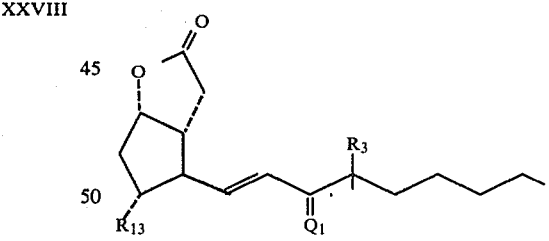 XLI
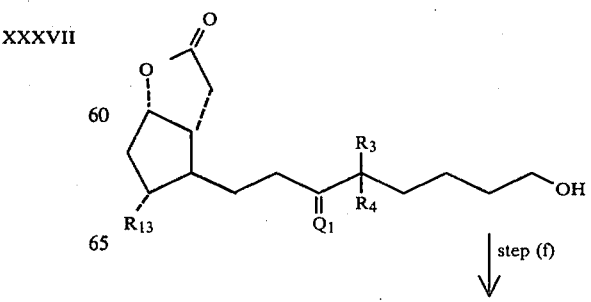 XLII
↓ step (f)

-continued
CHART 3
XLIII
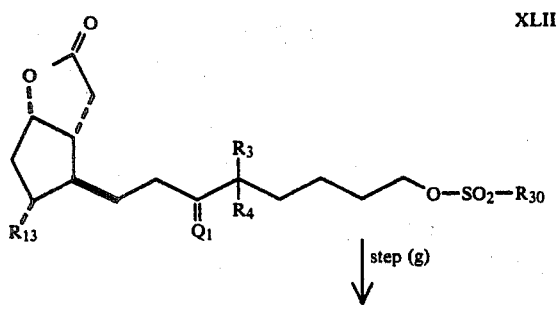
step (g)
XLIV
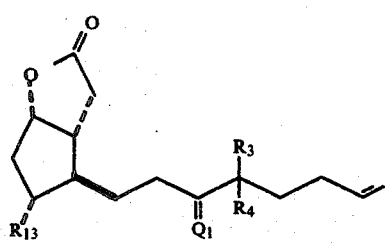
CHART 4
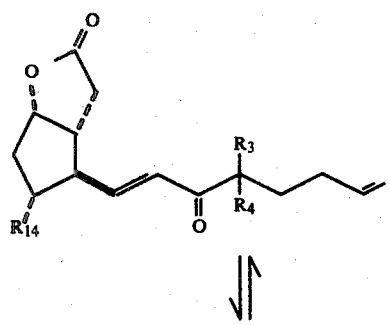
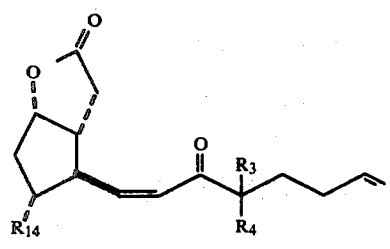
↓ several steps
XLVI
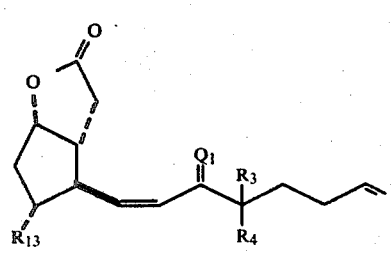
CHART 5
XXXVIII
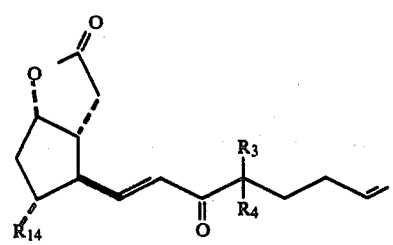
XLVII
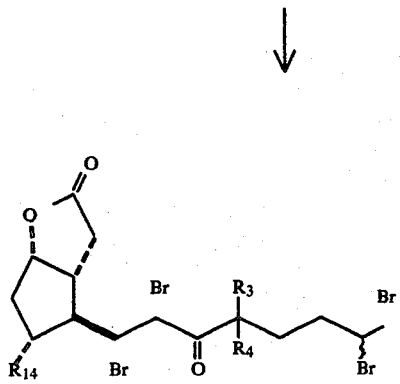
XLVIII
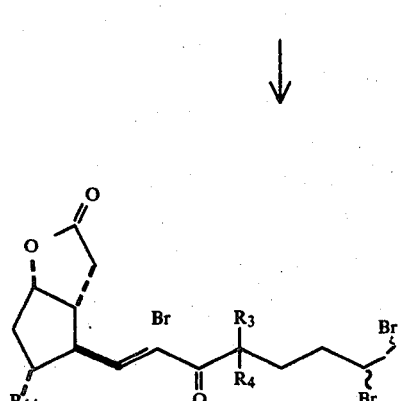
XLIX
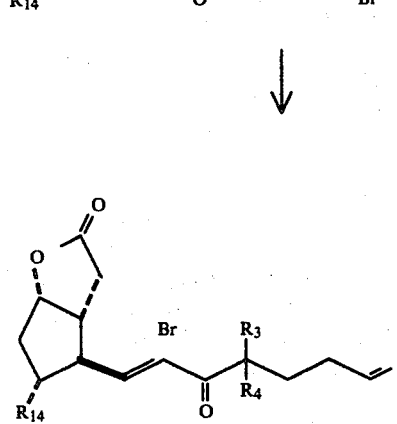
↓ several steps

CHART 5 -continued
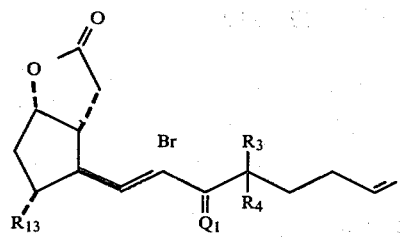
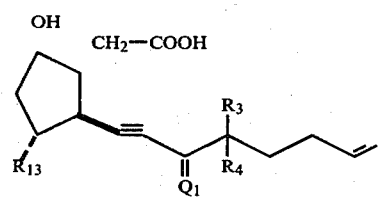
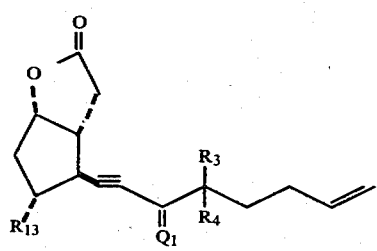
CHART 6
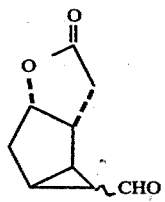
↓ step (a)
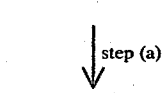
↓ step (b)
CHART 6 -continued
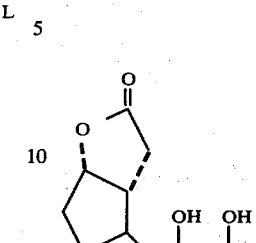 XXXI
↓ step (c)
LI 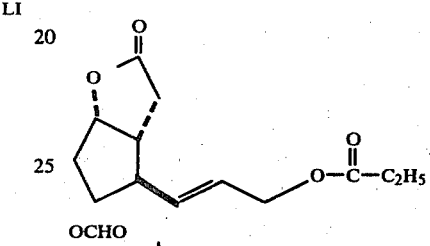 XXXII
↓ step (d)
LII 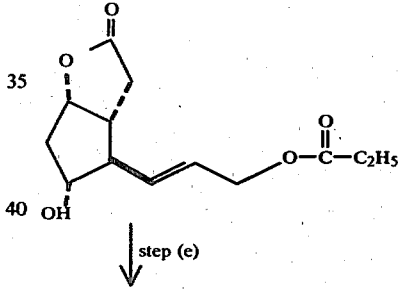 XXXIII
↓ step (e)
XXIX 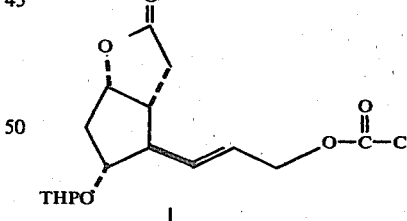 XXXIV
↓ step (f)
XXX 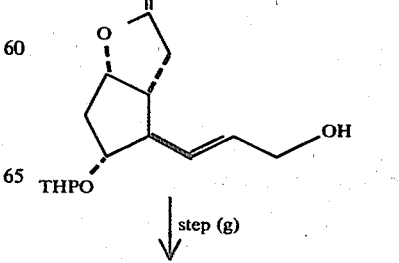 XXXV
↓ step (g)

CHART 6
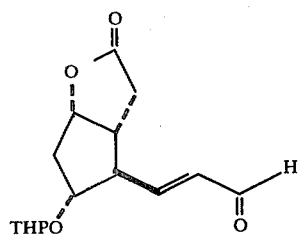
CHART 7
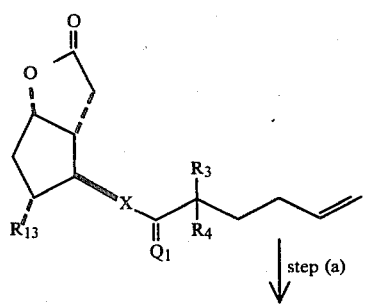
↓ step (a)
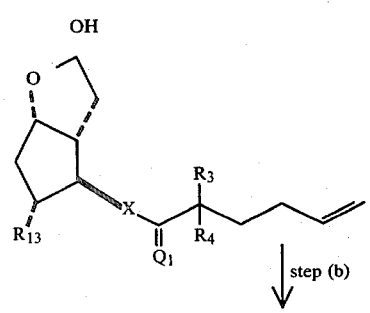
↓ step (b)
LIV
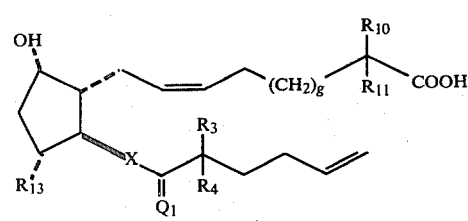
LV
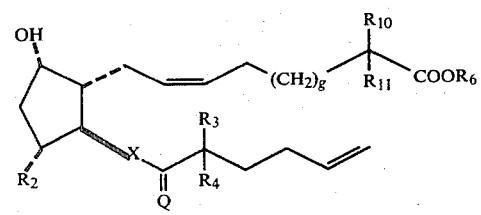
CHART 8
LIII
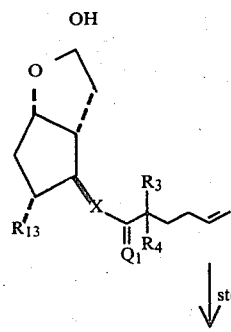
↓ step (a)
LVII
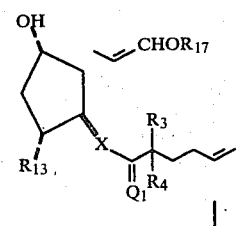
↓ step (b)
LVIII
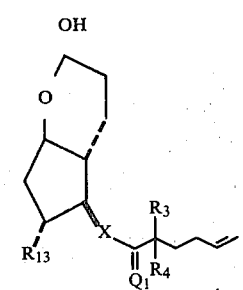
↓ step (c)
LIX
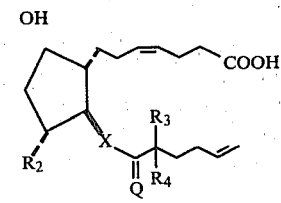
CHART 9
LX
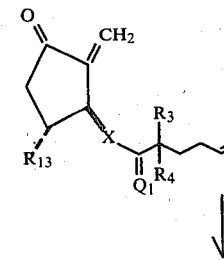
↓ step (a)
XXXVI
VIII
LIII -continued
CHART 9
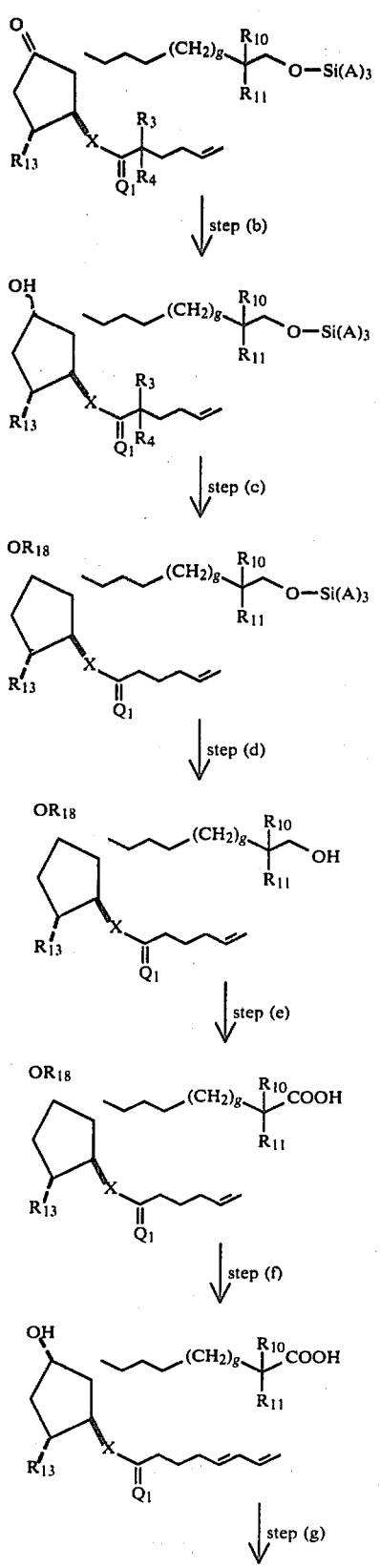
-continued
CHART 9
LXVII
CHART 10
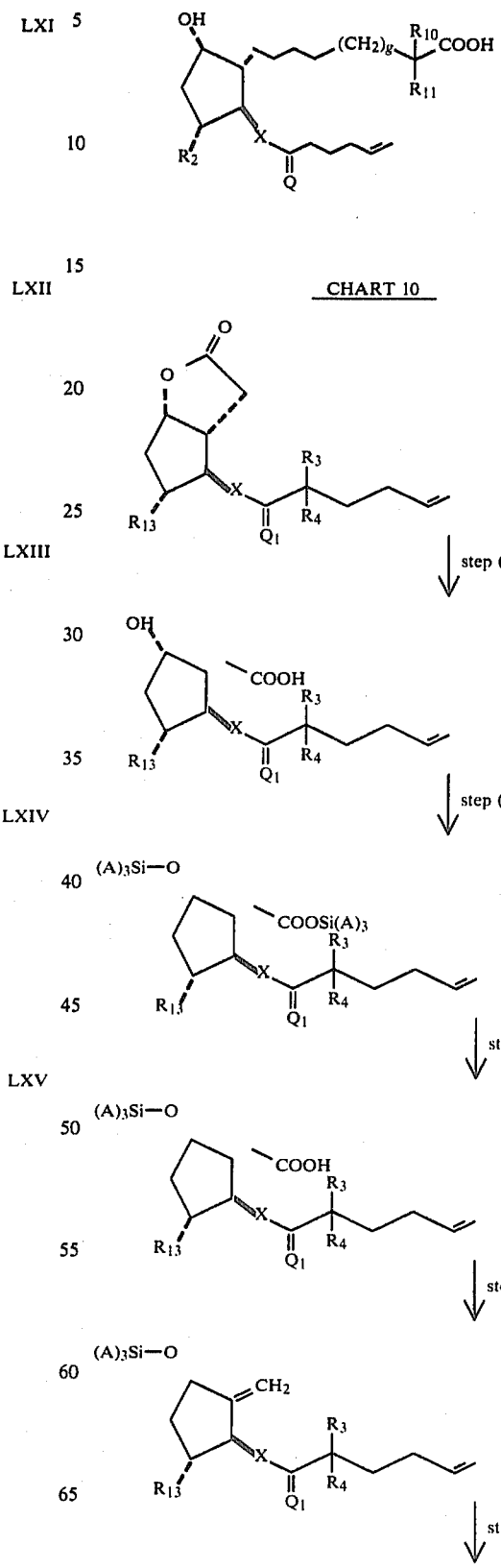

-continued
CHART 10
LXXII
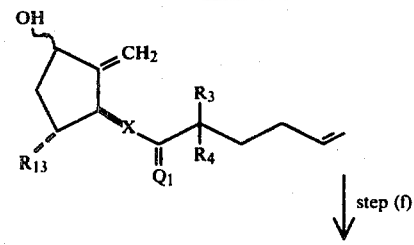
step (f)
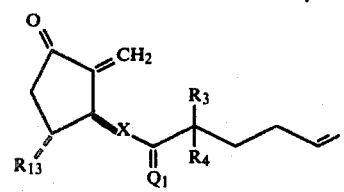
CHART 11
LXXIII
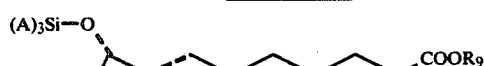
step (a)
LXXIV
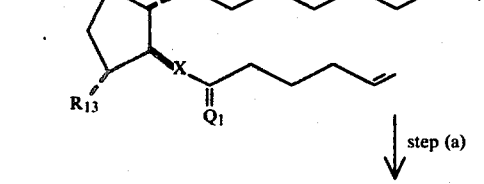
step (b)
LXXV
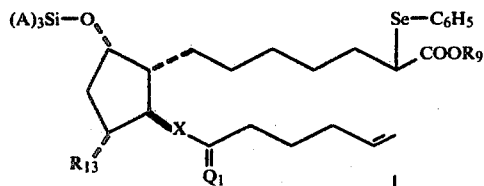
step (c)
LXXVI
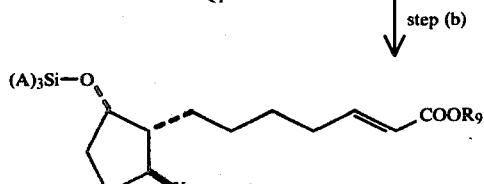
step (d)
LXXVII
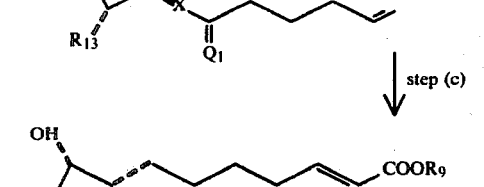
CHART 12
LX
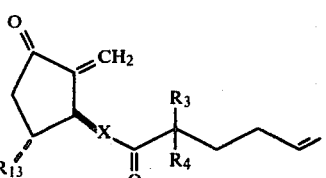
step (a)
LXXVIII
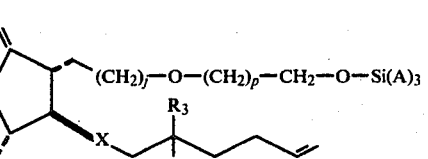
step (b)
LXXIX
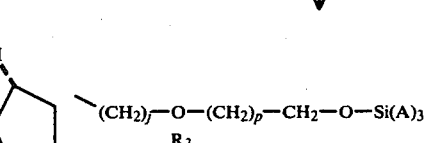
step (c)
LXXX
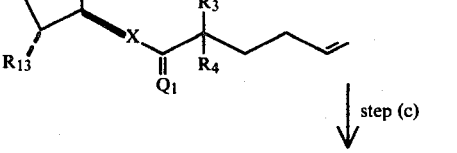
step (d)
LXXXI
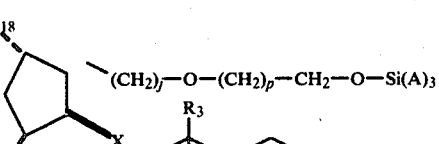
step (e)
LXXXII
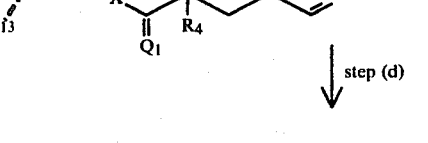
step (f)

-continued
CHART 12
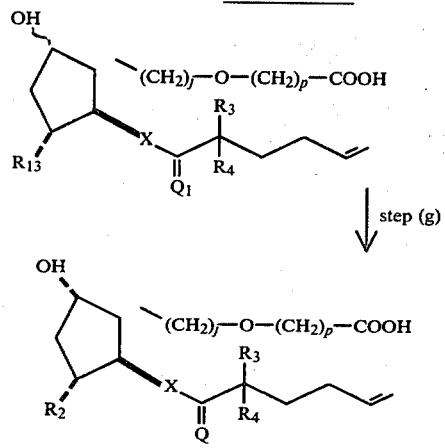
LXXXIII
LXXXIV
CHART 13
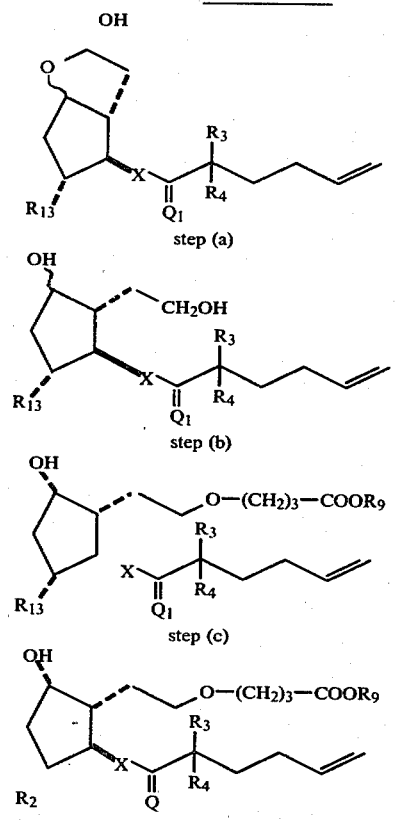
LIII
LXXV
LXXXVI
LXXXVII
CHART 14
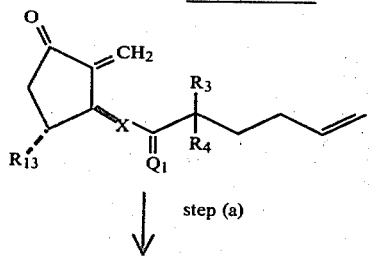
LX
-continued
CHART 14
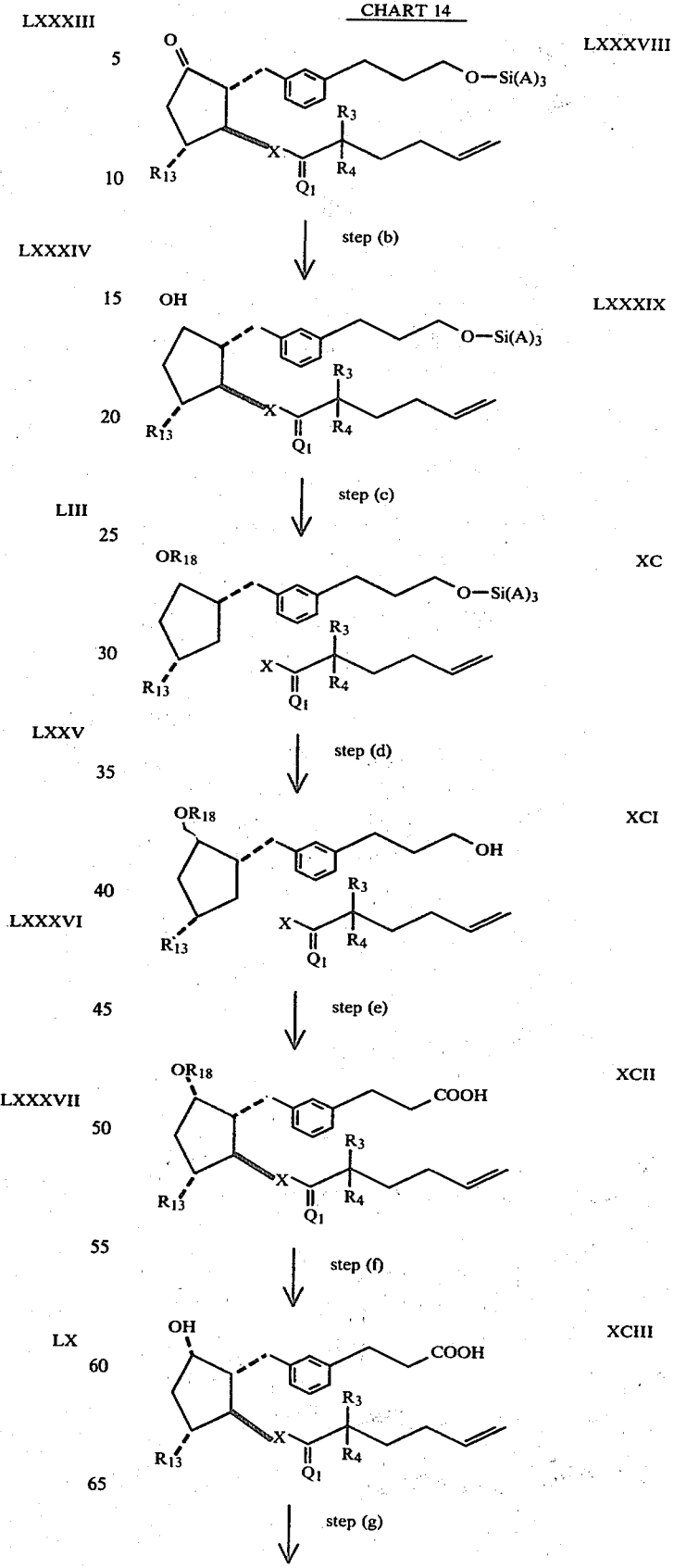
LXXXVIII
LXXXIX
XC
XCI
XCII
XCIII 4,228,104
-continued
CHART 14
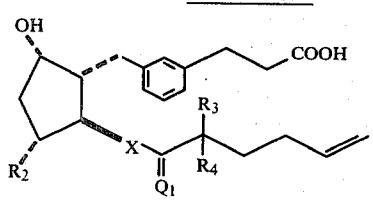
XCIV
CHART 15
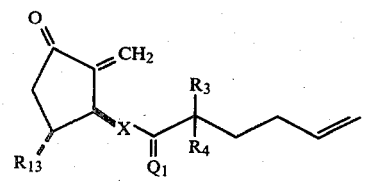
LX
step (a)
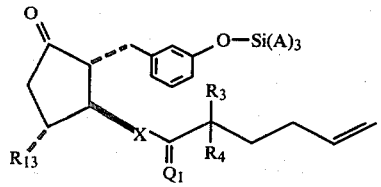
XCV
step (b)
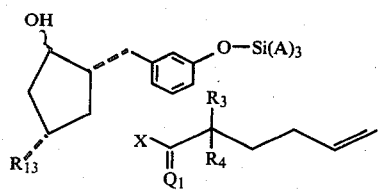
XCVI
step (c)
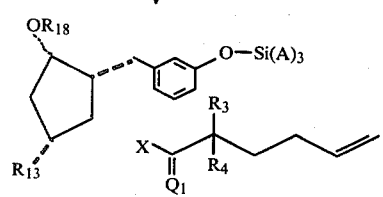
XCVII
step (d)
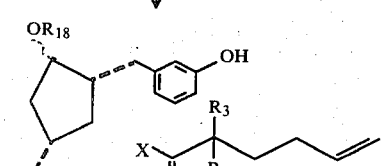
XCVIII
step (e)
-continued
CHART 15
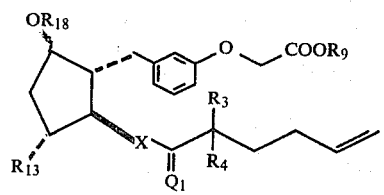
XCIX
step (f)
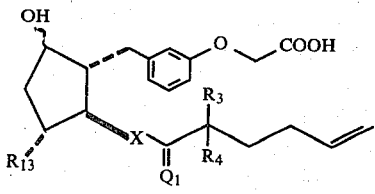
C
step (g)
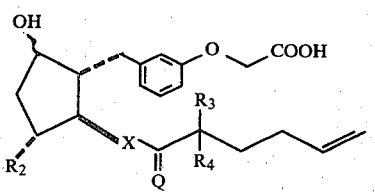
CI
CHART 16
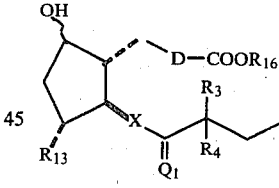
CII
step (a)
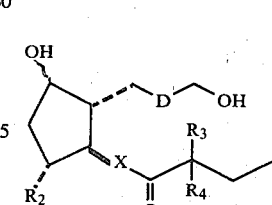
CIII
step (b)
CIV 4,228,104
CHART 16
-continued
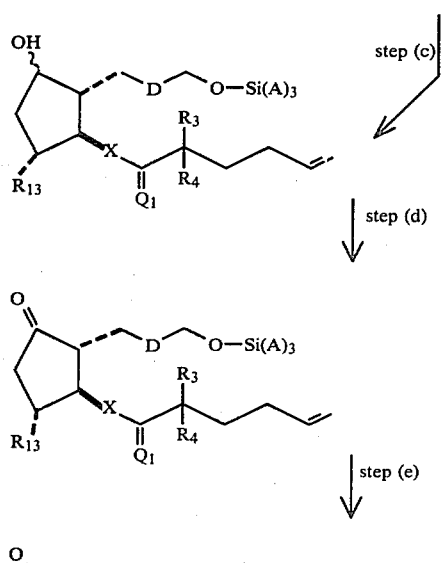
CHART 17
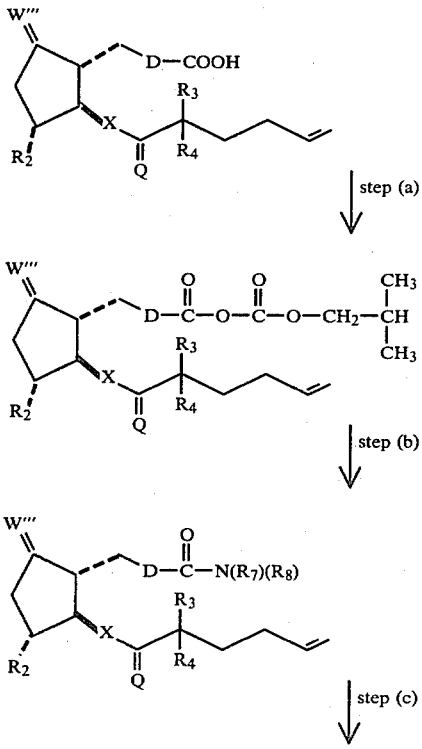
CHART 17
-continued
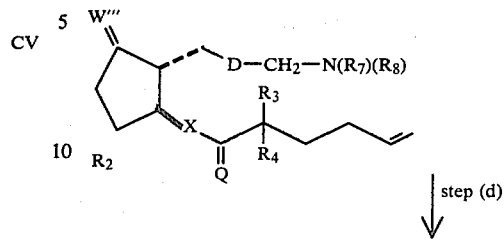
CV
CVI
CHART 18
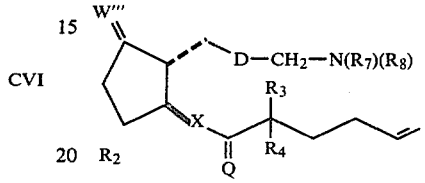
CVII
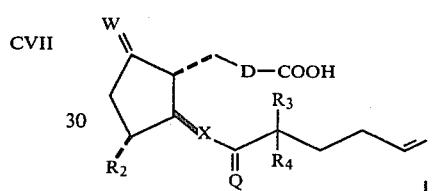
CVIII
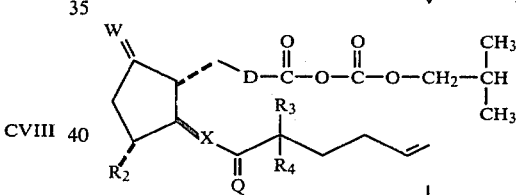
CIX
CHART 19
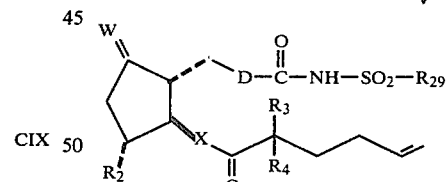
CX
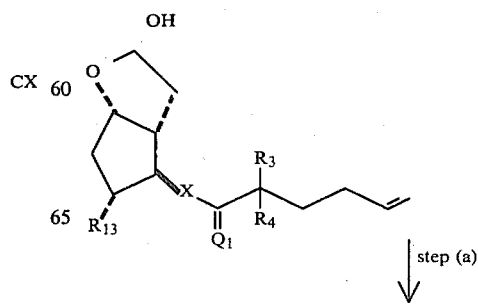
CXI
CXII
CXIII
CXIV
CXV
LIII

CHART 19
-continued
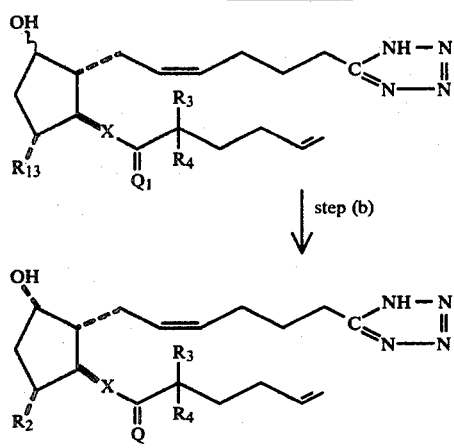
CHART 20
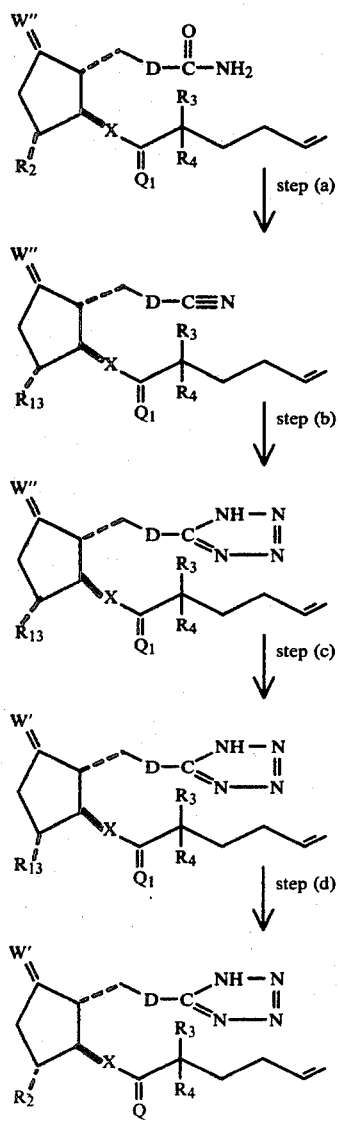
CHART 21
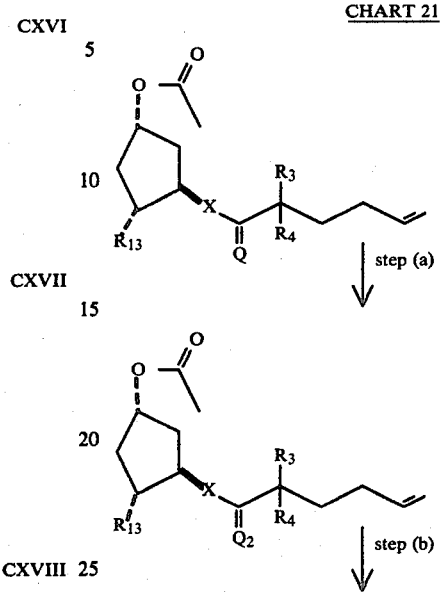
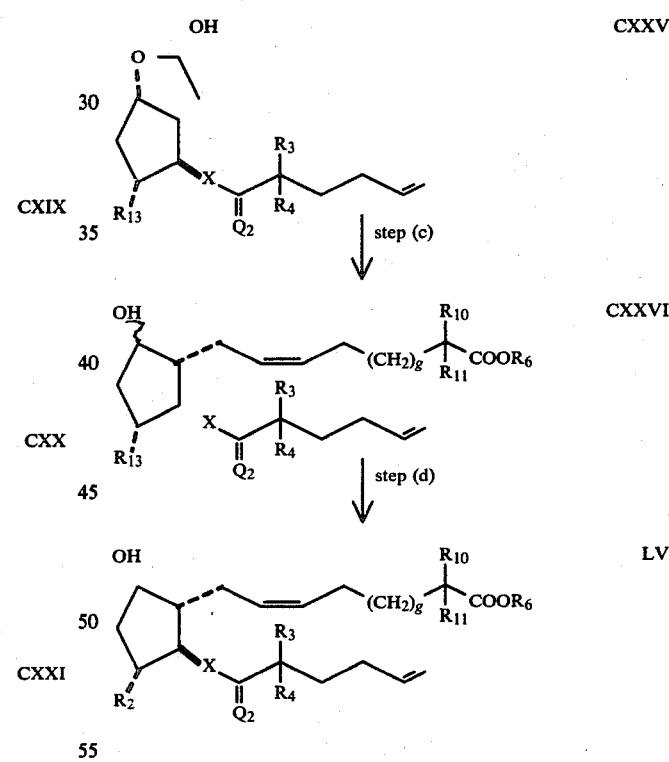
CHART 22
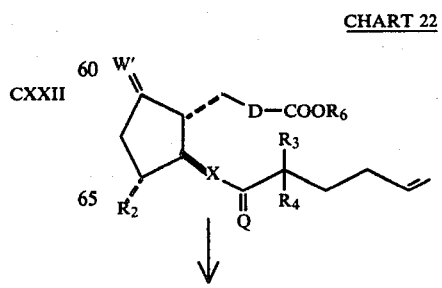

91
-continued
CHART 22
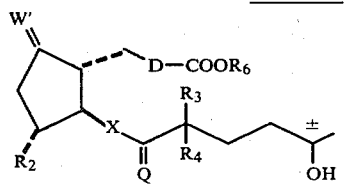
CHART 23
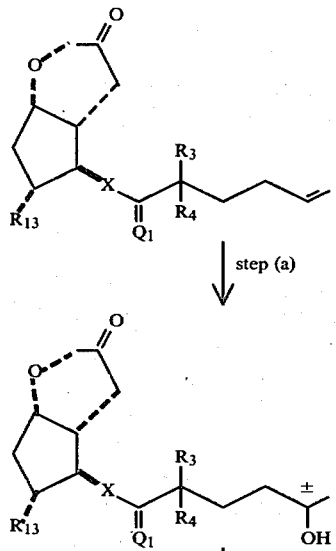
↓ step (a)
↓ several steps
92
-continued
CHART 23
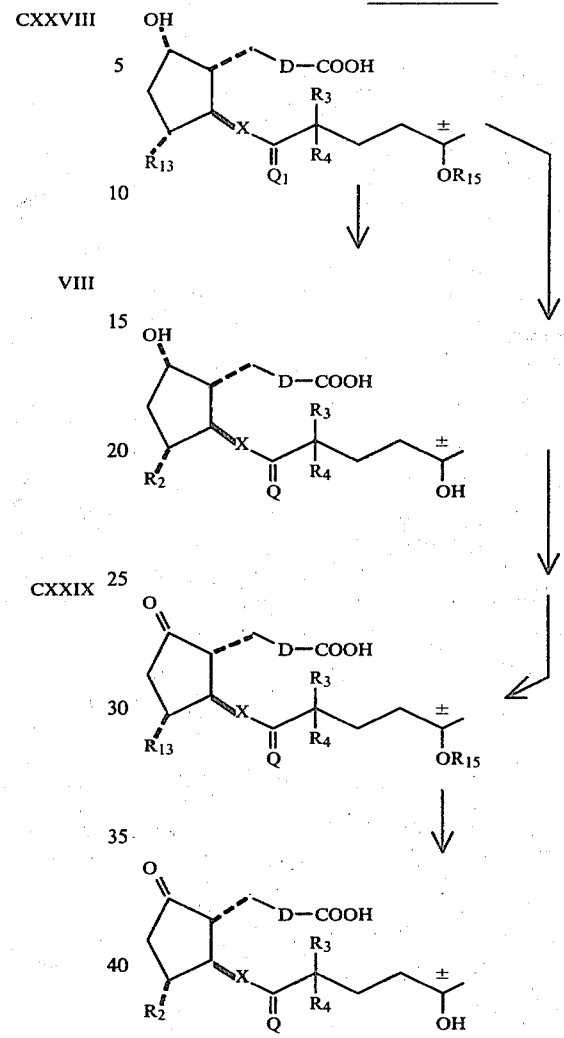
CXXVIII
↓
VIII
↓
CXXIX
↓
CHART 24
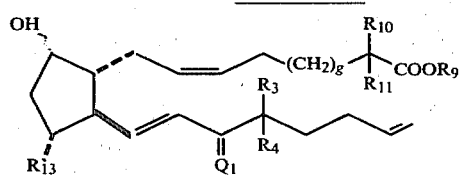 CXXXIV
↓ step (a)
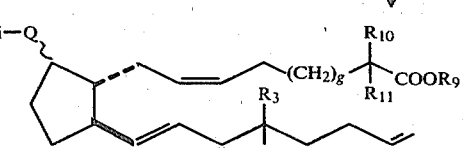 CXXXV
↓ step (b)

CHART 24
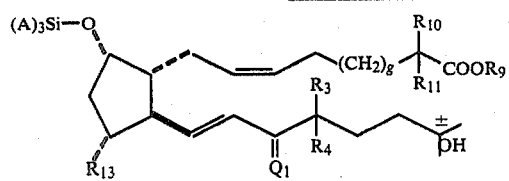
CXXXVI
↓ step (c)
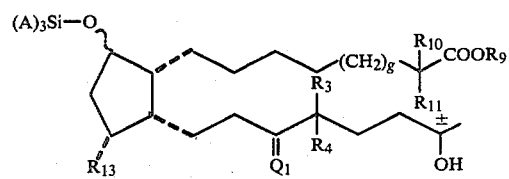
CXXXVII
↓ step (d)
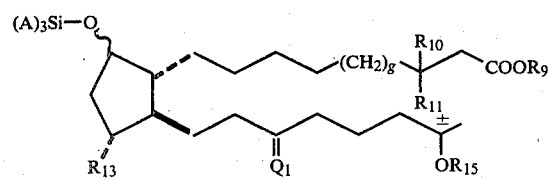
CXXXVIII
↓ step (e)
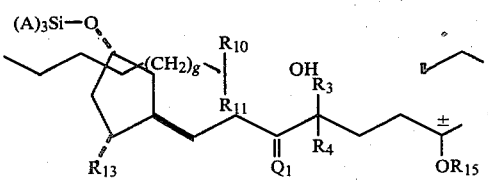
CXXXIX
↓ step (f)
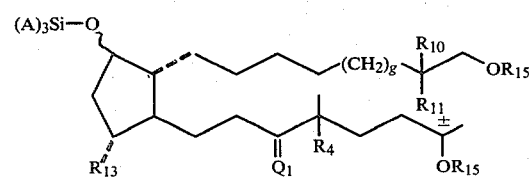
CXL
↓ step (g)
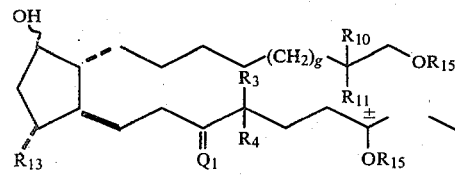
CXLI
↓ step (h)

CHART 24
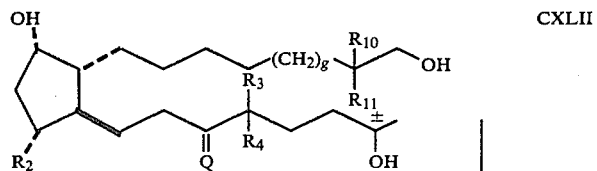 CXLII
step (i)
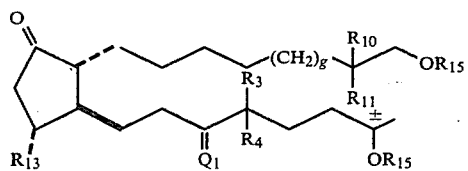 CXLIII
step (j)
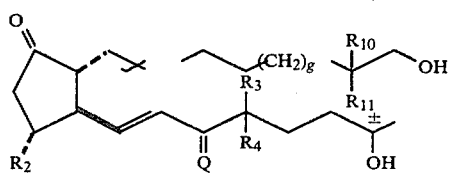 CXLIV
+
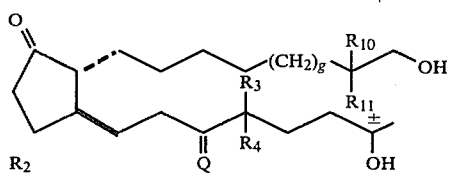 CXLV
CHART 25
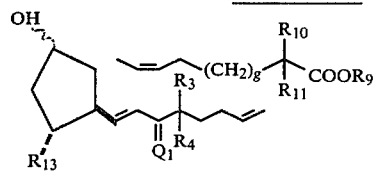 CXLVI
step (a)
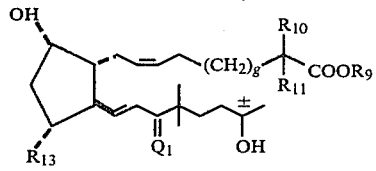 CXLVII
step (b)
-continued
CHART 25
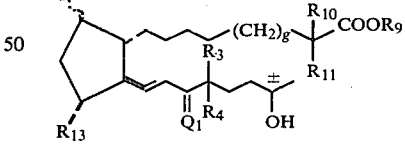 CXLVIII
step (c)
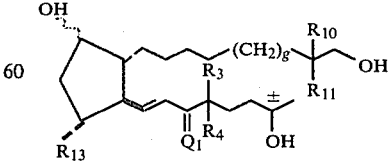 CXLIX
step (d)

CHART 25
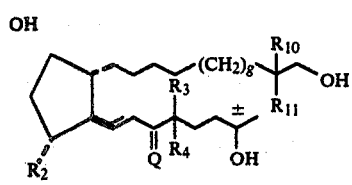
CHART 26
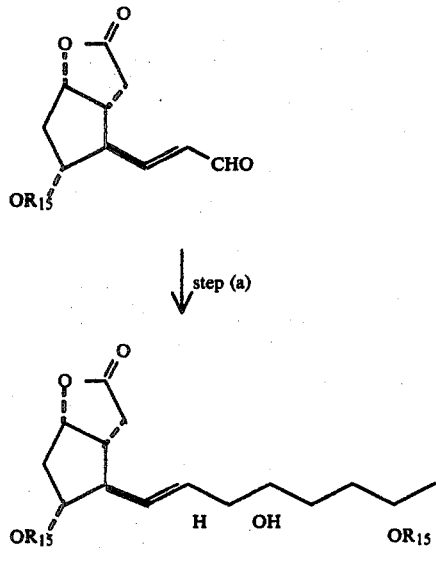
↓ step (a)
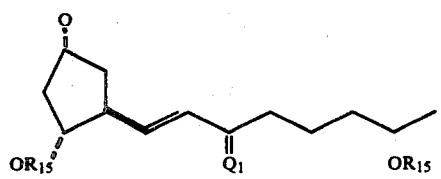
↓ several steps
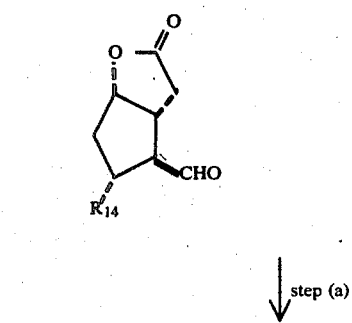
CHART 27
CHART 27 -continued
CL 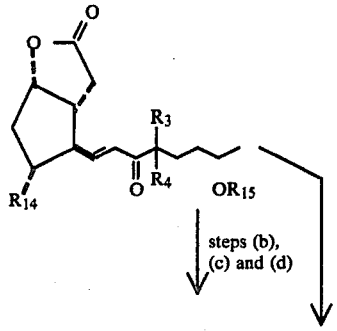 CLIV
↓ steps (b), (c) and (d)
XXVI 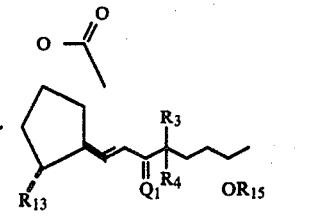 CLVI
↓ step (e)
CLII 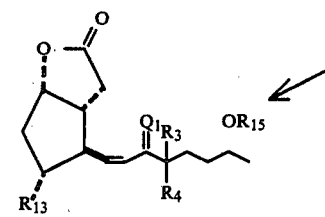 CLVII
↓ step (f)
CLIII 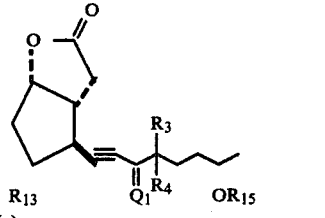 CLVIII
↓ step (g)
XXXVII 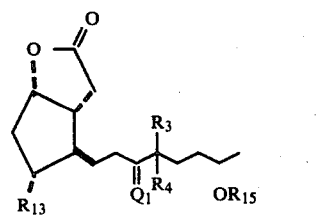 CLIX

CHART 28
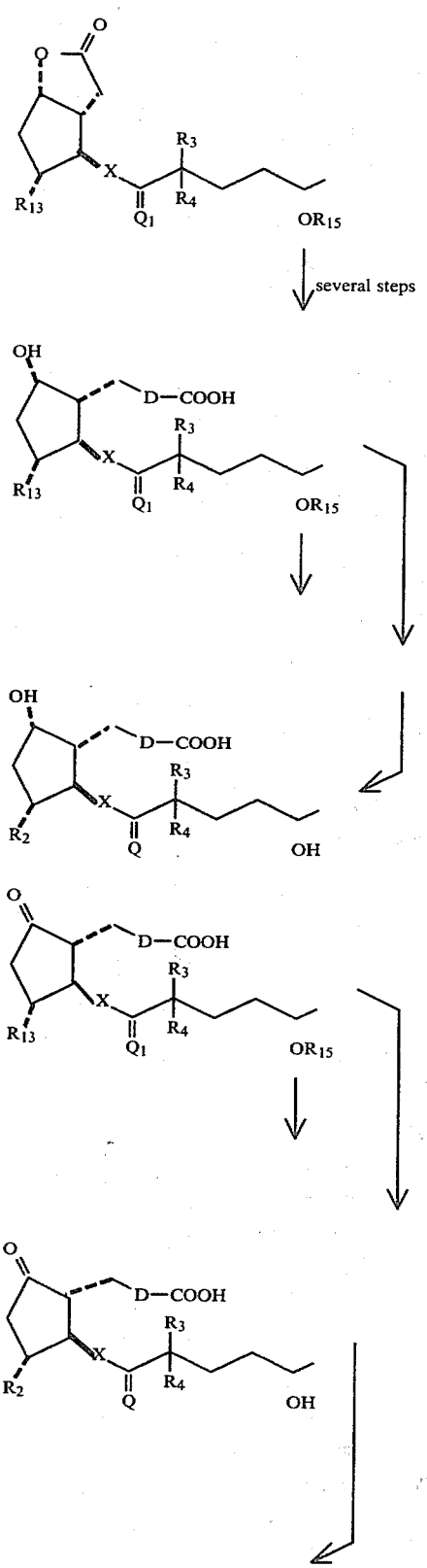
CHART 28 -continued
CHART 29
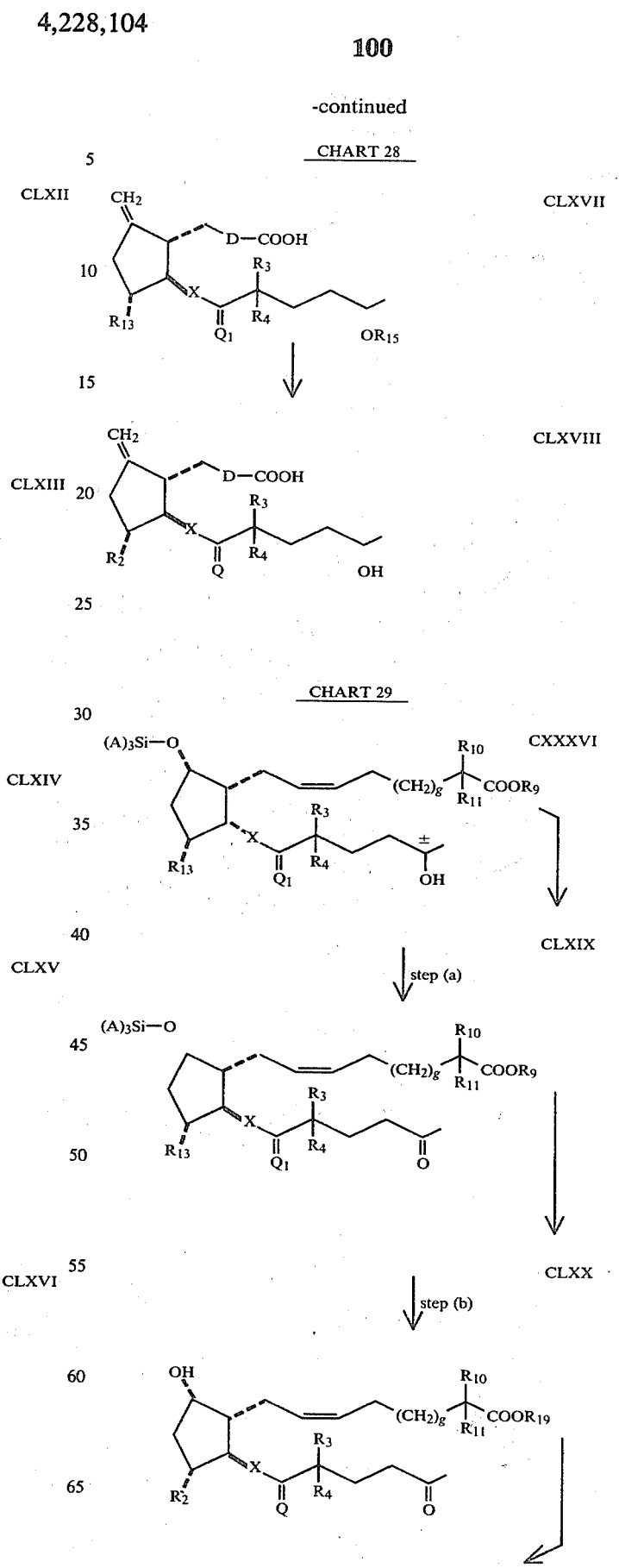

4,228,104
101
-continued
CHART 29
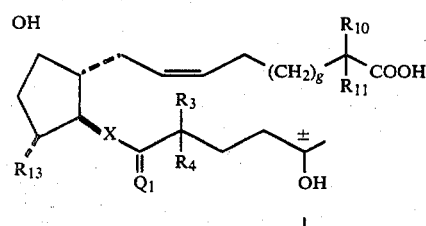
CLXXI
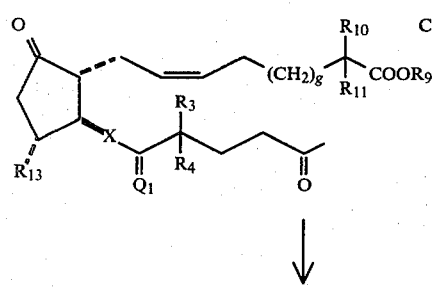
CLXXII
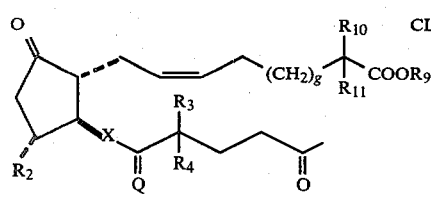
CLXXIII
CHART 30
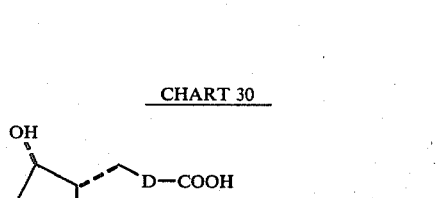
IX
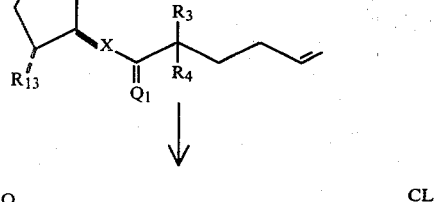
CLXXIV
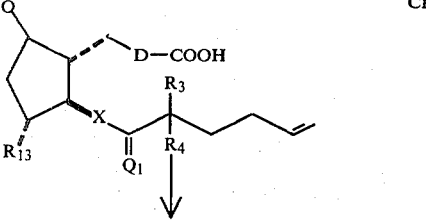
CLXXV
102
-continued
CHART 30
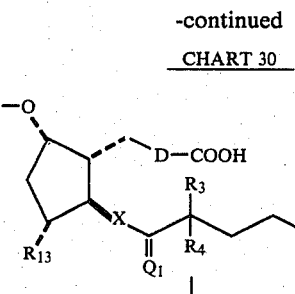
CLXXVI
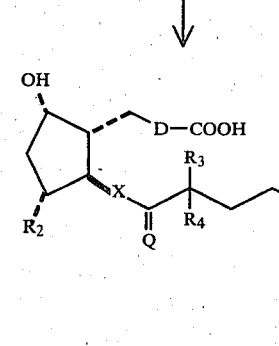
CLXXVII
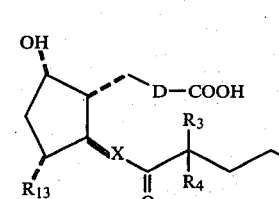
CLXXVIII
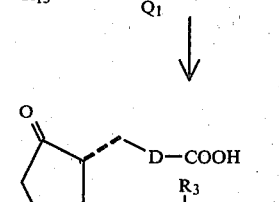
CLXXIX
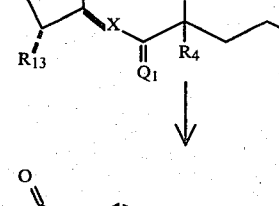
CLXXX
CHART 31
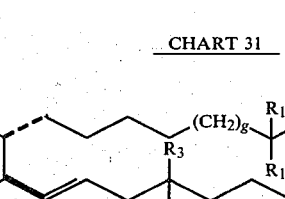
CXLIX
↓ step (a)

CHART 31
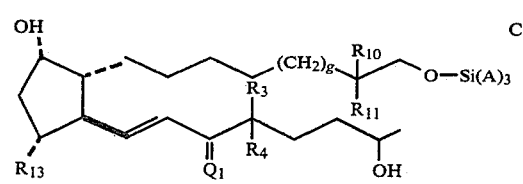
CLXXXI
↓ step (b)
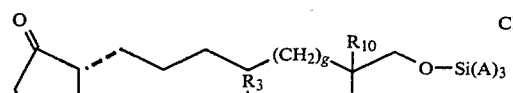
CLXXXII
↓ step (c)
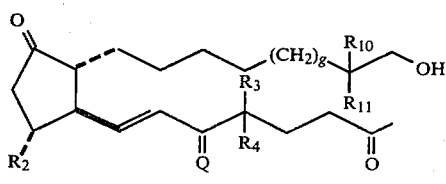
CLXXXIII
+
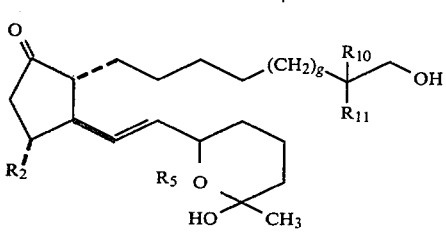
CLXXXIV
CHART 32
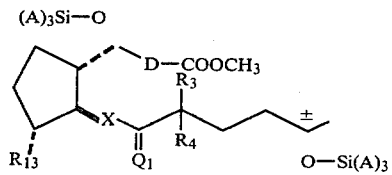
↓ step (a)
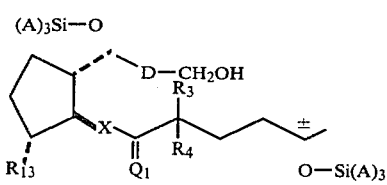
CLXXXVI
↓ step (b)
CHART 32 (continued)
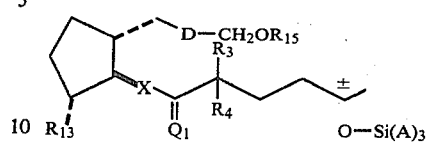
CLXXXVII
↓ step (c)
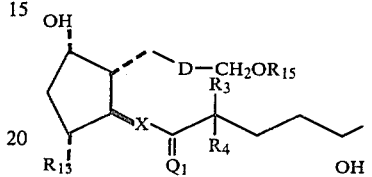
CLXXXVIII
↓ step (d)
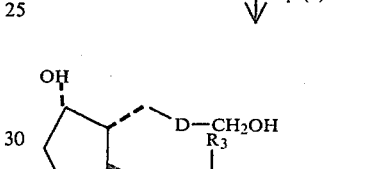
CLXXXIX
↓ step (e)
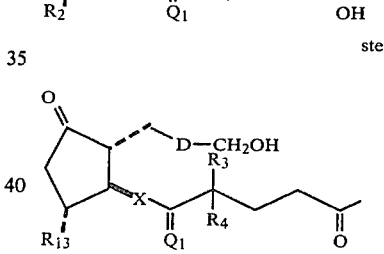
CXC
↓ step (f)
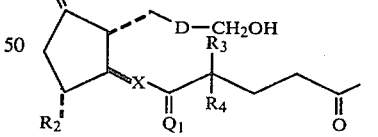
CXCI
CHART 33
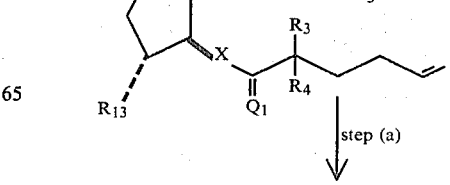
CXCII
↓ step (a)

-continued
CHART 33
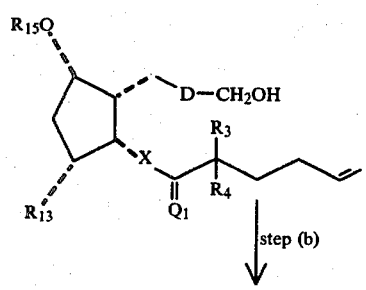
↓ step (b)
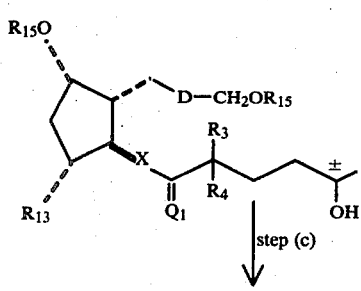
↓ step (c)
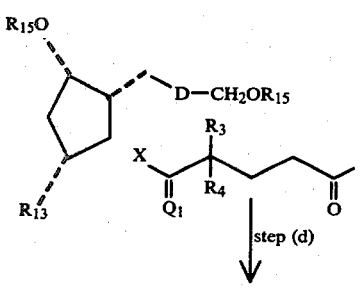
↓ step (d)
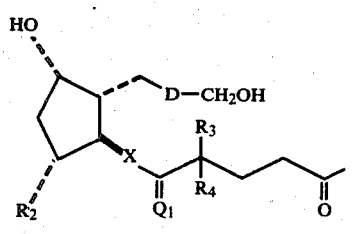
CHART 34
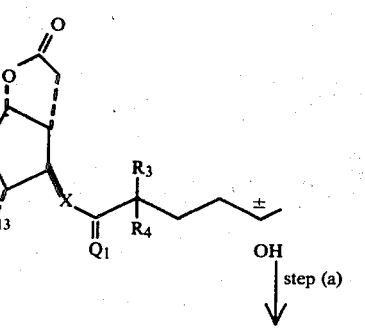
↓ step (a)
-continued
CHART 34
CXCIII
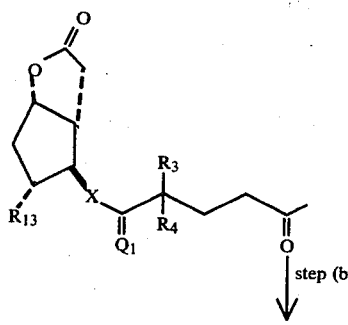
↓ step (b)
CXCIV
CXCVIII
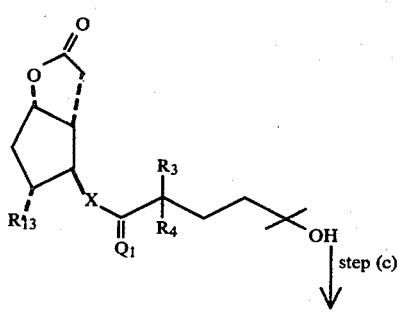
↓ step (c)
CXCV
CXCIX
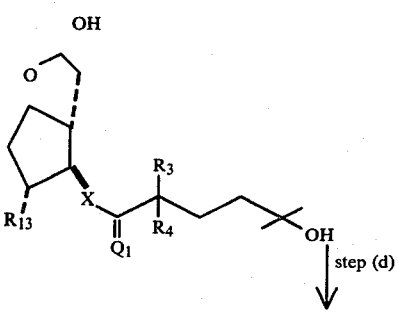
↓ step (d)
CXCVI
CC
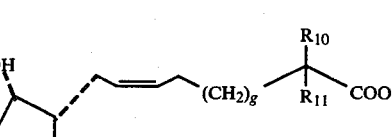
↓ step (e)
CXXIX
CCI
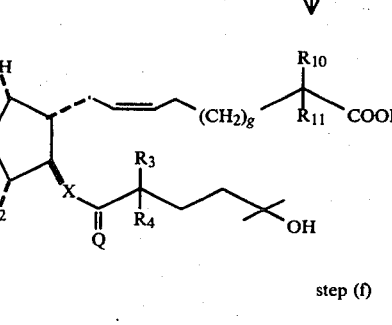
↓ step (f)

CHART 34 -continued
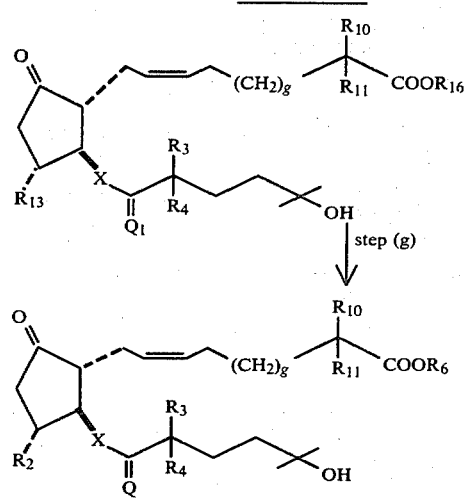
CHART 35
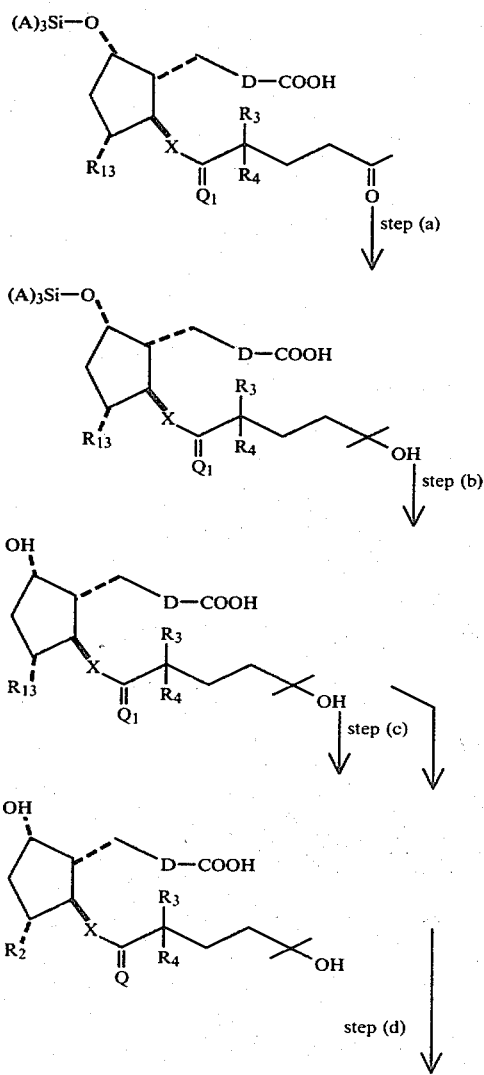
CHART 35 -continued
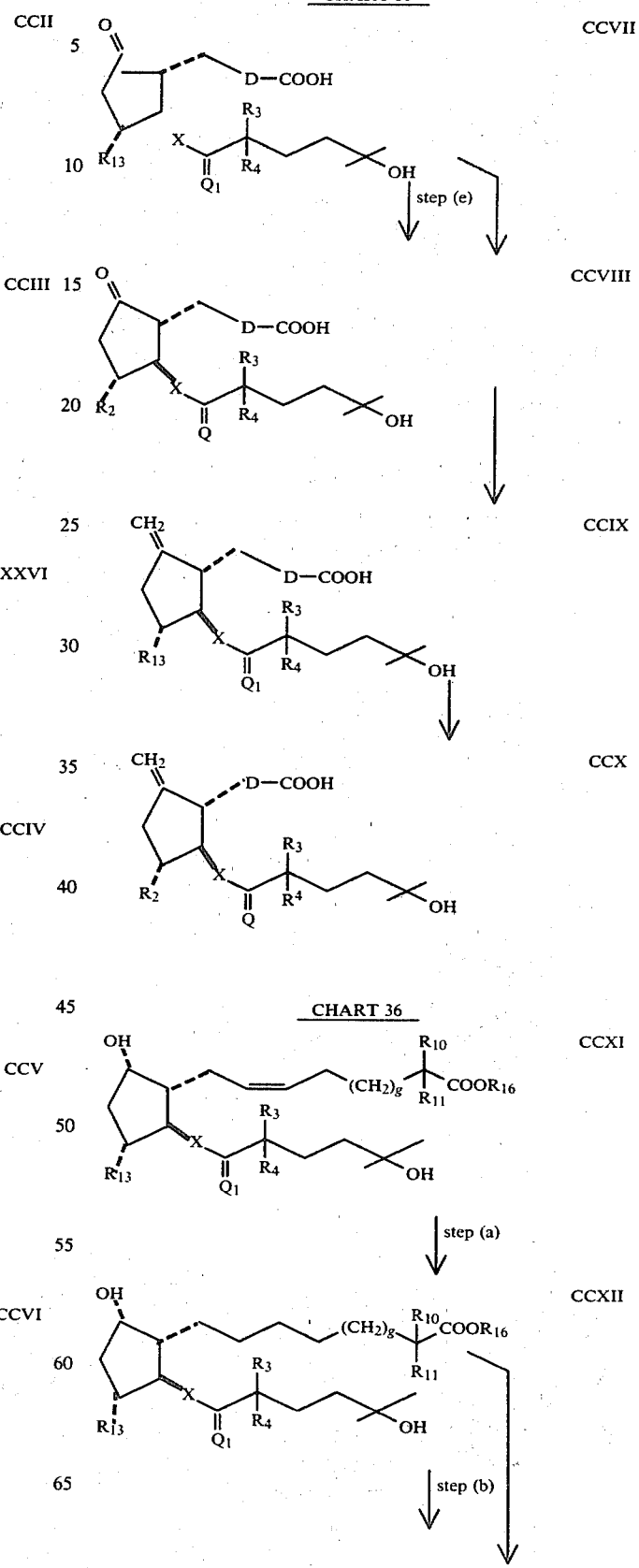
CHART 36
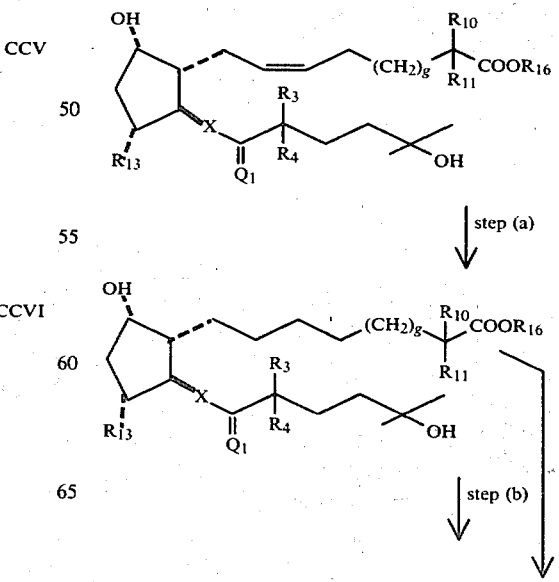

-continued
CHART 36
CCXIII
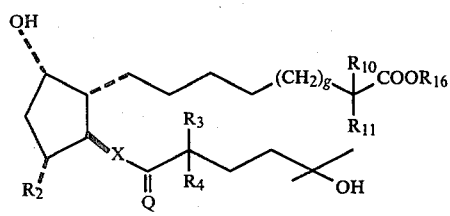
↓ step (c)
CCXIV
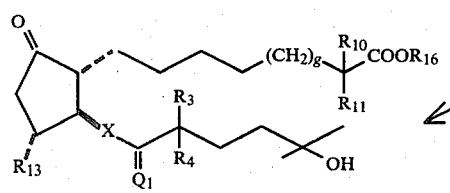
↓ step (d)
CCXV
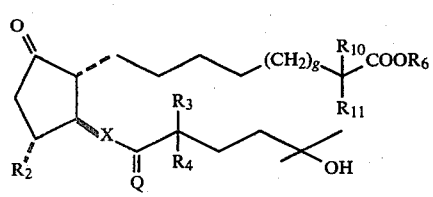
CHART 37
CXCIX
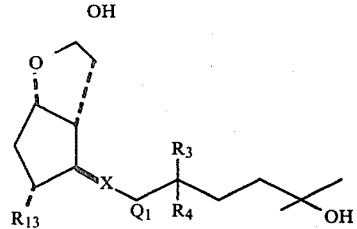
↓ step (a)
CCXVI
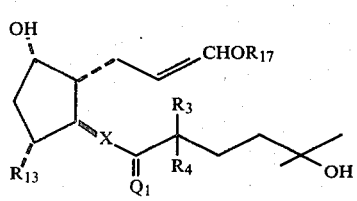
↓ step (b)
-continued
CHART 37
CCXVII
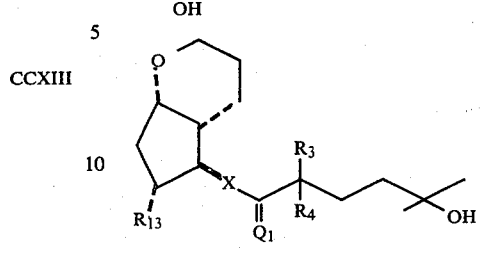
↓ step (c)
CCXVIII
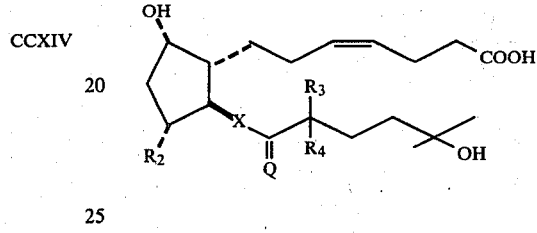
CHART 38
CCXIX
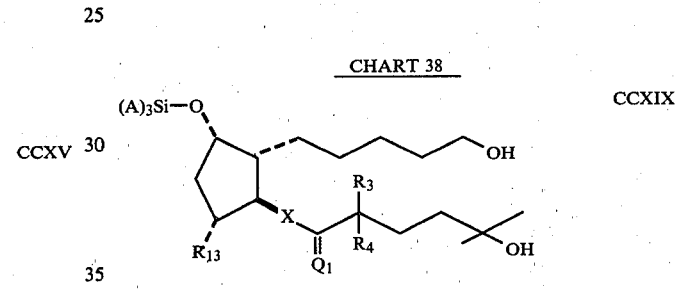
↓ step (a)
CCXX
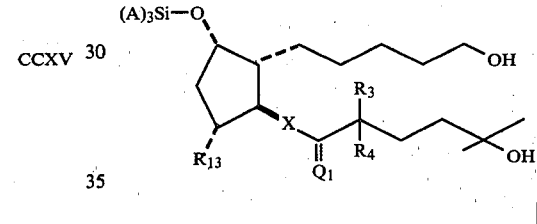
↓ step (b)
CCXXI
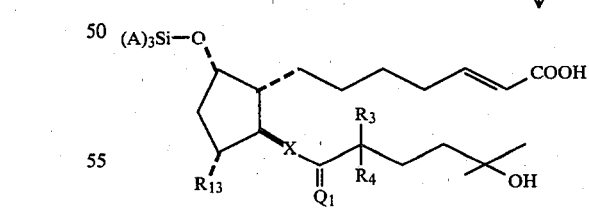
↓ step (c)
CCXXII
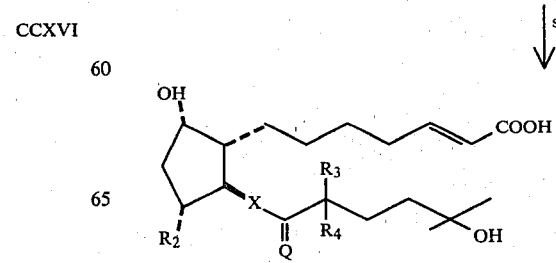

CHART 39
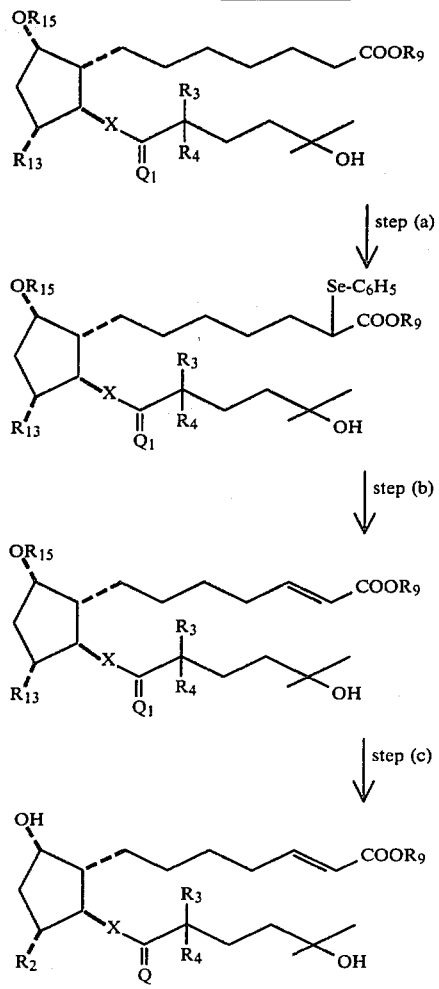
CCXXIII
CCXXIV
CCXXV
CCXXVI
CHART 40
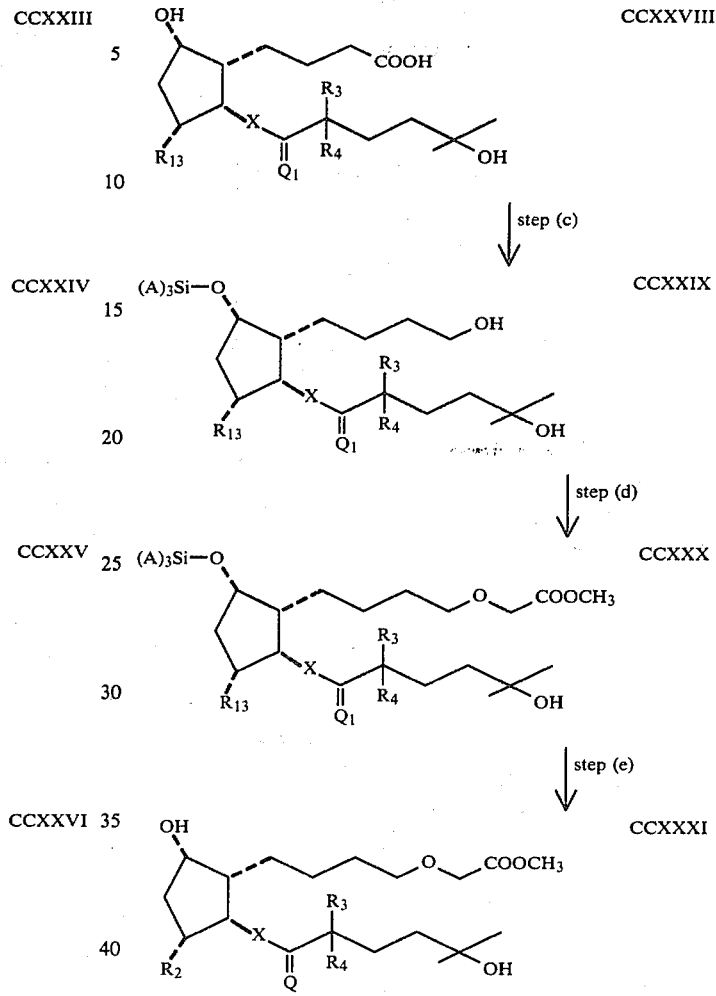
CCXXVIII
CCXXIX
CCXXX
CCXXXI
CHART 40
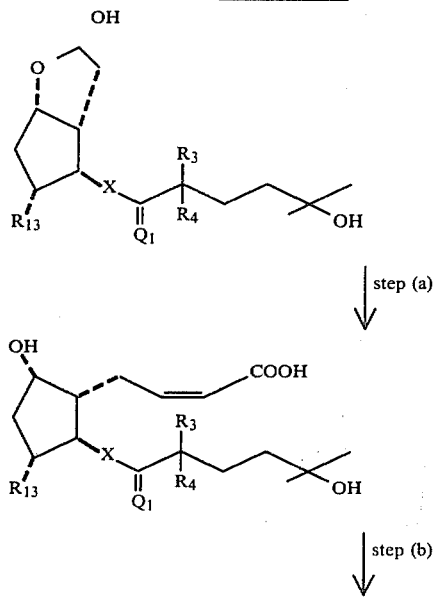
CXCIX
CCXXVII
CHART 41
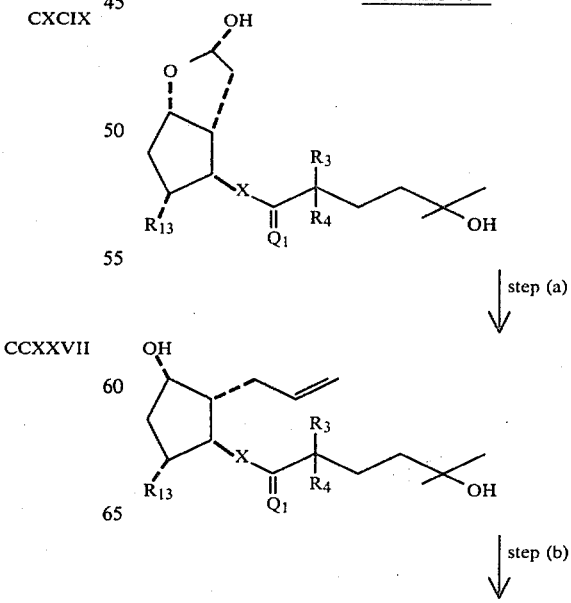
CXCIX
CCXXXII -continued
CHART 41
CHART 42
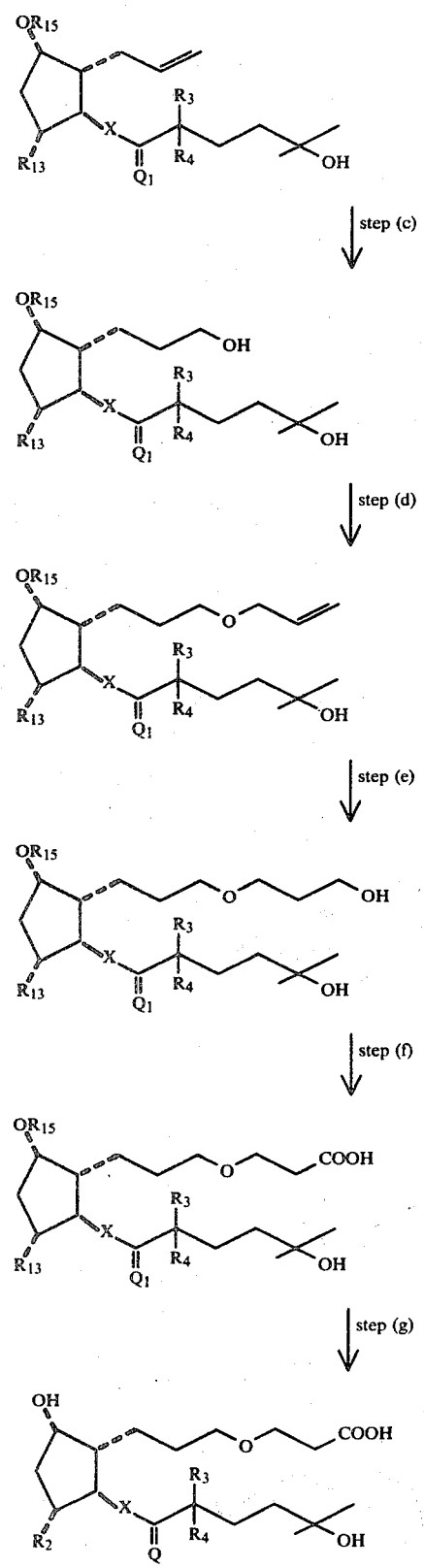
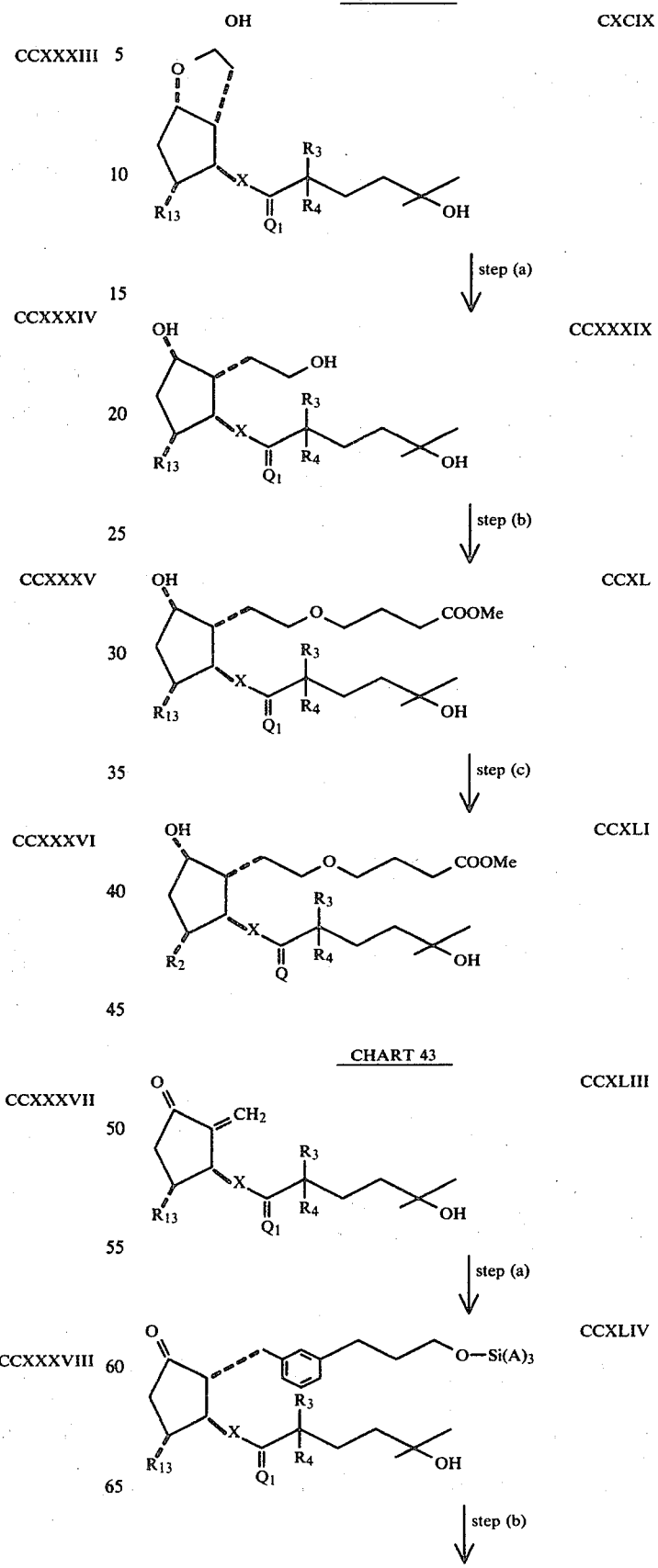
CHART 43
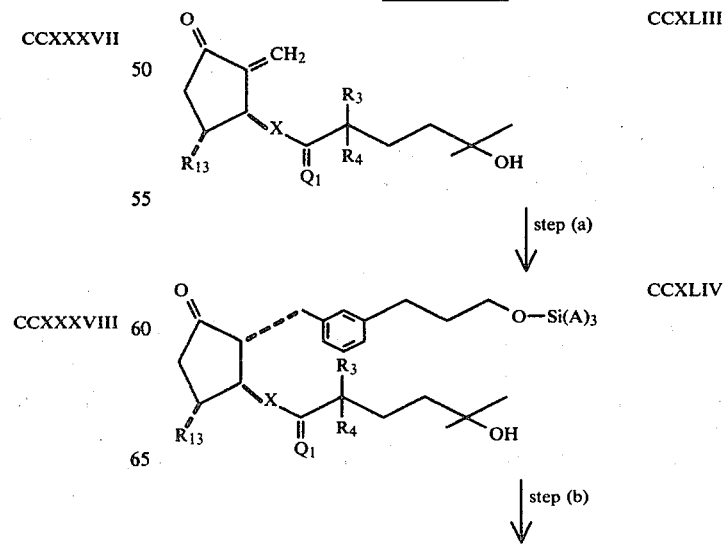

4,228,104
CHART 43 -continued
CCXLV 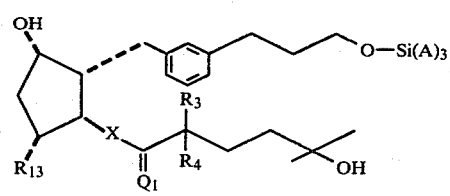
↓ step (c)
CCXLVI 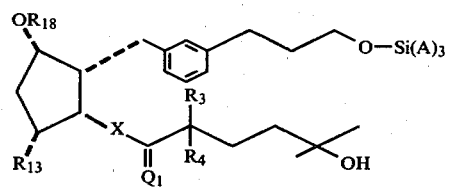
↓ step (d)
CCXLVII 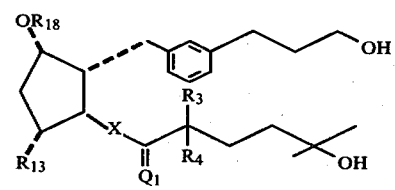
↓ step (e)
CCXLVIII 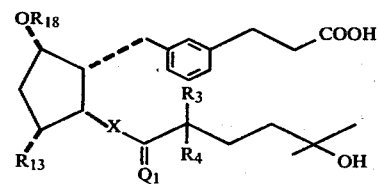
↓ step (f)
CCXLIX 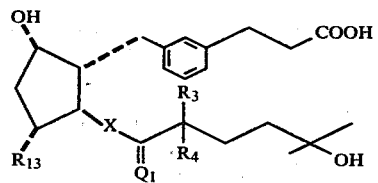
↓ step (g)
CCL 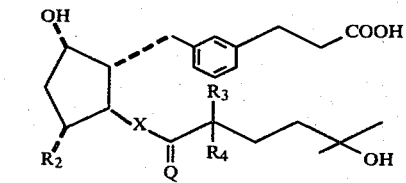
CHART 44
CXCVIII 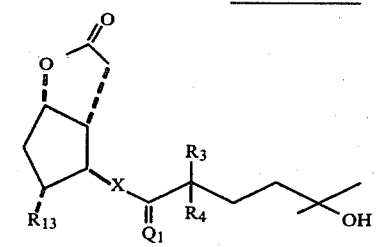
↓ step (a)
CCLI 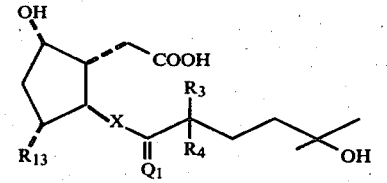
↓ step (b)
CCLII 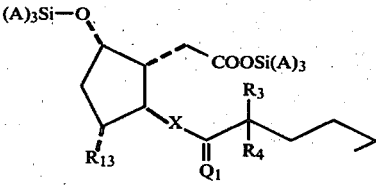
↓ step (c)
CCLIII 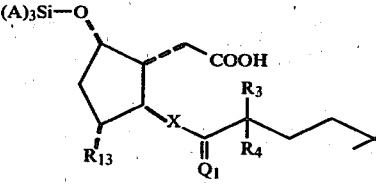
↓ step (d)
CCLIV 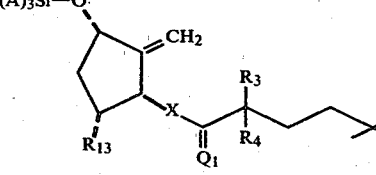
↓ step (e)
CCLV 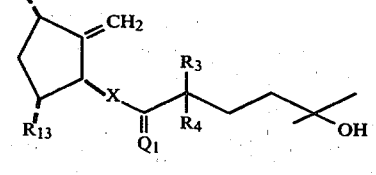
↓ step (f)

117
-continued
CHART 44
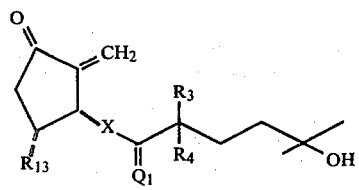
CHART 45
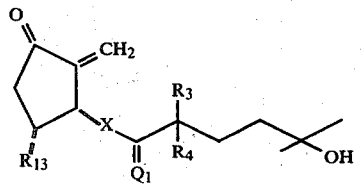
↓ step (a)
CCLVI
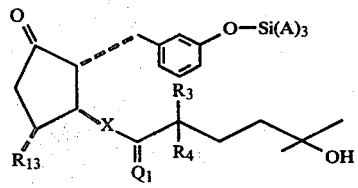
↓ step (b)
CCLVII
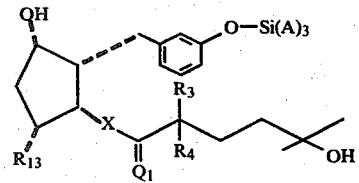
↓ step (c)
CCLVIII
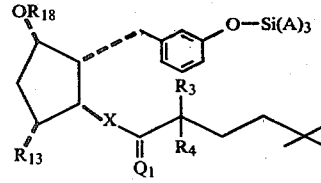
↓ step (d)
CCLIX
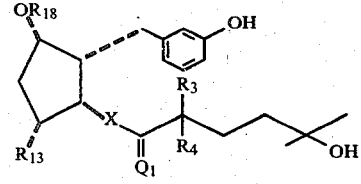
↓ step (e)
118
-continued
CHART 45
CCXLIII
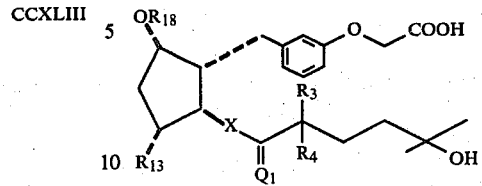
↓ step (f)
CCLXI
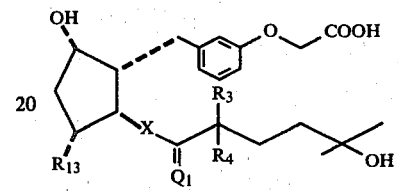
↓ step (g)
CCLXII
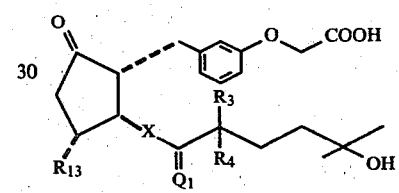
↓ step (h)
CCLXIII
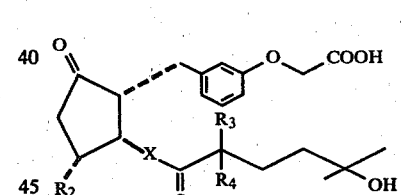
↓ step (i)
CCLXIV
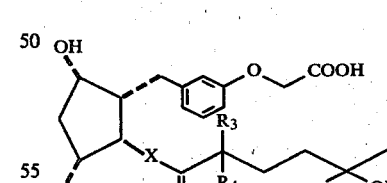
↓ step (j)
CCLXV
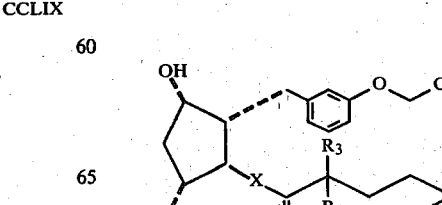
CCLX CHART 46
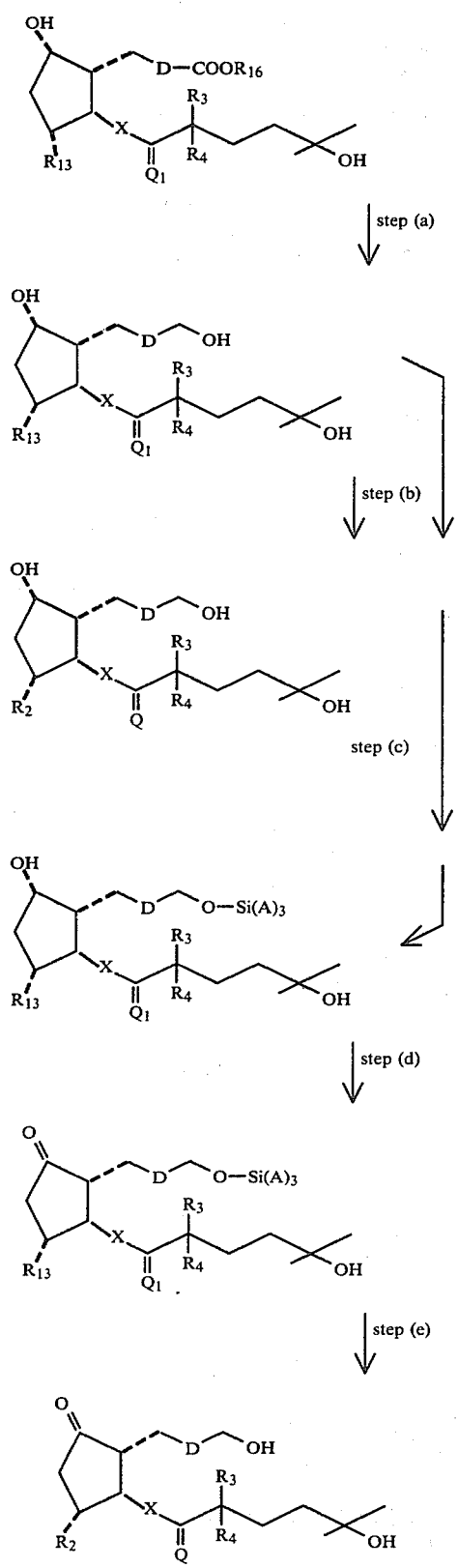
CHART 47
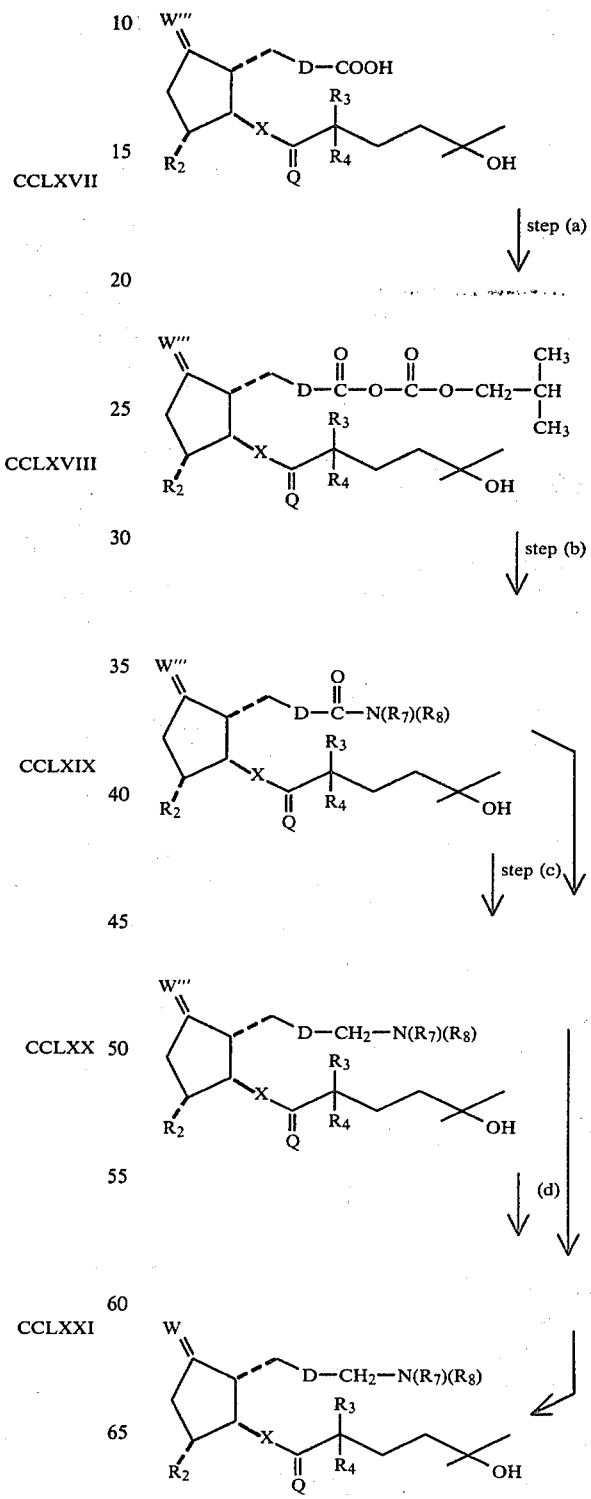

CHART 48

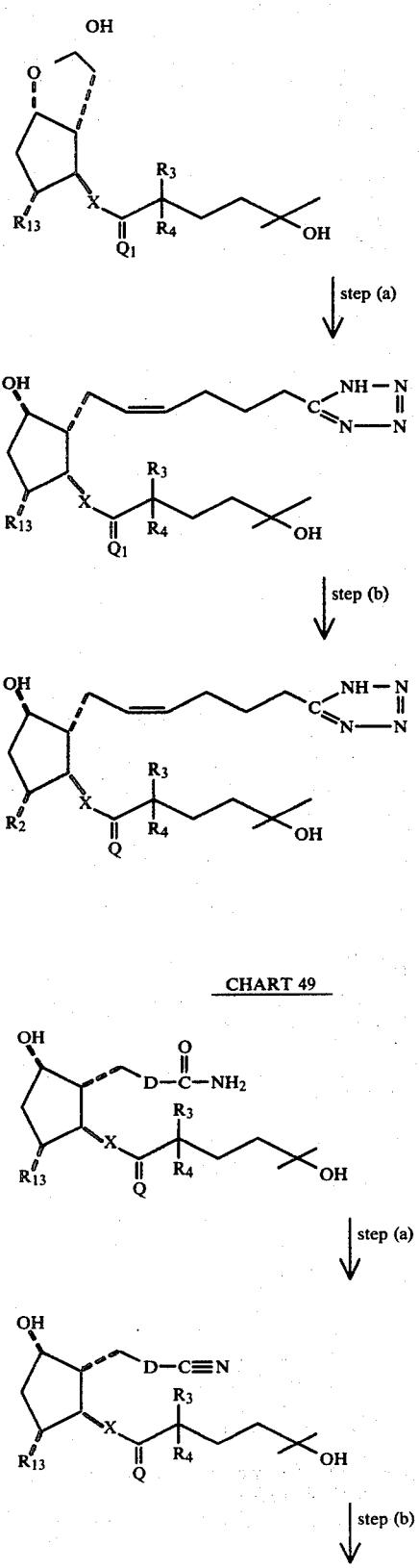

CHART 49

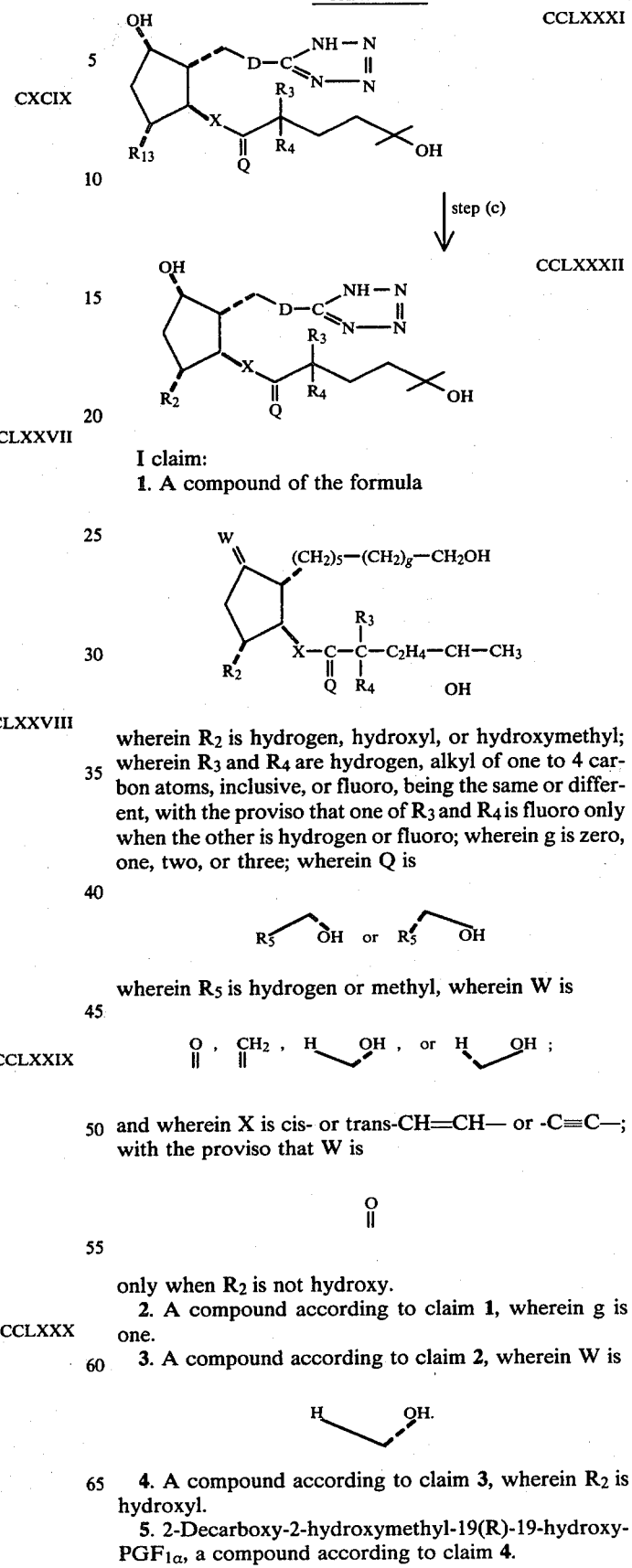

I claim:
1. A compound of the formula

$$\underset{R_2}{\overset{W}{\diagdown}}\!\!\!\!\underset{\phantom{x}}{\diagup}\!\!\!\!\underset{\phantom{x}}{\overset{(CH_2)_5-(CH_2)_g-CH_2OH}{\diagdown}}$$
$$X-\underset{\underset{Q}{\parallel}}{C}-\underset{\underset{R_4}{|}}{\overset{\overset{R_3}{|}}{C}}-C_2H_4-\underset{\underset{OH}{|}}{CH}-CH_3$$

wherein $R_2$ is hydrogen, hydroxyl, or hydroxymethyl; wherein $R_3$ and $R_4$ are hydrogen, alkyl of one to 4 carbon atoms, inclusive, or fluoro, being the same or different, with the proviso that one of $R_3$ and $R_4$ is fluoro only when the other is hydrogen or fluoro; wherein g is zero, one, two, or three; wherein Q is $$\underset{R_5}{\diagdown}\!\!\!\!\underset{\phantom{x}}{\overset{OH}{\diagup}} \text{ or } \underset{R_5}{\diagdown}\!\!\!\!\underset{\phantom{x}}{\overset{OH}{\diagup}}$$

wherein $R_5$ is hydrogen or methyl, wherein W is $$\overset{O}{\underset{\parallel}{\phantom{x}}}, \overset{CH_2}{\underset{\parallel}{\phantom{x}}}, \underset{H}{\diagdown}\!\!\!\!\underset{\phantom{x}}{\overset{OH}{\diagup}}, \text{ or } \underset{H}{\diagdown}\!\!\!\!\underset{\phantom{x}}{\overset{OH}{\diagup}};$$

and wherein X is cis- or trans-$CH=CH-$ or $-C\equiv C-$; with the proviso that W is $$\overset{O}{\underset{\parallel}{\phantom{x}}}$$

only when $R_2$ is not hydroxy.
2. A compound according to claim 1, wherein g is one.
3. A compound according to claim 2, wherein W is $$\underset{H}{\diagdown}\!\!\!\!\underset{\phantom{x}}{\overset{OH}{\diagup}}.$$

4. A compound according to claim 3, wherein $R_2$ is hydroxyl.
5. 2-Decarboxy-2-hydroxymethyl-19(R)-19-hydroxy-$PGF_{1\alpha}$, a compound according to claim 4.

6. 2-Decarboxy-2-hydroxymethyl-16,16-dimethyl-19(R)-19-hydroxy-PGF₁, a compound according to claim 4.

7. 2-Decarboxy-2-hydroxymethyl-16,16-difluoro-19(R)-19-hydroxy-PGF$_{1\alpha}$, a compound according to claim 4.

8. A compound according to claim 3, wherein R₂ is hydrogen.

9. 2-Decarboxy-2-hydroxymethyl-11-deoxy-19(R)-19-hydroxy-PGF$_{1\alpha}$, a compound according to claim 8.

10. 2-decarboxy-2-hydroxymethyl-11-deoxy-16,16-dimethyl-19(R)-19-hydroxy-PGF$_{1\alpha}$, a compound according to claim 8.

11. 2-Decarboxy-2-hydroxymethyl-11-deoxy-16,16-difluoro-19(R)-19-hydroxy-PGF$_{1\alpha}$, a compound according to claim 8.

12. A compound according to claim 3, wherein R₂ is hydroxymethyl.

13. 2-Decarboxy-2-hydroxymethyl-11-deoxy-11α-hydroxymethyl-19(R)-19-hydroxy-PGF$_{1\alpha}$, a compound according to claim 12.

14. 2-Decarboxy-2-hydroxymethyl-11-deoxy-11α-hydroxymethyl-16,16-difluoro-19(R)-19-hydroxy-PGF$_{1\alpha}$, a compound according to claim 12.

15. A compound according to claim 2, wherein W is

16. A compound according to claim 15, wherein R₂ is hydroxyl.

17. 2-Decarboxy-2-hydroxymethyl-19(R)-19-hydroxy-PGF$_{1\beta}$, a compound according to claim 16.

18. 2-Decarboxy-2-hydroxymethyl-16,16-dimethyl-19(R)-19-hydroxy-PGF$_{1\beta}$, a compound according to claim 16.

19. 2-Decarboxy-2-hydroxymethyl-16,16-difluoro-19(R)-19-hydroxy-PGF$_{1\beta}$, a compound according to claim 16.

20. A compound according to claim 15, wherein R₂ is hydrogen.

21. 2-Decarboxy-2-hydroxymethyl-11-deoxy-19(R)-19-hydroxy-PGF$_{1\beta}$, a compound according to claim 20.

22. 2-Decarboxy-2-hydroxymethyl-11-deoxy-16,16-dimethyl-19(R)-29-hydroxy-PGF$_{1\beta}$, a compound according to claim 20.

23. 2-Decarboxy-2-hydroxymethyl-16,16-difluoro-19(R)-19-hydroxy-PGF$_{1\beta}$, a compound according to claim 20.

24. A compound according to claim 15, wherein R₂ is hydroxymethyl.

25. 2-Decarboxy-2-hydroxymethyl-11-deoxy-11α-hydroxymethyl-19(R)-19-hydroxy-PGF$_{1\beta}$, a compound according to claim 24.

26. 2-Decarboxy-2-hydroxymethyl-11-deoxy-11α-hydroxymethyl-16,16-dimethyl-19(R)-19-hydroxy-PGF$_{1\beta}$, a compound according to claim 24.

27. 2-Decarboxy-2-hydroxymethyl-11-deoxy-11α-hydroxymethyl-16,16-difluoro-19(R)-19-hydroxy-PGF$_{1\beta}$, a compound according to claim 24.

28. A compound according to claim 2, wherein W is

29. A compound according to claim 28, wherein R₂ is hydrogen.

30. A compound according to claim 29, wherein X is trans—CH=CH—.

31. 2-Decarboxy-2-hydroxymethyl-11-deoxy-19(R)-19-hydroxy-PGE₁, a compound according to claim 30.

32. 2-Decarboxy-2-hydroxymethyl-11-deoxy-16,16-dimethyl-19(R)-19-hydroxy-PGE₁, a compound according to claim 30.

33. 2-Decarboxy-2-hydroxymethyl-11-deoxy-16,16-difluoro-19(R)-19-hydroxy-PGE₁, a compound according to claim 30.

34. A compound according to claim 28, wherein R₂ is hydroxymethyl.

35. A compound according to claim 34, wherein X is trans—CH=CH—.

36. 2-Decarboxy-2-hydroxymethyl-11-deoxy-11α-hydroxymethyl-19(R)-19-hydroxy-PGE₁, a compound according to claim 35.

37. 2-Decarboxy-2-hydroxymethyl-11-deoxy-11α-hydroxymethyl-16,16-dimethyl-19(R)-19-hydroxy-PGE₁, a compound according to claim 26.

38. 2-Decarboxy-2-hydroxymethyl-11-deoxy-11α-hydroxymethyl-16,16-difluoro-19(R)-19-hydroxy-PGE₁, a compound according to claim 26.

39. A compound according to claim 2, wherein W is

40. A compound according to claim 39, wherein R₂ is hydroxyl.

41. A compound according to claim 40, wherein X is trans—CH=CH—.

42. 2-Decarboxy-2-hydroxymethyl-9-deoxo-9-methylene-19(R)-19-hydroxy-PGE₁, a compound according to claim 41.

43. 2-Decarboxy-2-hydroxymethyl-9-deoxo-9-methylene-16,16-dimethyl-19(R)-19-hydroxy-PGE₁, a compound according to claim 41.

44. 2-Decarboxy-2-hydroxymethyl-9-deoxo-9-methylene-16,16-difluoro-19(R)-19-hydroxy-PGE₁, a compound according to claim 41.

45. A compound according to claim 39, wherein R₂ is hydrogen.

46. A compound according to claim 45, wherein X is trans—CH=CH—.

47. 2-Decarboxy-2-hydroxymethyl-9-deoxo-9-methylene-11-deoxy-19(R)-19-hydroxy-PGE₁, a compound according to claim 45.

48. 2-Decarboxy-2-hydroxymethyl-9-deoxo-9-methylene-11-deoxy-16,16-dimethyl-19(R)-19-hydroxy-PGE₁, a compound according to claim 45.

49. 2-Decarboxy-2-hydroxymethyl-9-deoxo-9-methylene-11-deoxy-16,16-difluoro-19(R)-19-hydroxy-PGE₁, a compound according to claim 45.

50. A compound according to claim 39, wherein R₂ is hydroxymethyl.

51. A compound according to claim 49, wherein X is trans—CH=CH—.

52. 2-Decarboxy-2-hydroxymethyl-9-deoxo-9-methylene-11-deoxy-11α-hydroxymethyl-19(R)-19-hydroxy-PGE₁, a compound according to claim 50.

53. 2-Decarboxy-2-hydroxymethyl-9-deoxo-9-methylene-11-deoxy-11α-hydroxymethyl-16,16-dimethyl-19(R)-19-hydroxy-PGE₁, a compound according to claim 50.

54. 2-Decarboxy-2-hydroxymethyl-9-deoxo-9-methylene-11-deoxy-11α-hydroxymethyl-16,16-difluoro-19(R)-19-hydroxy-PGE₁, a compound according to claim 50.

* * * * *

UNITED STATES PATENT OFFICE
CERTIFICATE OF CORRECTION

Patent No. 4,228,104   Dated 14 October 1980

Inventor(s) John C. Sih

It is certified that error appears in the above-identified patent and that said Letters Patent are hereby corrected as shown below:
In the Abstract, that portion of the formula reading

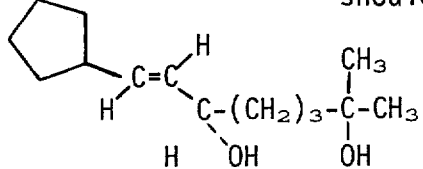   should read   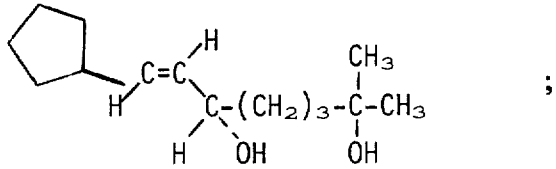   ;

Column 5, lines 17-22,

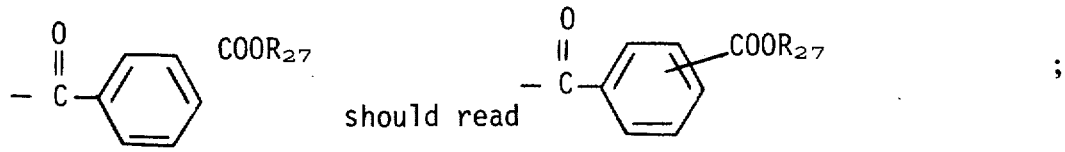

Column 25, lines 37-38, "(trans-$(CH_2)_3$-CH1=CH-" should read -- trans-$(CH_2)_3$-CH=CH- --;
Column 26, line 37, "D  III  of" should be deleted;
Column 47, line 16, "formula-CXXXVII" should read -- formula-CXXXVIII --; line 26, "formula-CXXIX" should read -- formula-CXXXIX --;
Column 49, line 34, "2.70-120" should read -- 2.70-1.20 --;
Column 53, line 8, "5.184 .81," should read -- 5.18-4.81, --; line 61, "and diazomethane" should read -- with diazomethane --;
Column 57, line 27, "4.483.36," should read -- 4.48-3.36, --;
Column 65, line 49, "or "19(+)"" should read -- or "19($\pm$)" --;
Column 66, the formulas at lines 45-68, should appear as follows:

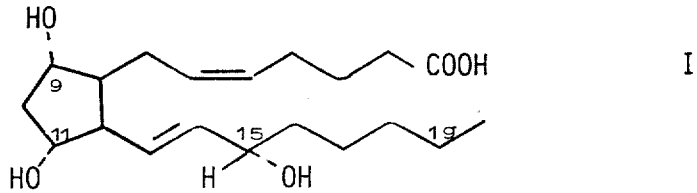

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

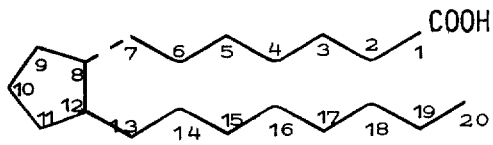

II

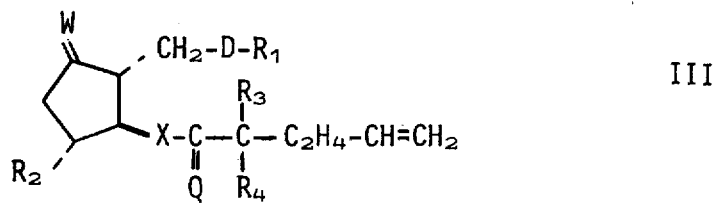

III

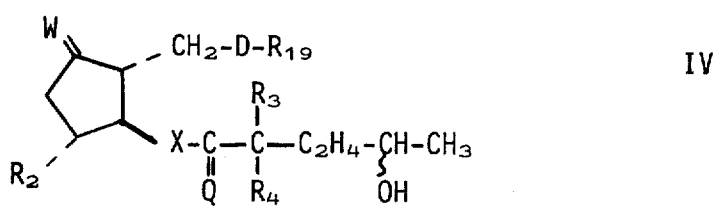

IV

Formulas hereinafter identifed by column and line numbers should appear as follows instead of as appear in the printed patent:
Column 67, lines 19-25,

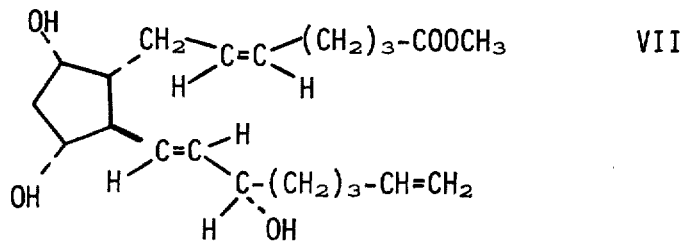

VII

Page 3 of 34 Pages

UNITED STATES PATENT OFFICE
CERTIFICATE OF CORRECTION

Patent No. 4,228,104                    Dated 14 October 1980

Inventor(s) John C. Sih

It is certified that error appears in the above-identified patent and that said Letters Patent are hereby corrected as shown below:

Column 67, lines 36-43,

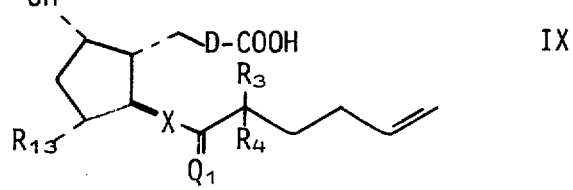

Column 69, lines 30-40,

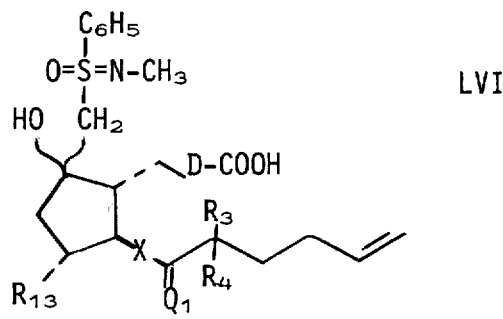

Column 71, lines 5-12,

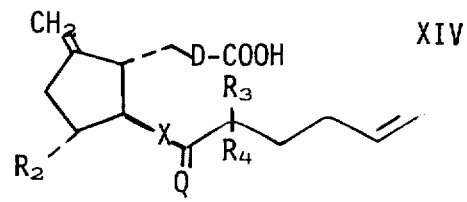

Column 71, lines 30-54

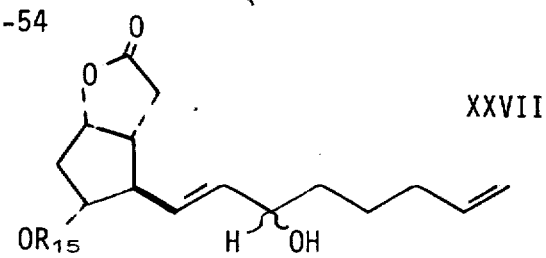

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

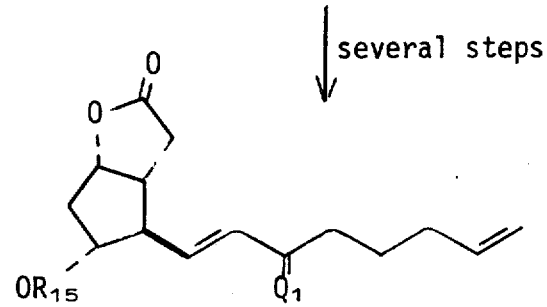

XXVIII

Column 72, lines 42-55,

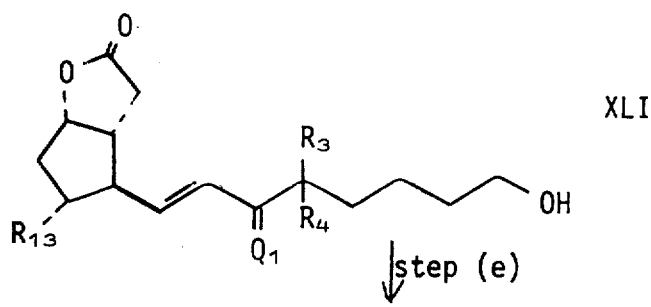

XLI

Column 74, lines 21-68,

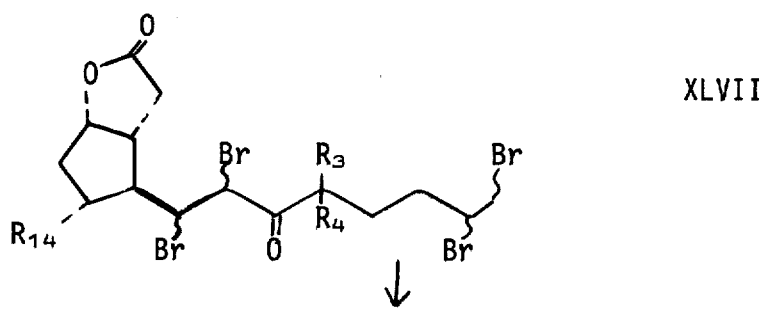

XLVII

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

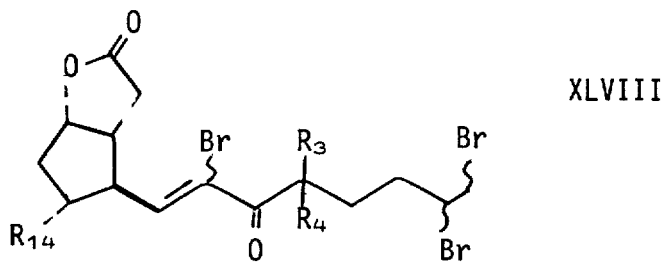

XLVIII

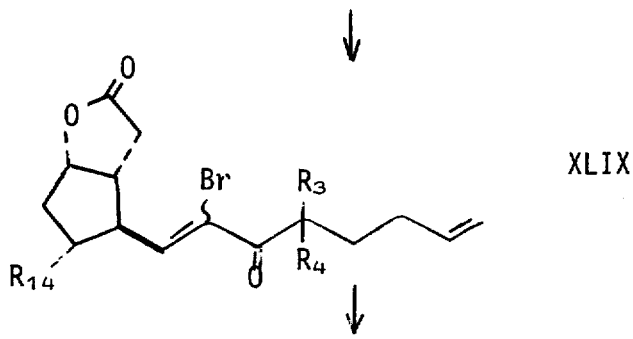

XLIX

Column 75, lines 4-26,

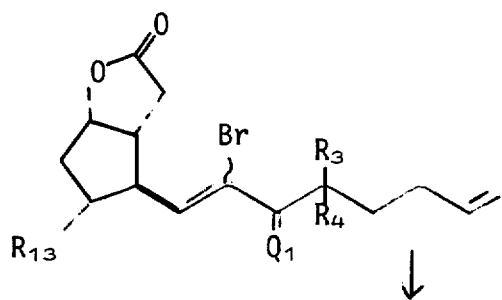

L

Page 6 of 34 Pages

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

Column 76, lines 6-30,

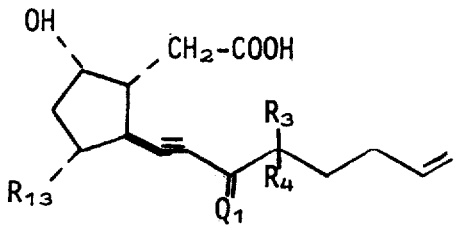

Column 77, lines 38-68,

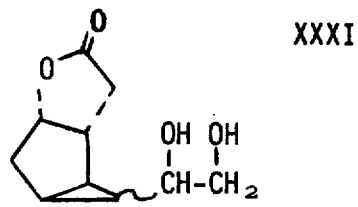

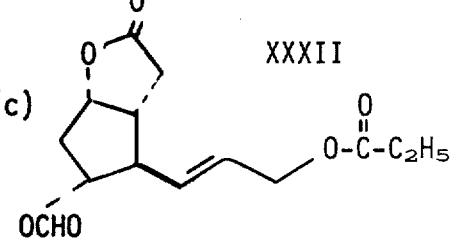

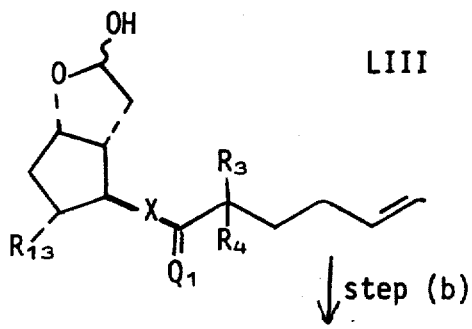

UNITED STATES PATENT OFFICE
CERTIFICATE OF CORRECTION

Patent No. 4,228,104           Dated 14 October 1980

Inventor(s) John C. Sih

It is certified that error appears in the above-identified patent and that said Letters Patent are hereby corrected as shown below:

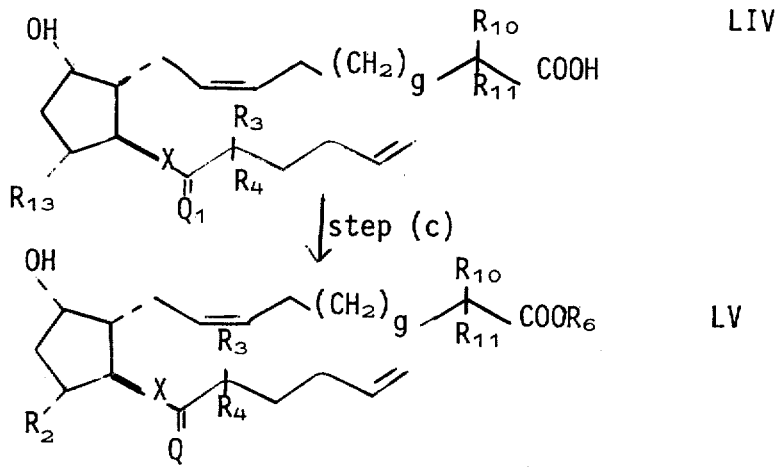

Column 78, lines 5-55,

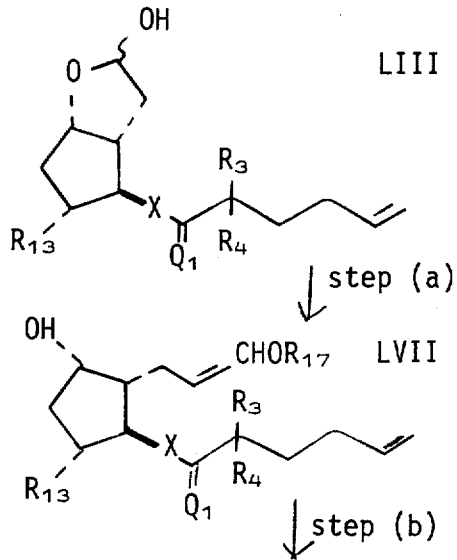

United States Patent Office

CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

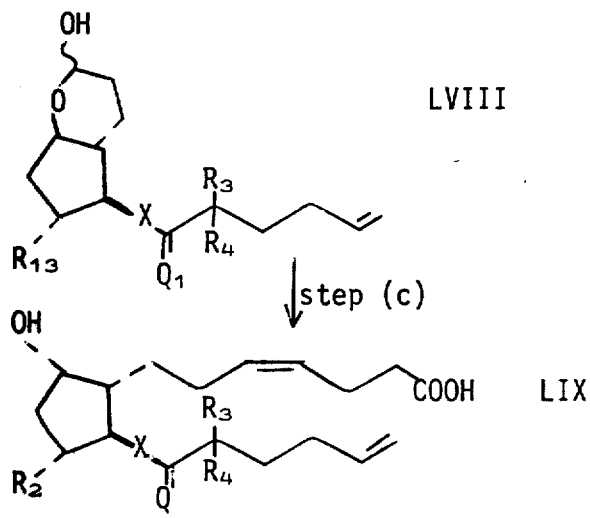

Column 79, lines 5-68,

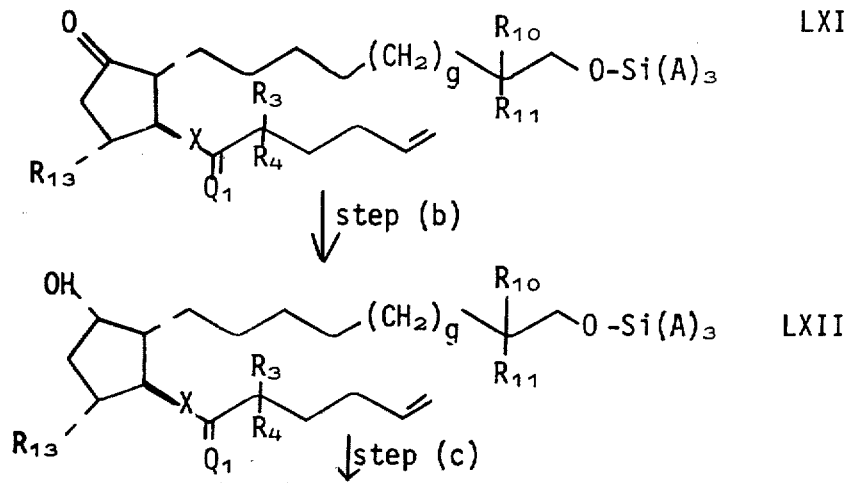

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

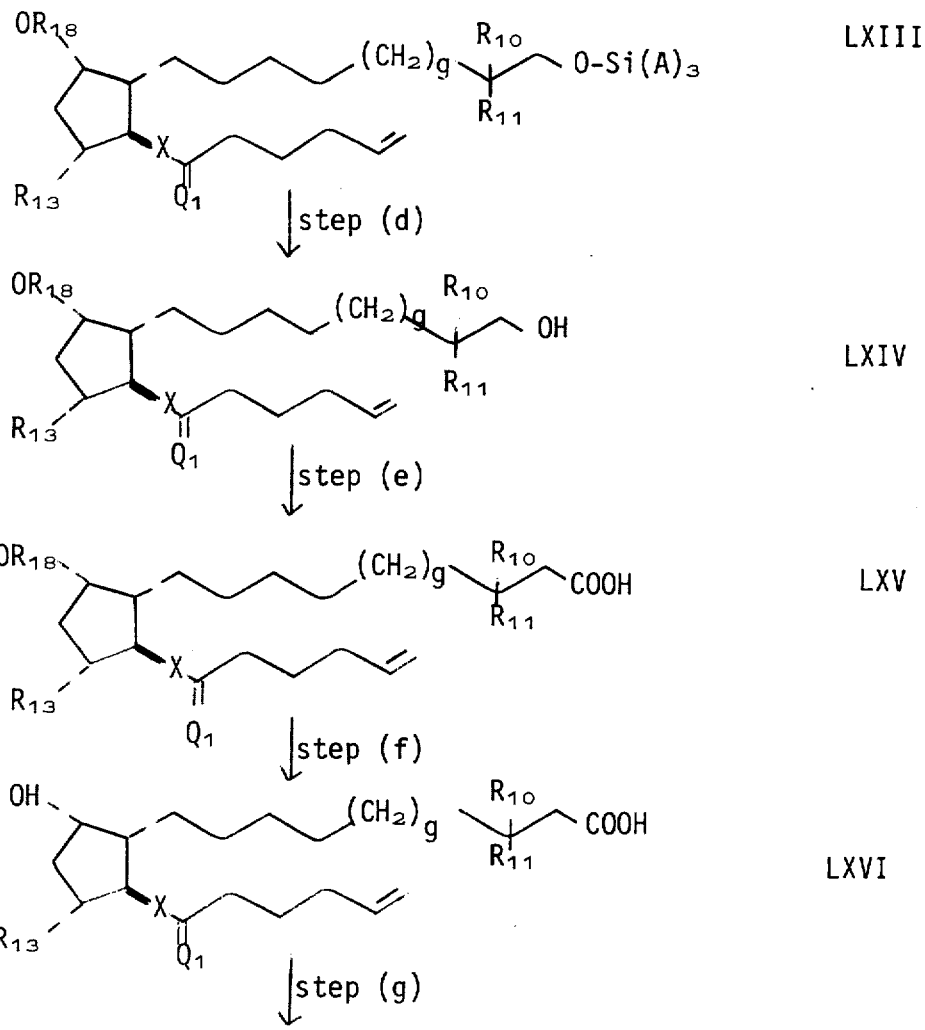

UNITED STATES PATENT OFFICE
CERTIFICATE OF CORRECTION

Patent No. 4,228,104　　　　　Dated 14 October 1980

Inventor(s)　John C. Sih

It is certified that error appears in the above-identified patent and that said Letters Patent are hereby corrected as shown below:

Column 80, lines 28-68,

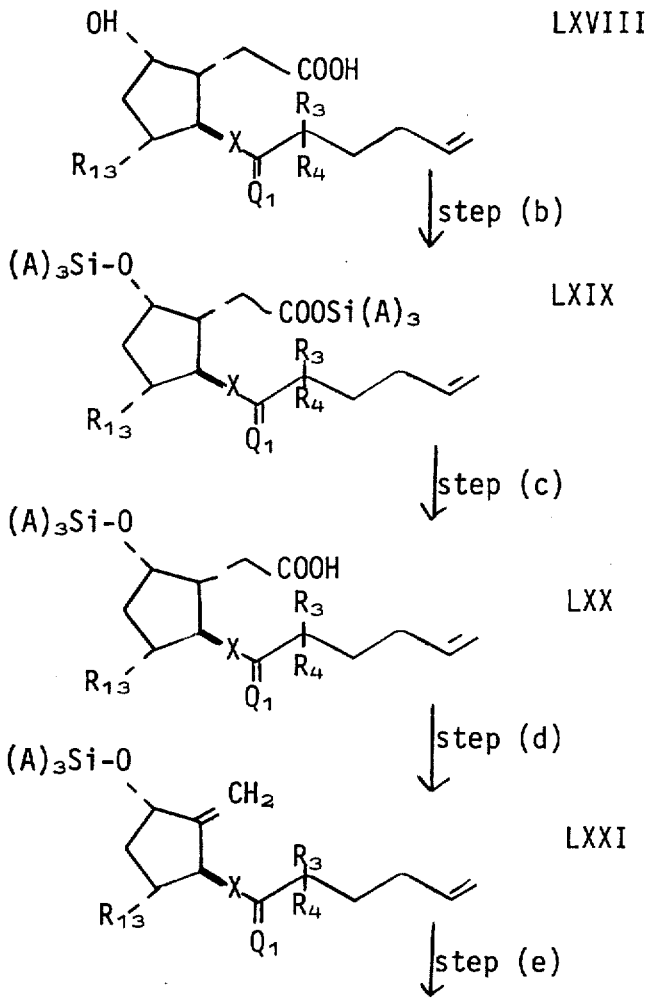

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

Column 81, lines 4-12,

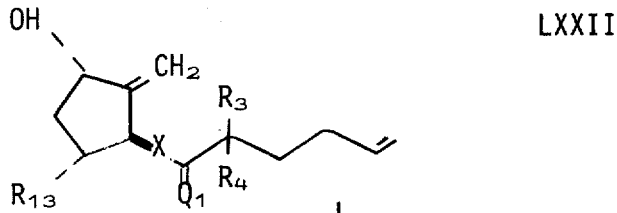

LXXII

↓ step (f)

Column 82, lines 28-68,

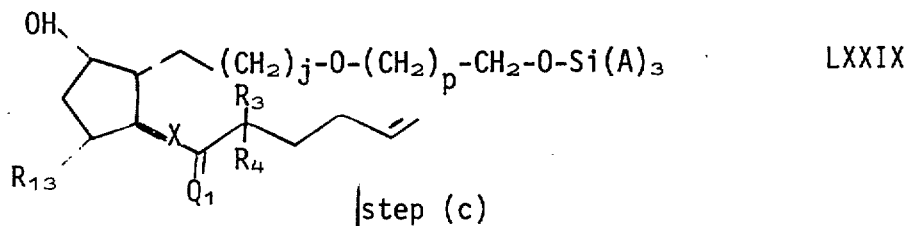

LXXIX

↓ step (c)

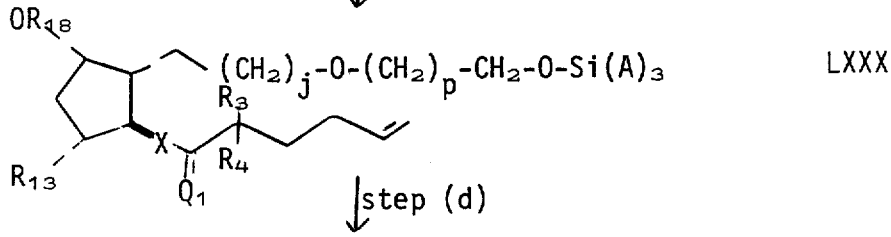

LXXX

↓ step (d)

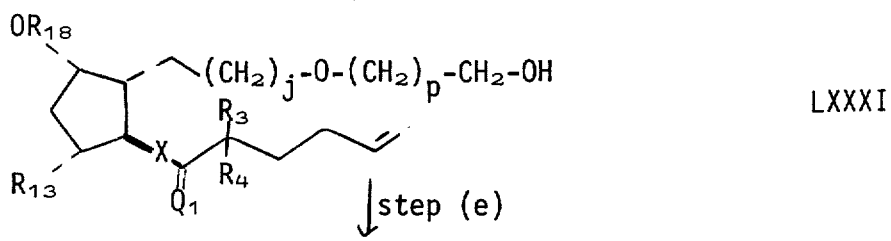

LXXXI

↓ step (e)

UNITED STATES PATENT OFFICE
CERTIFICATE OF CORRECTION

Patent No. 4,228,104   Dated 14 October 1980

Inventor(s) John C. Sih

It is certified that error appears in the above-identified patent and that said Letters Patent are hereby corrected as shown below:

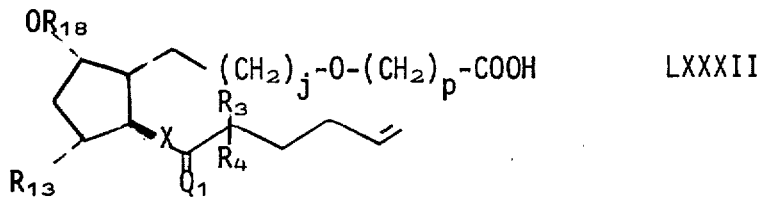

LXXXII

Column 83, lines 3-55,

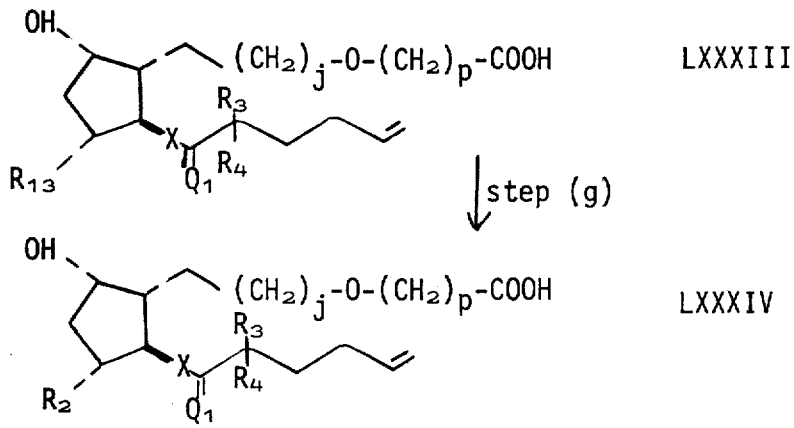

LXXXIII step (g)

LXXXIV

CHART 13

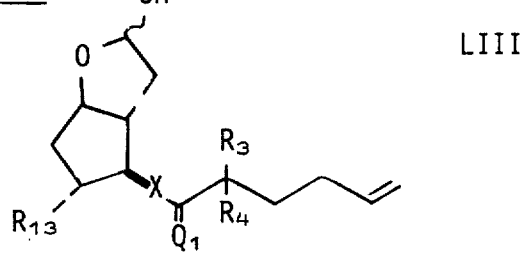

LIII

UNITED STATES PATENT OFFICE
CERTIFICATE OF CORRECTION

Patent No. 4,228,104   Dated 14 October 1980

Inventor(s) John C. Sih

It is certified that error appears in the above-identified patent and that said Letters Patent are hereby corrected as shown below:

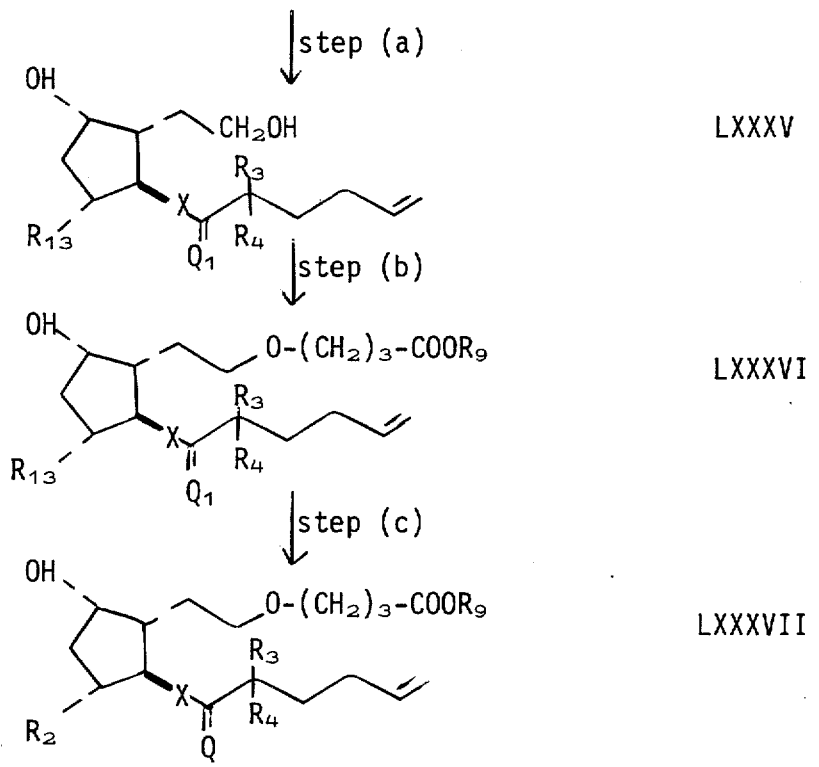

UNITED STATES PATENT OFFICE
CERTIFICATE OF CORRECTION

Patent No. 4,228,104    Dated 14 October 1980

Inventor(s) John C. Sih

It is certified that error appears in the above-identified patent and that said Letters Patent are hereby corrected as shown below:

Column 84, lines 15-44,

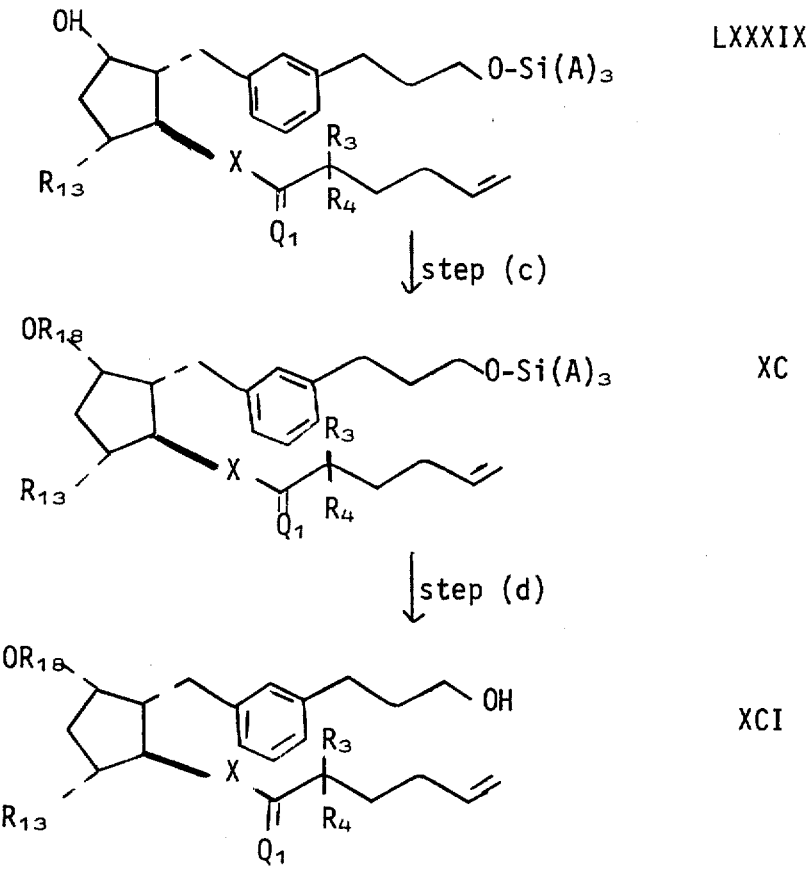

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

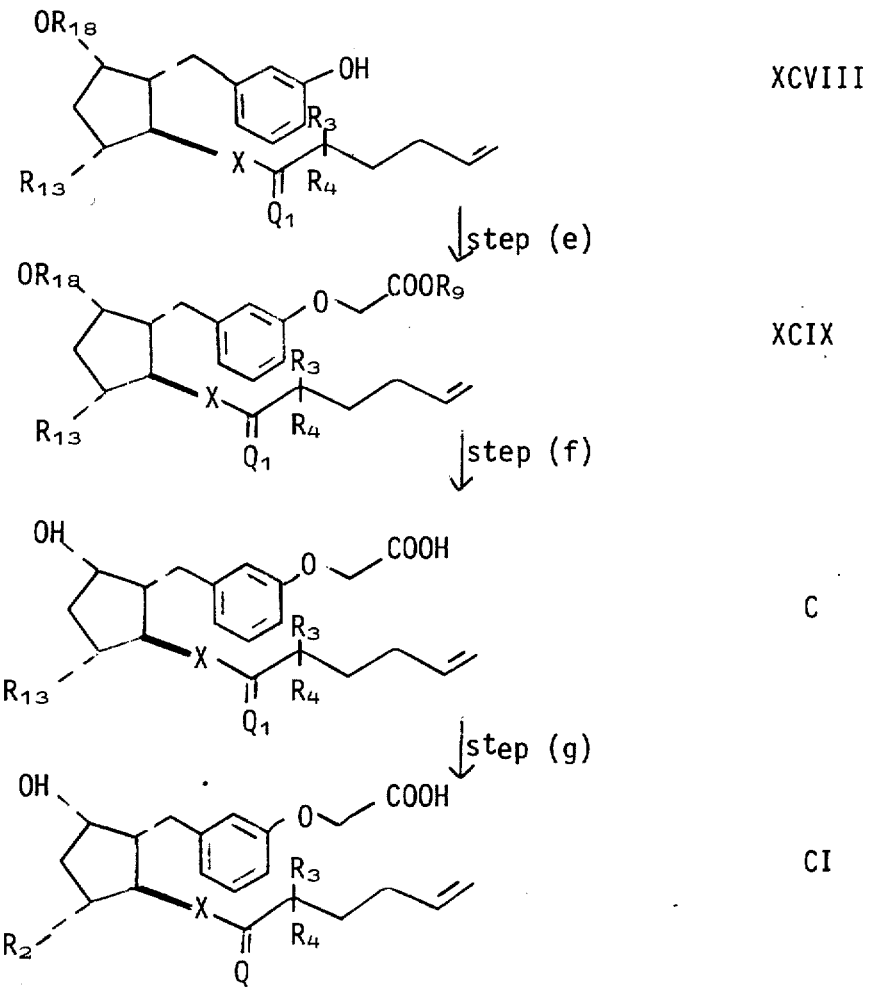

UNITED STATES PATENT OFFICE
CERTIFICATE OF CORRECTION

Patent No. 4,228,104      Dated 14 October 1980

Inventor(s) John C. Sih

It is certified that error appears in the above-identified patent and that said Letters Patent are hereby corrected as shown below:

Column 85, lines 4-11,

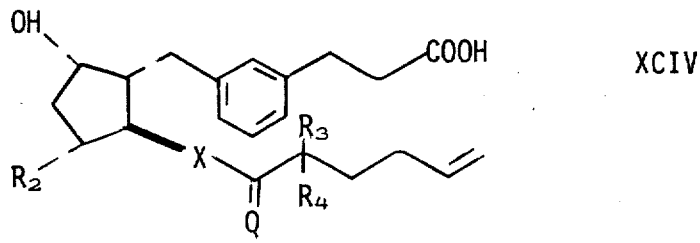

Column 85, line 36 through Column 86, line 35,

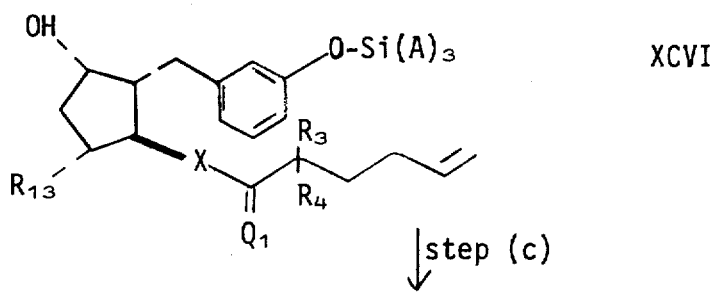

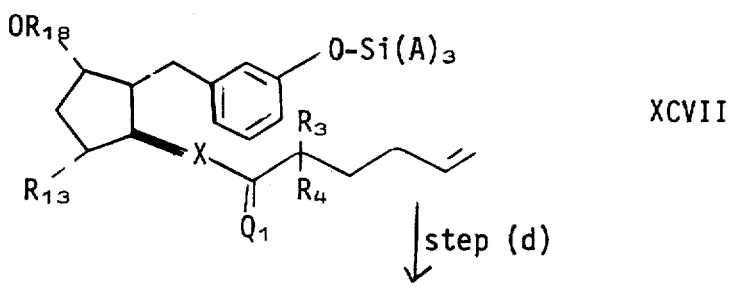

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

Column 86, lines 40-68,

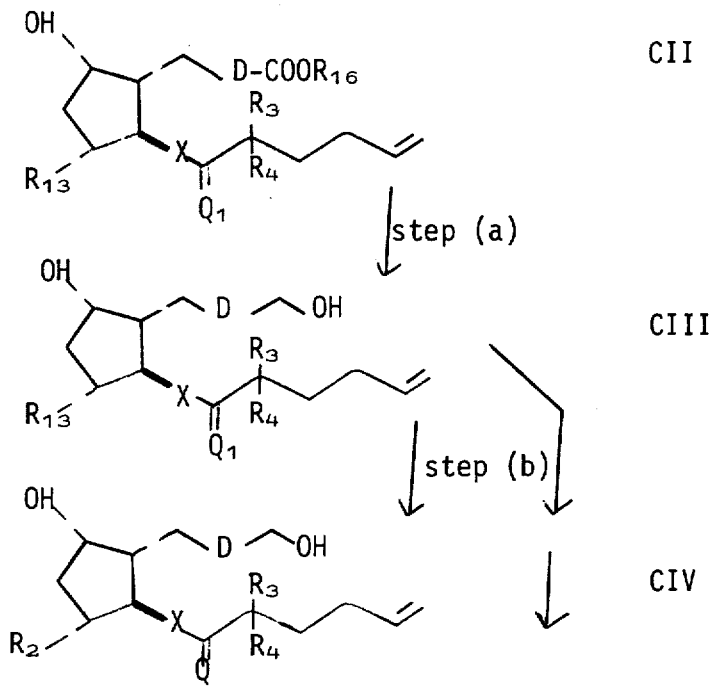

Column 87, lines 5-14,

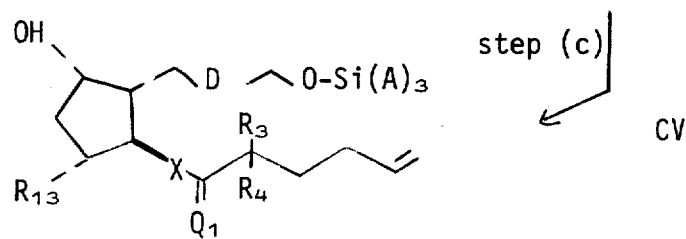

UNITED STATES PATENT OFFICE
CERTIFICATE OF CORRECTION

Patent No. 4,228,104　　　　　　　　Dated 14 October 1980

Inventor(s) John C. Sih

It is certified that error appears in the above-identified patent and that said Letters Patent are hereby corrected as shown below:

Column 87, lines 27-35,

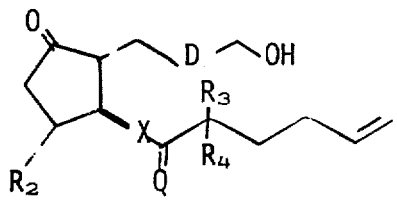

CVII

Column 88, lines 4-23,

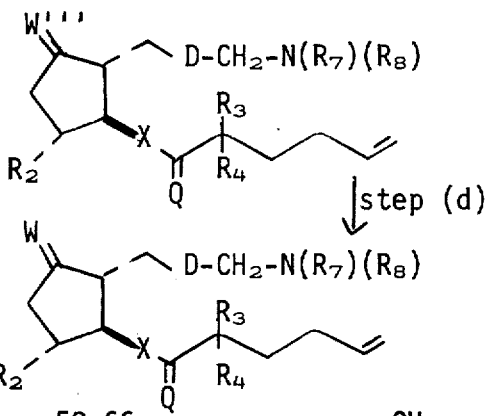

CXI step (d)

CXII

Column 88, lines 58-66,

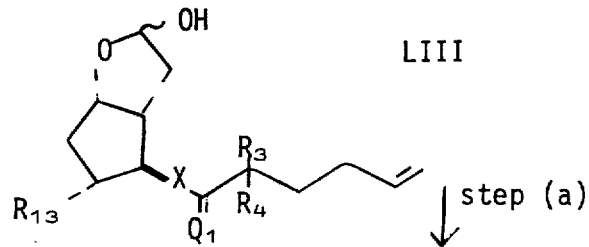

LIII step (a)

UNITED STATES PATENT OFFICE
CERTIFICATE OF CORRECTION

Patent No. 4,228,104    Dated 14 October 1980

Inventor(s) John C. Sih

It is certified that error appears in the above-identified patent and that said Letters Patent are hereby corrected as shown below:

Column 89, lines 3-10,

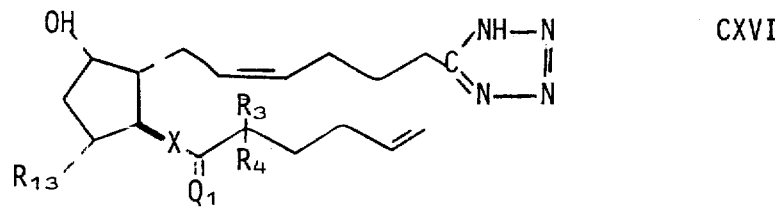

CXVI

Column 90, lines 5-55,

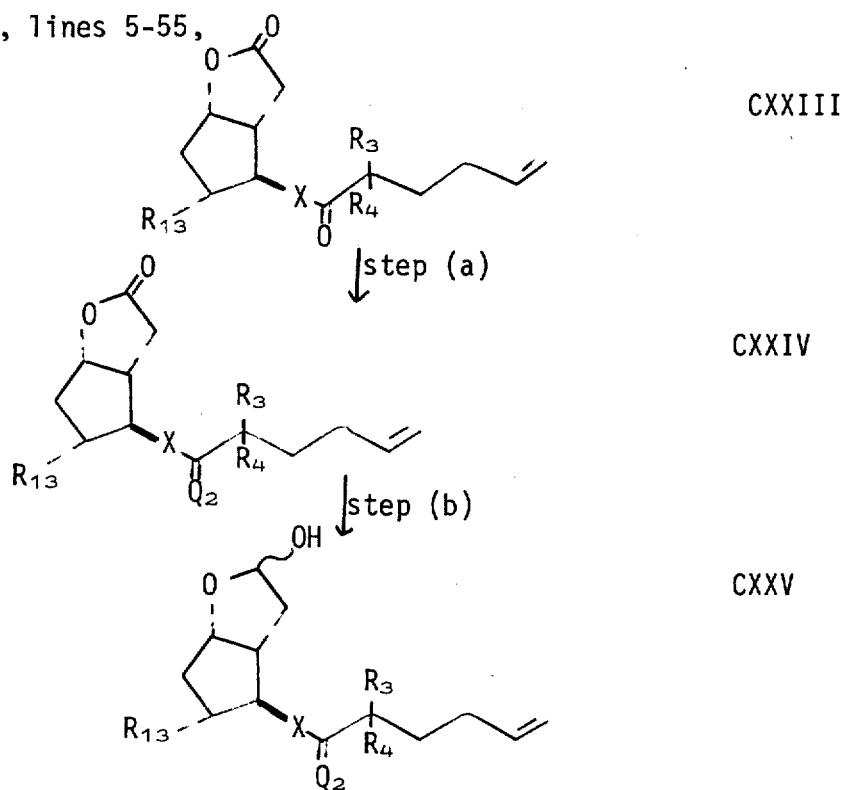

CXXIII

CXXIV

CXXV

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

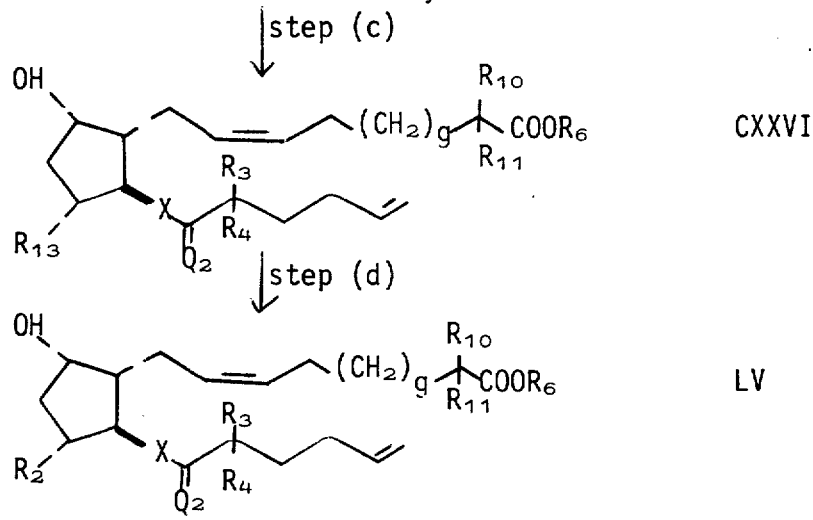

Column 91, lines 13-34,

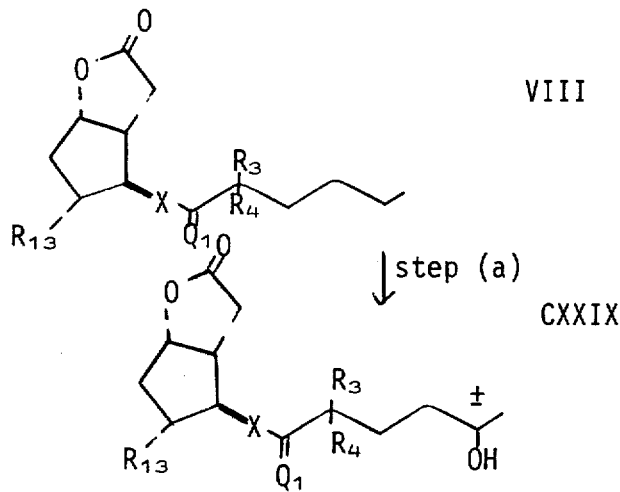

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

Column 92, lines 45-65,

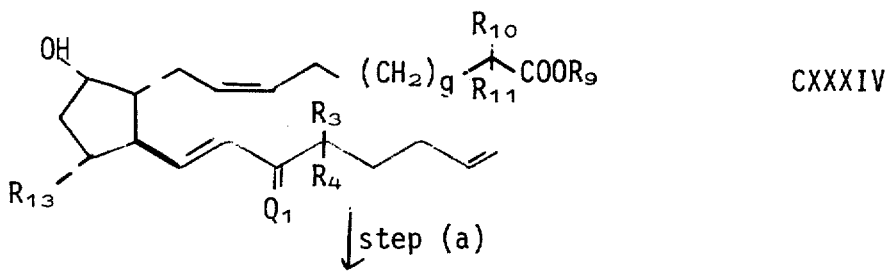

Column 93, lines 4-68,

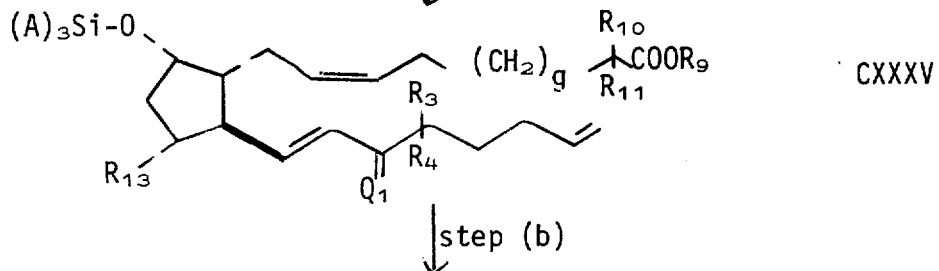

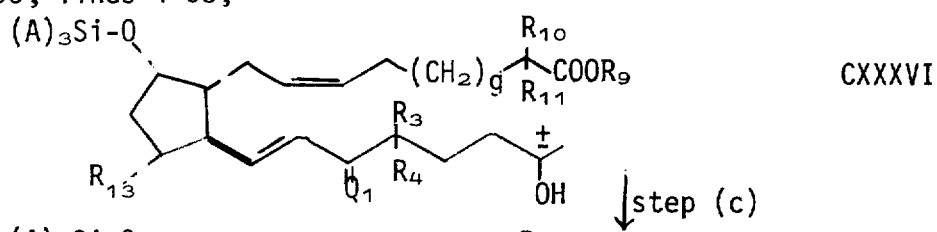

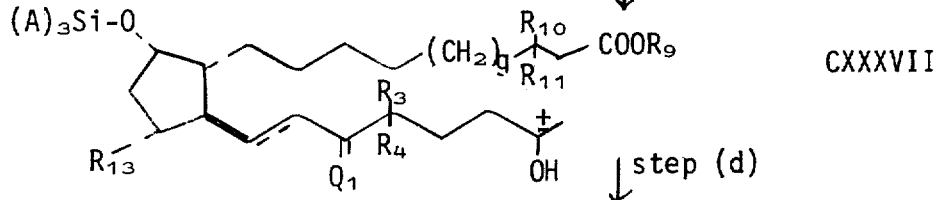

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

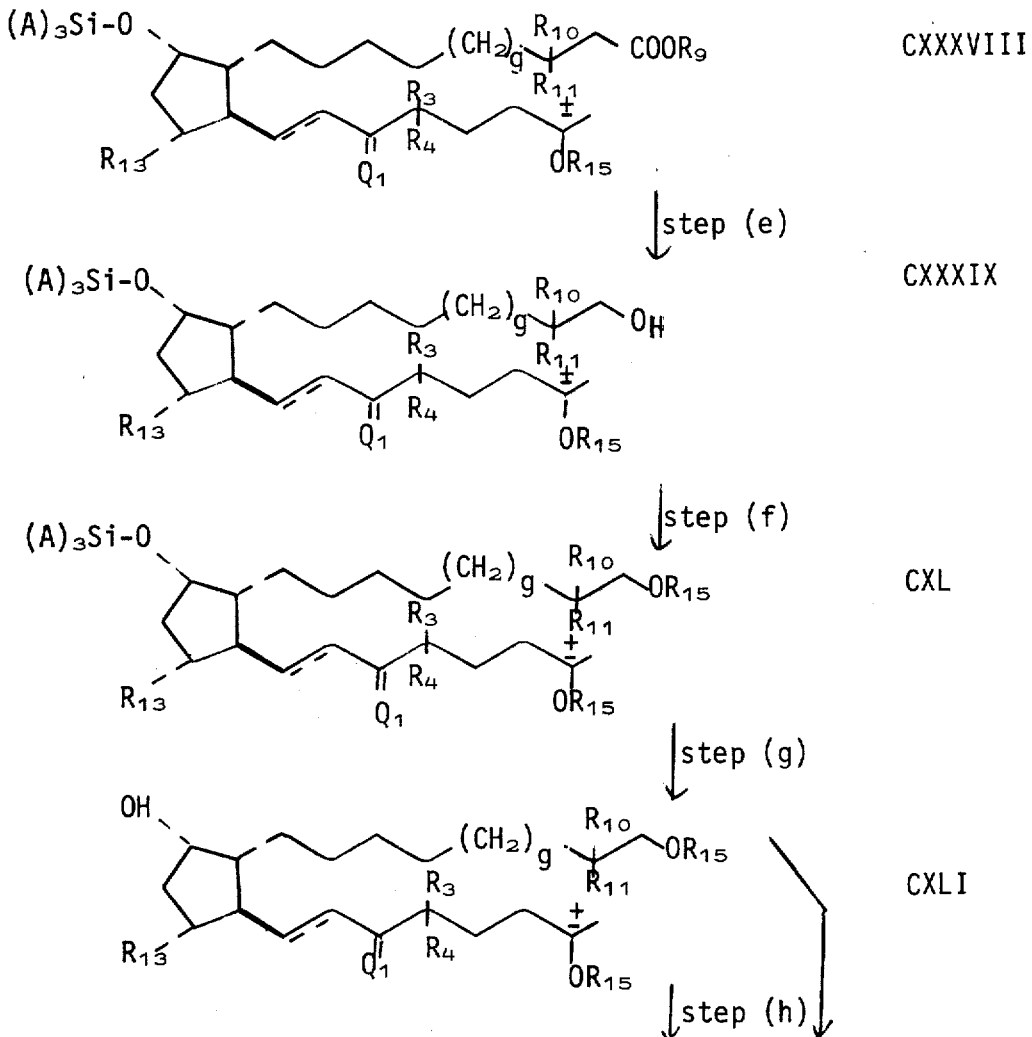

UNITED STATES PATENT OFFICE
CERTIFICATE OF CORRECTION

Patent No. 4,228,104    Dated 14 October 1980

Inventor(s) John C. Sih

It is certified that error appears in the above-identified patent and that said Letters Patent are hereby corrected as shown below:

Column 95, lines 4-44,

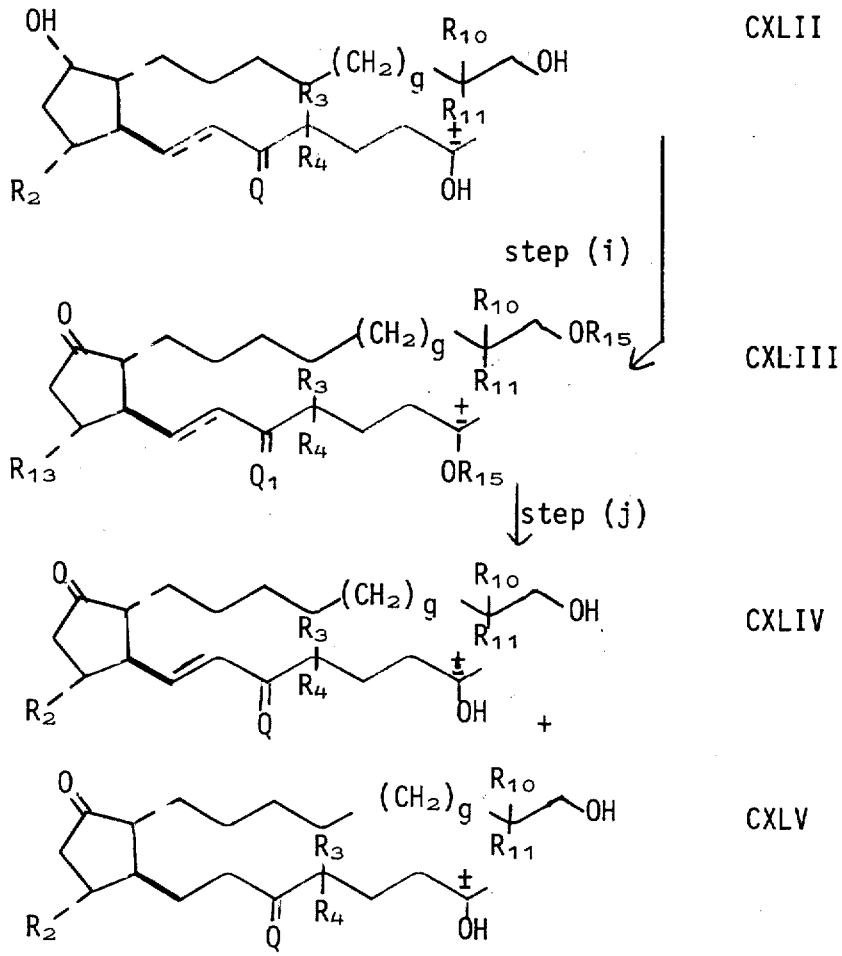

UNITED STATES PATENT OFFICE
CERTIFICATE OF CORRECTION

Patent No. 4,228,104      Dated 14 October 1980

Inventor(s)   John C. Sih

It is certified that error appears in the above-identified patent and that said Letters Patent are hereby corrected as shown below:

Column 95, lines 48-67 and Column 96, lines 48-67,

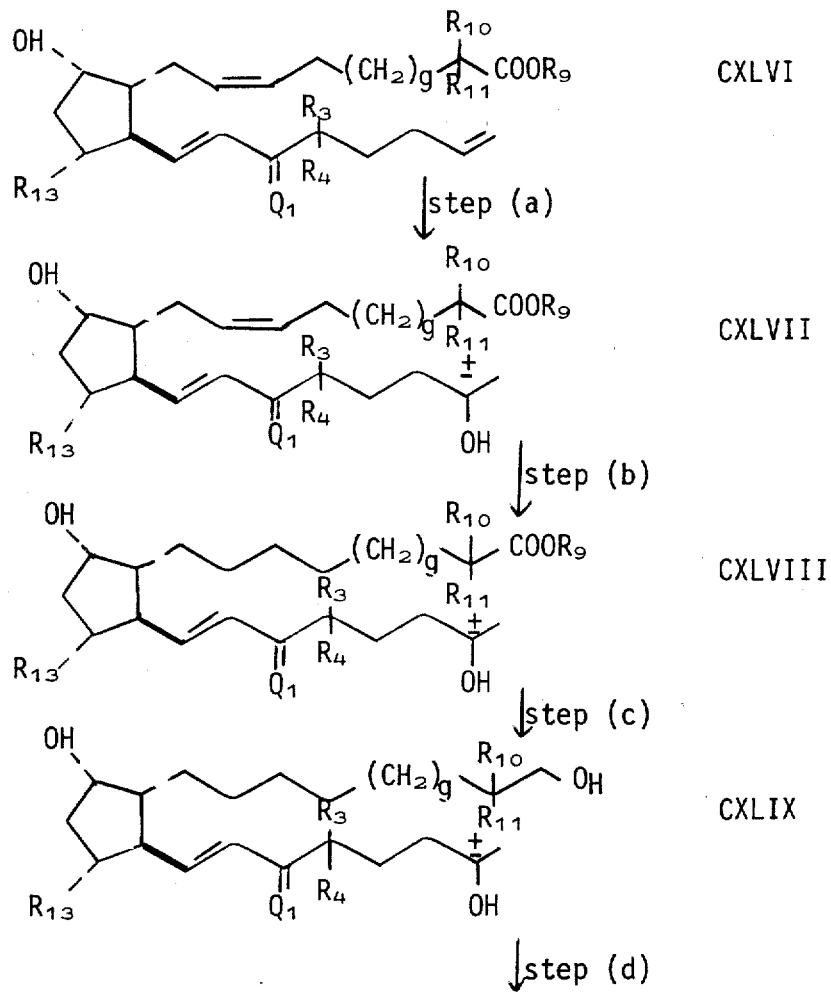

UNITED STATES PATENT OFFICE
CERTIFICATE OF CORRECTION

Patent No. 4,228,104    Dated 14 October 1980

Inventor(s) John C. Sih

It is certified that error appears in the above-identified patent and that said Letters Patent are hereby corrected as shown below:

Column 97, lines 6-12,

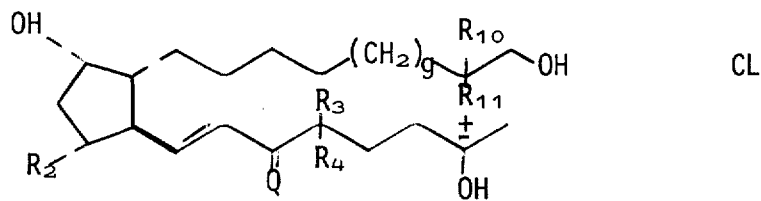

Column 97, lines 31-52

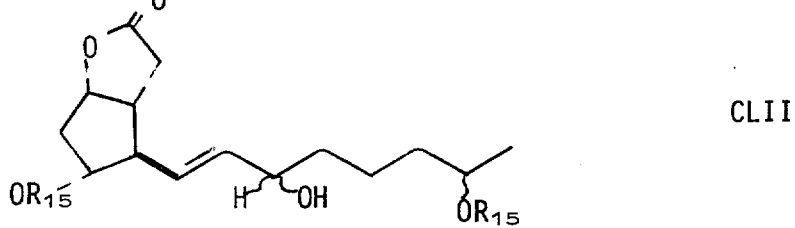

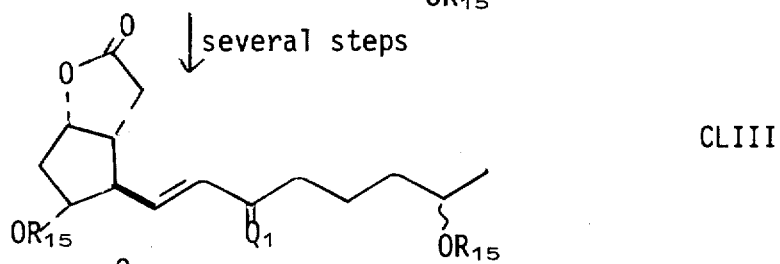

Column 98, lines 5-45,

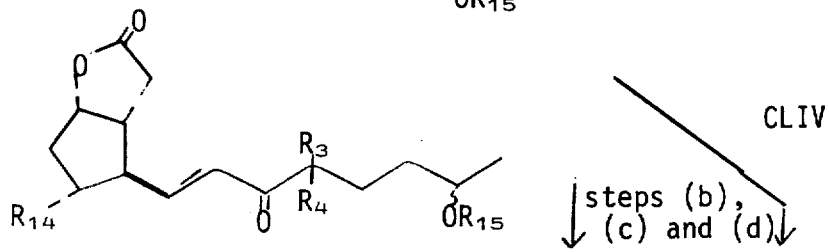

UNITED STATES PATENT OFFICE
CERTIFICATE OF CORRECTION

Patent No. 4,228,104          Dated 14 October 1980

Inventor(s) John C. Sih

It is certified that error appears in the above-identified patent and that said Letters Patent are hereby corrected as shown below:

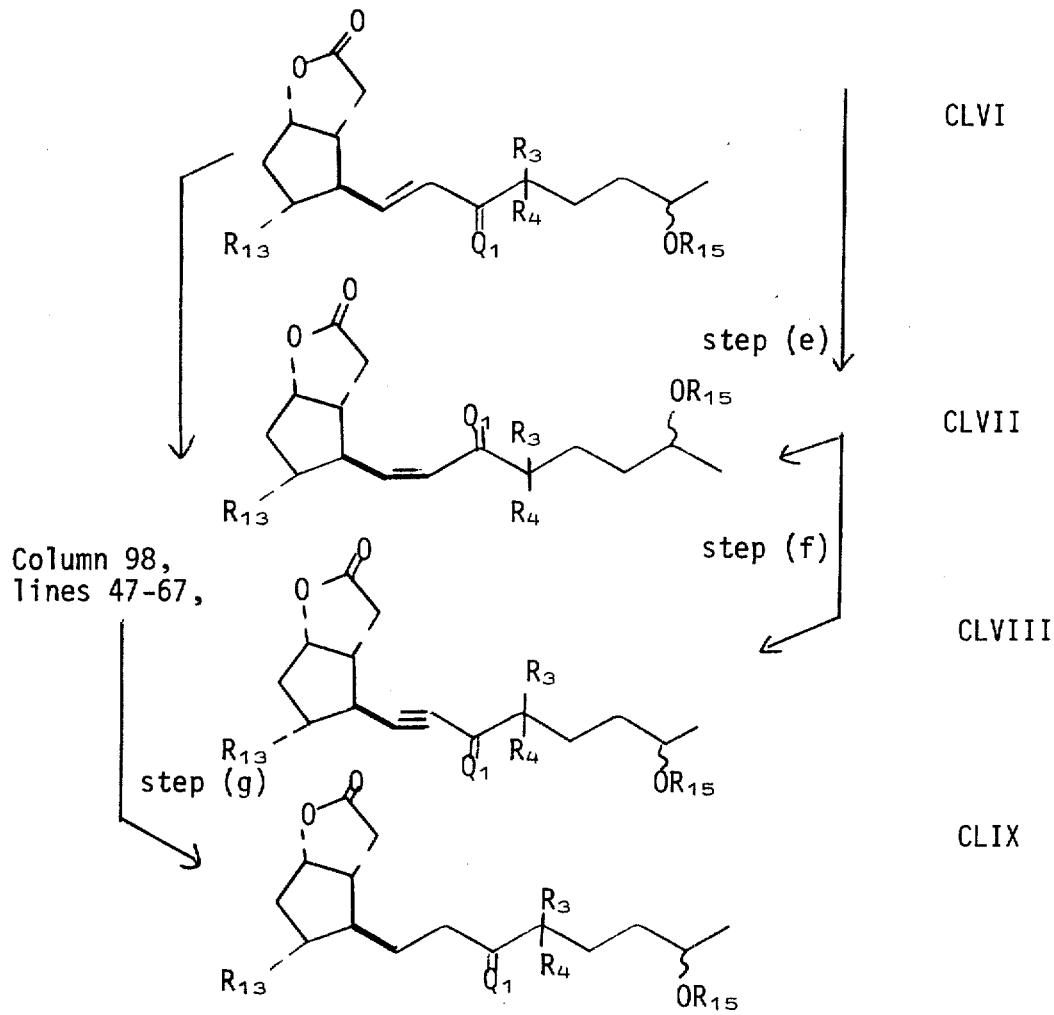

Column 98, lines 47-67,

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

Column 99, lines 7-41,

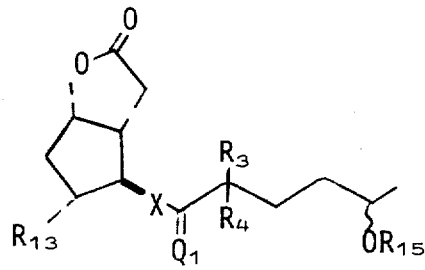  CLXII

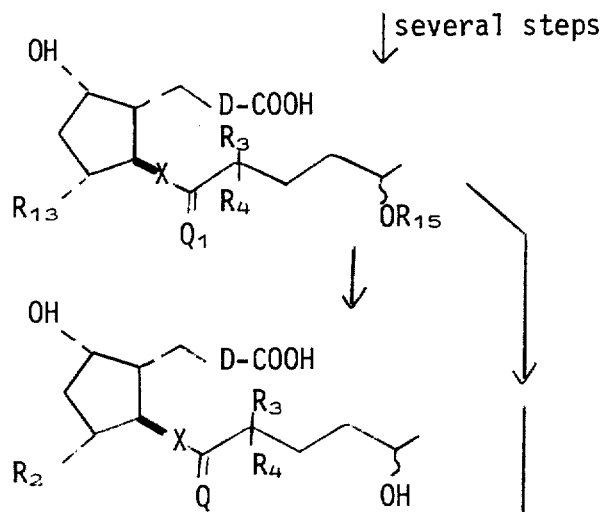

CLXIII

CLXIV

Column 99, lines 42-68,

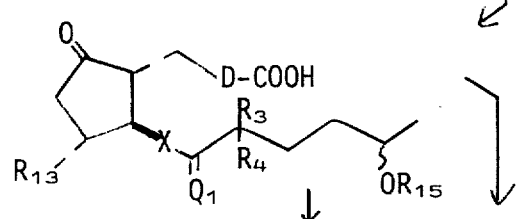  CLXV

UNITED STATES PATENT OFFICE
CERTIFICATE OF CORRECTION

Patent No. 4,228,104    Dated 14 October 1980

Inventor(s) John C. Sih

It is certified that error appears in the above-identified patent and that said Letters Patent are hereby corrected as shown below:

Column 100, lines 6-25,

Column 100, lines 40-51,

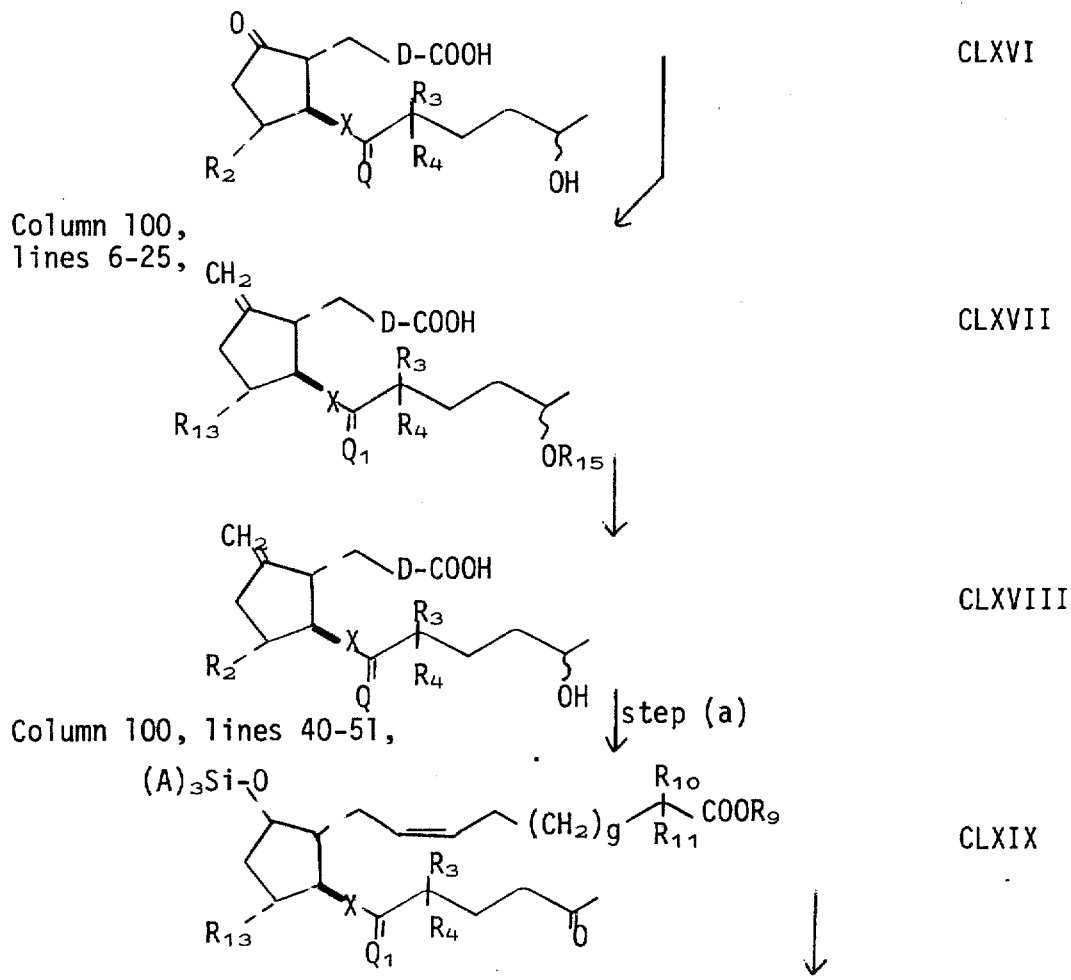

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

Column 101, lines 4-11,

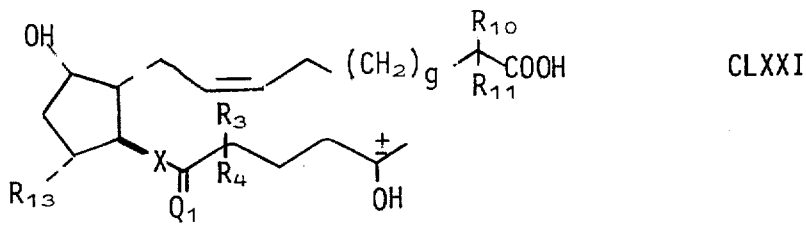

Column 103, lines 33-42,

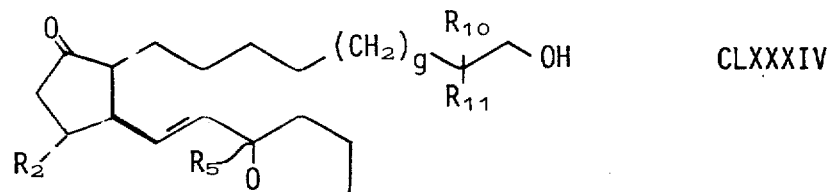

Column 103, lines 47-68,

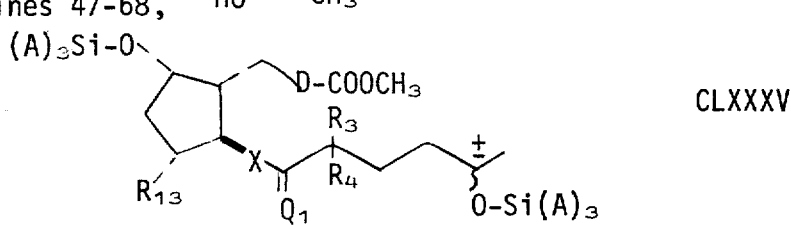

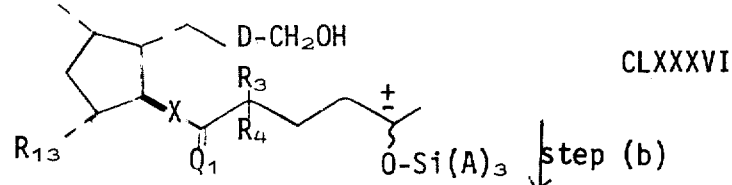

UNITED STATES PATENT OFFICE
CERTIFICATE OF CORRECTION

Patent No. 4,228,104   Dated 14 October 1980

Inventor(s) John C. Sih

It is certified that error appears in the above-identified patent and that said Letters Patent are hereby corrected as shown below:

Column 104, lines 4-35,

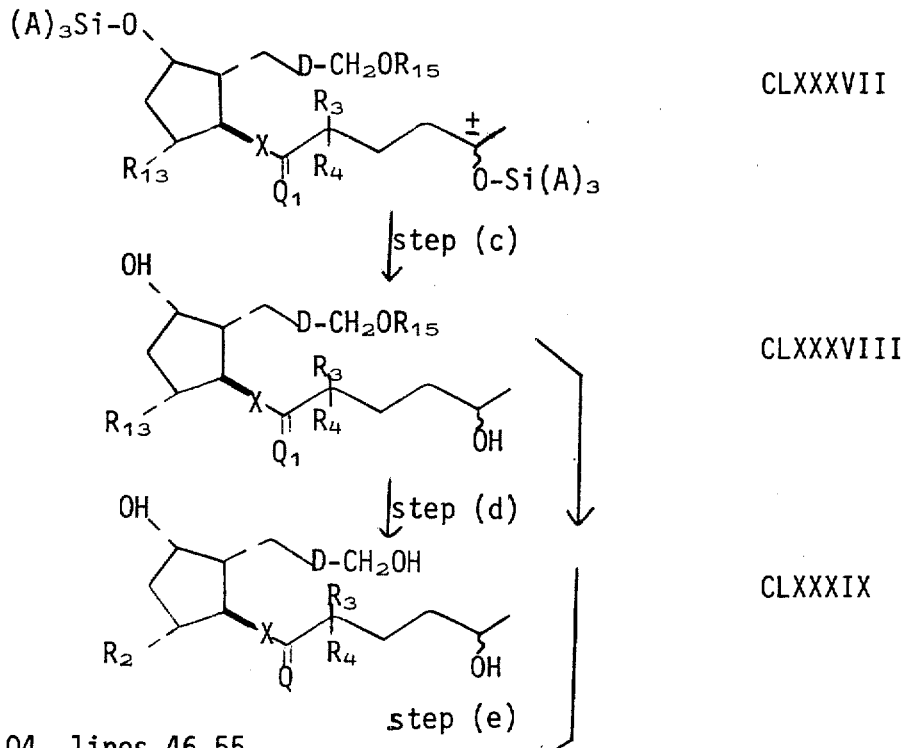

Column 104, lines 46-55,

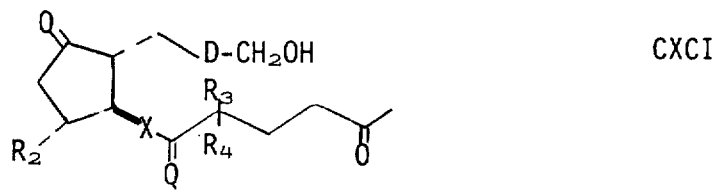

UNITED STATES PATENT OFFICE
CERTIFICATE OF CORRECTION

Patent No. 4,228,104          Dated  14 October 1980

Inventor(s)   John C. Sih

It is certified that error appears in the above-identified patent and that said Letters Patent are hereby corrected as shown below:

Column 105, lines 29-50,

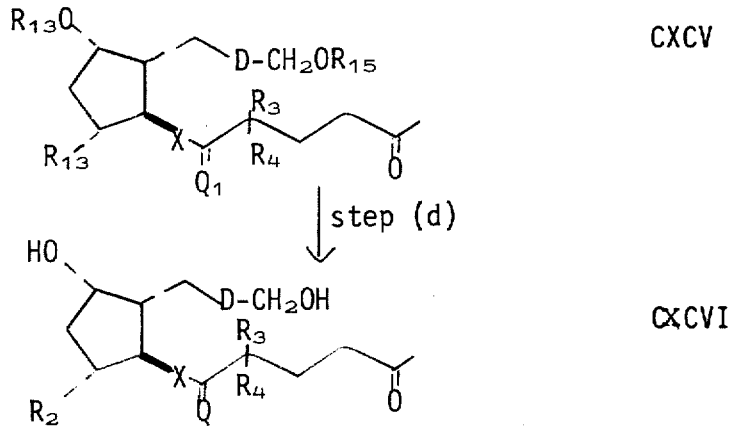

Column 105, lines 56-68,

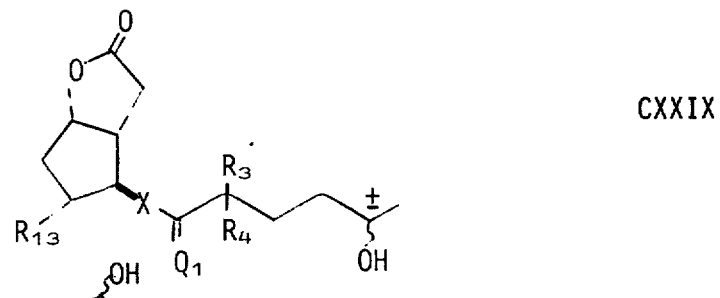

Column 106, lines 32-42,

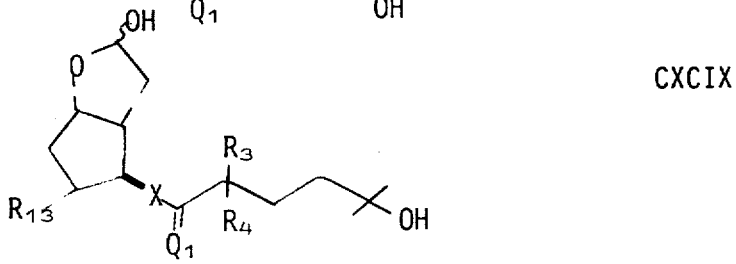

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

Column 108, lines 3-12,

Column 109, lines 44-53,

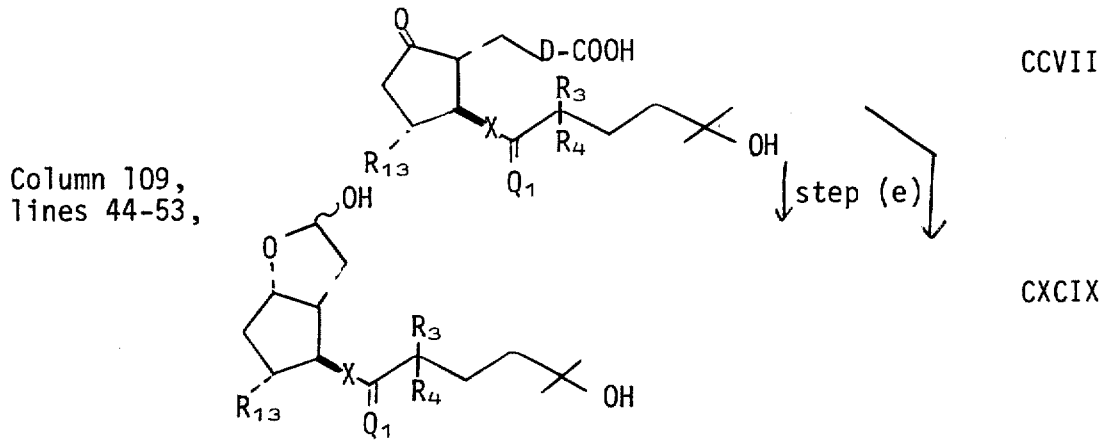

CCVII

CXCIX

Column 110, lines 4-13,

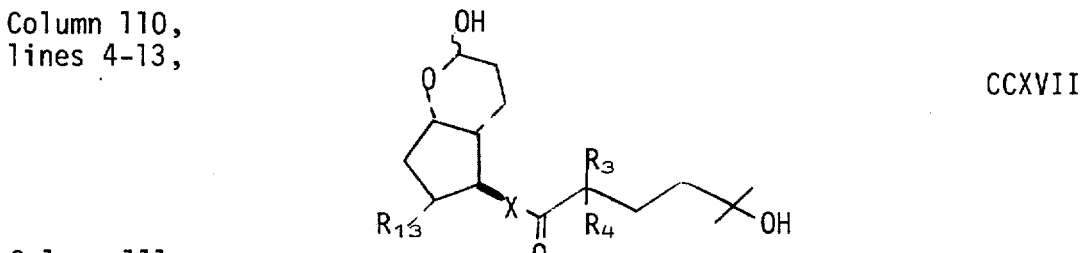

CCXVII

Column 111, lines 46-54,

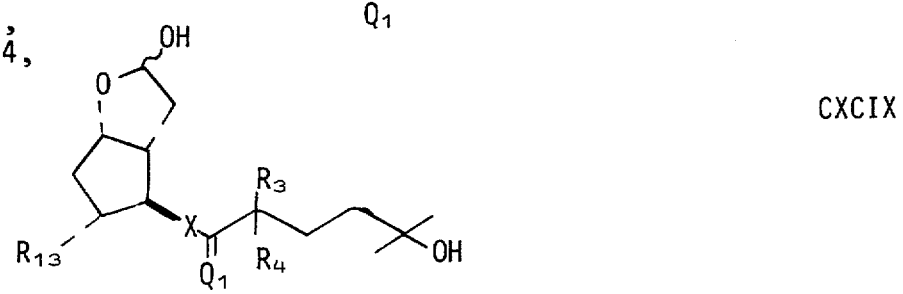

CXCIX

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

Column 112, lines 46-55,

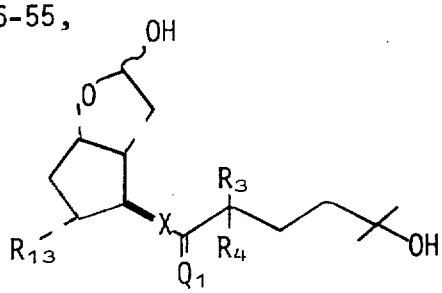

CXCIX

Column 114, lines 3-12,

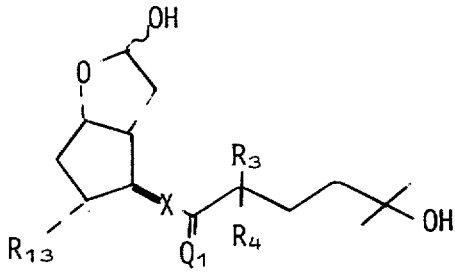

CXCIX

Column 121, lines 7-15,

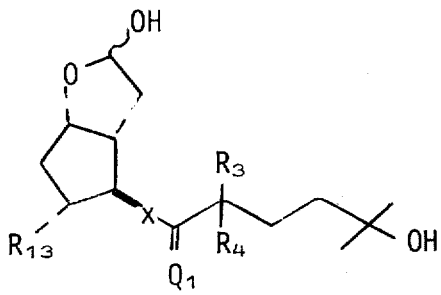

CXCIX

UNITED STATES PATENT OFFICE
CERTIFICATE OF CORRECTION

Patent No. 4,228,104  Dated 14 October 1980

Inventor(s) John C. Sih

It is certified that error appears in the above-identified patent and that said Letters Patent are hereby corrected as shown below:

Column 122, lines 25-33,

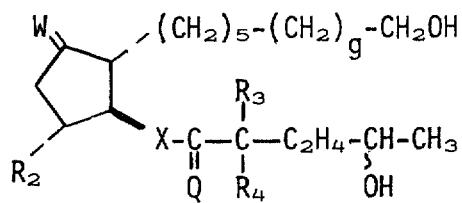

Column 123, line 2, "-PGF$_1$," should read -- PGF$_1\alpha$, --; line 45, "-29-hydroxy-" should read -- -19-hydroxy- --; line 47, "2-Decarboxy-2-hydroxymethyl-16,16-difluoro-" should read -- 2-Decarboxy-2-hydroxymethyl-11-deoxy-16,16-difluoro- --.

Signed and Sealed this

Ninth Day of June 1981

[SEAL]

Attest:

RENE D. TEGTMEYER

Attesting Officer   Acting Commissioner of Patents and Trademarks